(12) United States Patent
Trees et al.

(10) Patent No.: US 9,861,428 B2
(45) Date of Patent: Jan. 9, 2018

(54) INTEGRATED SYSTEMS FOR ELECTROSURGICAL STEAM OR SMOKE CONTROL

(71) Applicant: Ethicon Endo-Surgery, Inc., Cincinnati, OH (US)

(72) Inventors: Gregory A. Trees, Loveland, OH (US); Susan G. Arshonsky, Cincinnati, OH (US); Jonathan T. Batross, Mason, OH (US); Chad P. Boudreaux, Cincinnati, OH (US); Edward G. Chekan, Cincinnati, OH (US); Catherine A. Corbett, Cincinnati, OH (US); Craig T. Davis, Cincinnati, OH (US); Alex W. Kiturkes, Cincinnati, OH (US); Terry A. McFarland, Burlington, KY (US); David A. Monroe, Cincinnati, OH (US); John M. Sarley, Mason, OH (US); Frederick E. Shelton, IV, Hillsboro, OH (US); John B. Schulte, West Chester, OH (US); Foster B. Stulen, Mason, OH (US); Aaron C. Voegele, Loveland, OH (US); William B. Weisenburgh, II, Maineville, OH (US); Tamara Widenhouse, Clarksville, OH (US); David A. Witt, Maineville, OH (US)

(73) Assignee: Ethicon LLC, Los Frailes Industrial Park, Guaynabo, PR (US)

( * ) Notice: Subject to any disclaimer, the term of this patent is extended or adjusted under 35 U.S.C. 154(b) by 105 days.

(21) Appl. No.: 14/028,176

(22) Filed: Sep. 16, 2013

(65) Prior Publication Data
US 2015/0080879 A1    Mar. 19, 2015

(51) Int. Cl.
A61B 18/12    (2006.01)
A61B 18/14    (2006.01)
A61B 18/00    (2006.01)

(52) U.S. Cl.
CPC . *A61B 18/1445* (2013.01); *A61B 2018/00011* (2013.01); *A61B 2018/00607* (2013.01);
(Continued)

(58) Field of Classification Search
CPC ..... A61B 18/04; A61B 18/12; A61B 18/1442; A61B 18/1445; A61B 2018/00035;
(Continued)

(56) References Cited

U.S. PATENT DOCUMENTS 2,366,274 A    1/1945  Luth et al.
2,458,152 A    1/1949  Eakins
(Continued)

FOREIGN PATENT DOCUMENTS

DE    29623113 U1    10/1997
DE    20004812 U1     9/2000
(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Daniel Fowler

(57) ABSTRACT

A medical device includes an end effector configured to apply bipolar energy to target tissue along a working portion thereof and a fluid control system to control the flow of a fluid produced when the end effector applies the bipolar energy to heat the target tissue. The fluid control system (Continued)

includes a fluid path element defining a fluid path, a distal fluid port configured to intake the fluid adjacent to the working portion of an end effector for transport through the fluid path, and a proximal fluid port configured to intake the fluid transported through the fluid path and to exhaust the transported fluid.

20 Claims, 26 Drawing Sheets

(52) U.S. Cl.
CPC . *A61B 2018/1455* (2013.01); *A61B 2217/005* (2013.01); *A61B 2218/002* (2013.01); *A61B 2218/008* (2013.01)

(58) Field of Classification Search
CPC .... A61B 2018/00607; A61B 2218/006; A61B 2218/008
See application file for complete search history.

(56) References Cited

U.S. PATENT DOCUMENTS

| | | |
|---|---|---|
| 2,510,693 A | 6/1950 | Green |
| 3,166,971 A | 1/1965 | Stoecker |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,562,838 A * | 1/1986 | Walker ............... A61B 18/1402 219/230 |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,160,334 A | 11/1992 | Billings et al. |
| 5,190,541 A | 3/1993 | Abele et al. |
| 5,205,459 A | 4/1993 | Brinkerhoff et al. |
| 5,217,460 A * | 6/1993 | Knoepfler ............... 606/52 |
| 5,234,428 A * | 8/1993 | Kaufman ............... 606/45 |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,364 A | 3/1995 | Anderhub et al. |
| 5,395,900 A | 3/1995 | Slater et al. |
| 5,396,900 A | 3/1995 | Slater et al. |
| 5,403,312 A | 4/1995 | Yates et al. |
| 5,417,709 A * | 5/1995 | Slater ............ A61B 17/320016 604/27 |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A * | 10/1995 | Schmidt ................ A61B 17/29 604/35 |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A * | 3/1997 | Lichtman ............... 606/205 |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,138 A | 8/1998 | Shipp |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,827,323 A * | 10/1998 | Klieman ............... A61B 17/29 606/170 |
| 5,836,909 A * | 11/1998 | Cosmescu ............... 604/35 |
| 5,836,943 A | 11/1998 | Miller, III |
| 5,853,412 A | 12/1998 | Mayenberger |
| 5,876,401 A | 3/1999 | Schulze et al. |
| 5,880,668 A | 3/1999 | Hall |
| 5,891,142 A | 4/1999 | Eggers et al. |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |

(56) References Cited

U.S. PATENT DOCUMENTS

| | | |
|---|---|---|
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,144,402 A | 11/2000 | Norsworthy et al. |
| 6,152,923 A | 11/2000 | Ryan |
| 6,174,309 B1 | 1/2001 | Wrublewski et al. |
| 6,206,876 B1 | 3/2001 | Levine et al. |
| 6,228,080 B1 | 5/2001 | Gines |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,702 B2 | 10/2002 | Schulze et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,926,717 B1 * | 8/2005 | Garito ............... A61B 18/1442 606/51 |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |
| 7,550,216 B2 | 6/2009 | Ofer et al. |
| 7,559,452 B2 | 7/2009 | Wales et al. |

(56) References Cited

U.S. PATENT DOCUMENTS

| | | |
|---|---|---|
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,070 B2 | 1/2011 | Ortiz et al. |
| 7,879,035 B2 | 2/2011 | Garrison et al. |
| 7,901,400 B2 | 3/2011 | Wham et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,562,598 B2 | 10/2013 | Falkenstein et al. |
| 8,562,604 B2 | 10/2013 | Nishimura |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,404 B2 | 6/2014 | Boudreaux et al. |
| 8,753,338 B2 | 6/2014 | Widenhouse et al. |
| 8,764,747 B2 | 7/2014 | Cummings et al. |
| 8,926,608 B2 | 1/2015 | Bacher et al. |
| 8,951,248 B2 | 2/2015 | Messerly et al. |
| 8,956,349 B2 | 2/2015 | Aldridge et al. |
| 2002/0022836 A1 | 2/2002 | Goble et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |

(56) References Cited

U.S. PATENT DOCUMENTS

| | | |
|---|---|---|
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0191178 A1* | 7/2010 | Ross ............... A61F 9/00736 604/22 |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087209 A1 | 4/2011 | Boudreaux et al. |
| 2011/0087212 A1 | 4/2011 | Aldridge et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087220 A1 | 4/2011 | Felder et al. |
| 2011/0098700 A1* | 4/2011 | Tamai ............. A61B 17/00491 606/41 |
| 2011/0155781 A1 | 6/2011 | Swensgard et al. |
| 2011/0224668 A1 | 9/2011 | Johnson et al. |
| 2011/0251612 A1 | 10/2011 | Faller et al. |
| 2011/0276049 A1 | 11/2011 | Gerhardt |
| 2011/0276057 A1 | 11/2011 | Conlon et al. |
| 2011/0301605 A1 | 12/2011 | Horner |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2012/0010615 A1 | 1/2012 | Cummings et al. |
| 2012/0010616 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022530 A1 | 1/2012 | Woodruff et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116379 A1 | 5/2012 | Yates et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0265196 A1 | 10/2012 | Turner et al. |
| 2013/0023875 A1 | 1/2013 | Harris et al. |
| 2013/0030433 A1 | 1/2013 | Heard |
| 2013/0053831 A1 | 2/2013 | Johnson et al. |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artala |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0066022 A1 | 3/2015 | Shelton, IV et al. |
| 2015/0080876 A1 | 3/2015 | Worrell et al. |
| 2015/0080891 A1 | 3/2015 | Shelton, IV et al. |
| 2015/0133915 A1 | 5/2015 | Strobl et al. |
| 2015/0133921 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |

(56) References Cited

FOREIGN PATENT DOCUMENTS

| | | |
|---|---|---|
| EP | 2353518 A1 | 8/2011 |
| EP | 2508143 B1 | 2/2014 |
| GB | 2472216 A | 2/2011 |
| JP | H 08-229050 A | 9/1996 |
| JP | 2008-018226 A | 1/2008 |
| WO | WO 93/07817 | 4/1993 |
| WO | WO 93/22973 A1 | 11/1993 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 2000/024330 A1 | 5/2000 |
| WO | WO 2000/024331 A1 | 5/2000 |
| WO | WO 01/28444 A1 | 4/2001 |
| WO | WO 02/080797 A1 | 10/2002 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 03/001986 A2 | 1/2013 |
| WO | WO 2013/034629 A1 | 3/2013 |
| WO | WO 2013/062978 A2 | 5/2013 |

OTHER PUBLICATIONS

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.

Jang, J. et al. "Neuro-fuzzy and Soft Computing." Prentice Hall, 1997, pp. 13-89, 199-293, 335-393,453-496, 535-549.

Douglas, S.C. "Introduction to Adaptive Filter". Digital Signal Processing Handbook. Ed. Vijay K. Madisetti and Douglas B. Williams. Boca Raton: CRC Press LLC, 1999.

U.S. Appl. No. 14/158,248, filed Jan. 17, 2014.
U.S. Appl. No. 14/218,558, filed Mar. 18, 2014.
U.S. Appl. No. 14/149,294, filed Jan. 7, 2014.
U.S. Appl. No. 14/026,662, filed Sep. 13, 2013.
U.S. Appl. No. 14/075,839, filed Nov. 8, 2013.
U.S. Appl. No. 14/075,863, filed Nov. 8, 2013.
U.S. Appl. No. 14/227,699, filed Mar. 27, 2014.
U.S. Appl. No. 14/227,708, filed Mar. 27, 2014.
U.S. Appl. No. 14/028,163, filed Sep. 16, 2013.

International Search Report for PCT/US2014/053120, dated Nov. 14, 2014 (5 pages).

Written Opinion for PCT/US2014/053120, dated Nov. 14, 2014 (8 pages).

(56) References Cited

OTHER PUBLICATIONS

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
U.S. Appl. No. 14/032,391, filed Sep. 20, 2013.
IPRP for PCT/US2014/053120, dated Mar. 22, 2016 (9 pages).

* cited by examiner

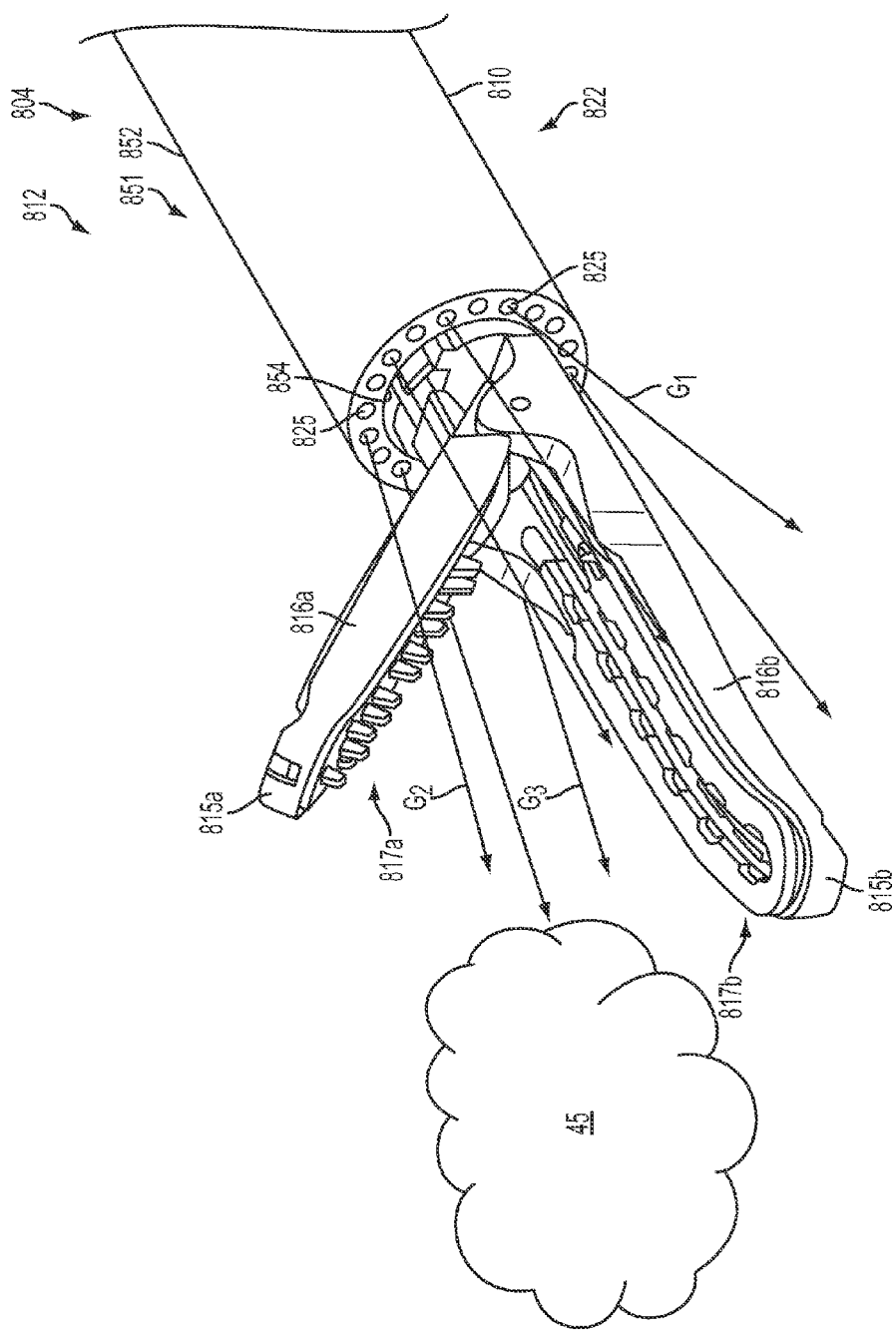

INTEGRATED SYSTEMS FOR ELECTROSURGICAL STEAM OR SMOKE CONTROL

BACKGROUND

The present disclosure relates generally to the field of surgery. In particular, the present disclosure relates to, although not exclusively, medical devices that perform work on target tissue via application of energy. More particularly, the present disclosure relates to, although not exclusively, fluid control systems designed to control steam, smoke, or temperature within a surgical field to protect tissue adjacent to target tissue.

Many surgical procedures require application of energy to target tissue. For example, medical devices such as surgical instruments may apply energy to tissue to cut or ligate blood vessels or other internal tissue. In many such procedures, it is desirable to achieve the surgical outcome using a minimally invasive technique that reduces trauma to non-target tissue. For example, electrosurgical medical devices generally include an end effector having an electrical contact to provide energy to target tissue. Advanced energy sealers may apply ultrasonic vibrational or RF energy to raise the temperature of target tissue above 100° C., for example. At this temperature, collagen is denatured and water may boil off to allow vessel walls to approximate tightly. Tissue adjacent to target tissue, however, may be blanched by steam if sufficiently close. Application of energy such as RF energy to target tissue may similarly produce a smoke plume when the target tissue is cooked. The electrosurgical smoke may be hazardous because it impedes visibility and causes delay when a surgeon must wait for the smoke to dissipate before continuing a procedure. Another risk associated with the application of energy is the presence of splay electricity and hot surfaces that may damage adjacent tissue within the surgical field. Accordingly, there is a need to advance this technology to address these and other issues associated with the use of medical devices configured to apply energy such as advanced energy to target tissue.

SUMMARY

In one embodiment, a medical device comprises a fluid control system to control the flow of a fluid produced when the medical device applies energy to heat a target tissue. The fluid control system comprises a fluid path element defining a fluid path to transport a fluid therethrough; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path; and an end effector fluidically coupled to the fluid control system, the end effector comprising a working portion extending along a first jaw and a second jaw, the working portion configured to apply bipolar energy to the target tissue, wherein the distal fluid port is positioned adjacent to the working portion of the end effector.

In another embodiment, a medical device comprises a fluid control system to control the flow of a fluid produced when the medical device applies energy to heat a target tissue. The fluid control system comprises a fluid path element defining a fluid path to transport a fluid therethrough, wherein the fluid path comprises a first fluid path at least partially defined by a first surface; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path; and an end effector fluidically coupled to the fluid control system, the end effector comprising a working portion configured to apply energy to the target tissue, wherein the distal fluid port is positioned adjacent to the working portion of the end effector.

In yet another embodiment, a medical device comprises a fluid control system to control the flow of a fluid produced when the medical device applies energy to heat a target tissue. The fluid control system comprises a fluid path element defining a fluid path to transport a fluid therethrough, wherein the fluid path comprises a first fluid path at least partially defined by a first surface; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path. The medical device further comprise an end effector fluidically coupled to the fluid control system, the end effector comprising a working portion configured to apply energy to the target tissue, wherein the distal fluid port is positioned adjacent to the working portion of the end effector, and wherein the first surface extends along a perimeter of the end effector.

In still yet another embodiment, a medical device comprises a fluid control system to control the flow of a fluid produced when the medical device applies energy to heat a target tissue. The fluid control system comprises a fluid path element defining a fluid path to transport a fluid therethrough; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path. The medical device further comprises an end effector fluidically coupled to the fluid control system, the end effector comprising a working portion configured to apply energy to the target tissue, wherein the distal fluid port is positioned adjacent to the working portion of the end effector; and an activation element configured to activate a supply and transport element to transport one the fluid through the fluid path.

In still yet an additional embodiment, a medical device comprises an elongate member having a proximal portion comprising a handle coupled to a proximal end of a shaft and a distal portion comprising an end effector coupled to a distal end of a shaft, the end effector comprising a first jaw, a second jaw, and a working portion, wherein the end effector is configured to apply energy to heat target tissue; a fluid control system configured to control one of steam and smoke generated when the end effector applies energy to heat target tissue, the fluid control system comprising a fluid path element comprising a fluid path; a distal fluid port positioned adjacent to the working portion of the end effector and fluidically coupled to the fluid path element; and a proximal fluid port fluidically coupled to the supply and transport element; wherein the fluid path is defined along a perimeter of the end effector between a first surface and a second surface, wherein the second surface comprises a gasket configured to form a seal with tissue.

FIGURES

FIG. 14 illustrates a perspective view of one embodiment of a distal portion of an elongate member comprising a fluid control system.

FIGS. 15A-5D illustrate cross-sectional views of certain configurations of fluid paths according to various embodiments.

DESCRIPTION

Figure 1:
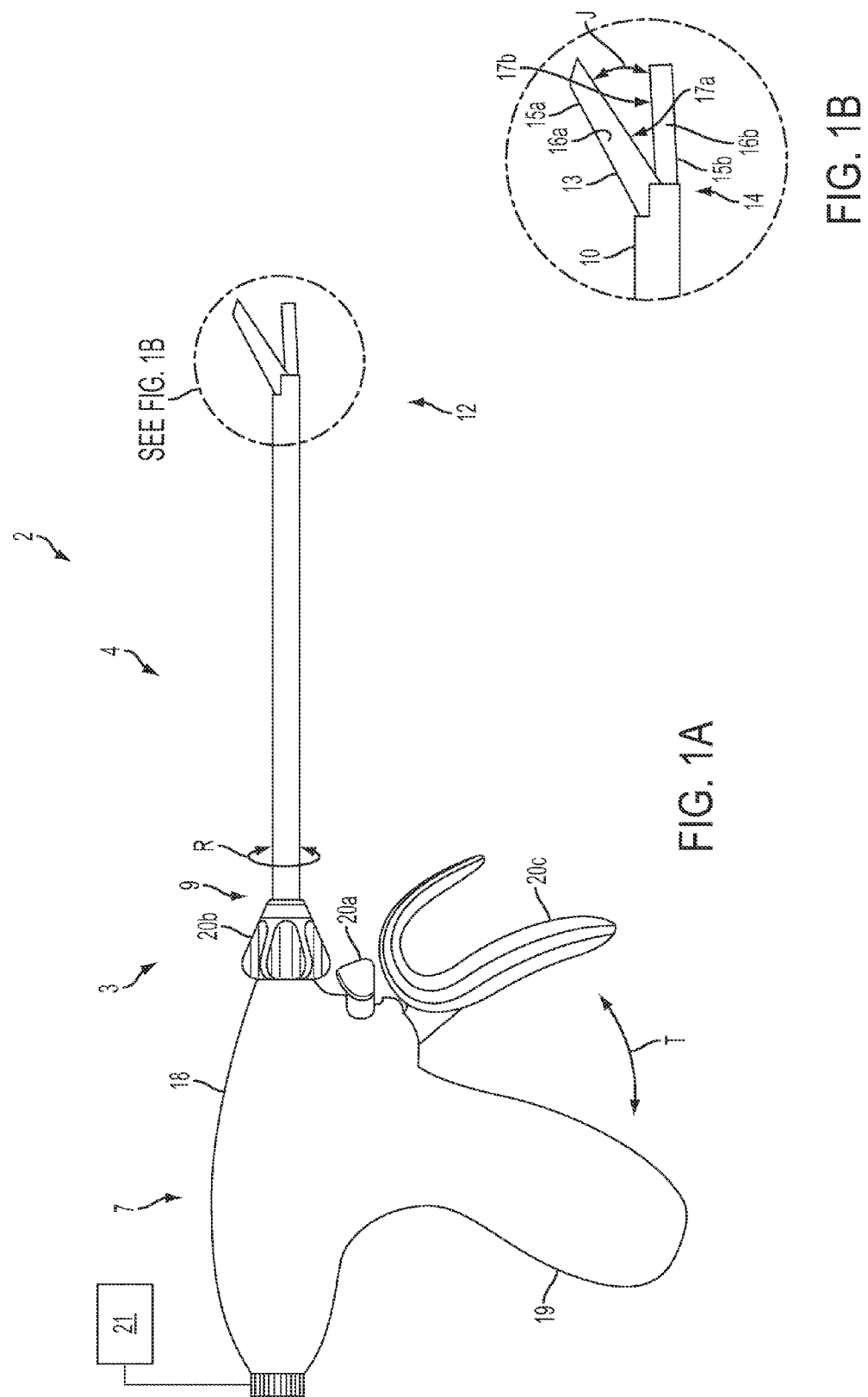
FIG. 1A illustrates a perspective view of one embodiment of a medical device including a fluid control system.
FIG. 1B illustrates an enlarged view of the distal portion of the elongate member illustrated in FIG. 1A.

Before explaining the various embodiments of ultrasonic and electrical surgical devices in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the ultrasonic and electrical surgical devices configured to apply energy, e.g., bipolar energy, to target tissue disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation. In the following description, like reference characters designate like or corresponding parts throughout the several views. Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

During medical procedures wherein energy including ultrasonic or RF energy, for example, is applied directly or indirectly to target tissue, e.g., an ultrasonic cutting device or a bi-polar RF device configured to seal, weld, cook, appose, transect, dissect, ablate, cauterize, electroporate, etc., tissue adjacent to the target tissue and surrounding the surgical field (generally referred to herein as adjacent tissue) may be susceptible to thermal damage that is directly or indirectly related to the procedure. For example, a medical device may include an end effector having a blade. Ultrasonic energy may be applied to the blade causing the blade to rapidly vibrate as it cuts target tissue to additionally coagulate tissue due to the frictional heat generated by the stress and vibration of the tissue. The heat used to coagulate the target tissue may result in generation of electrosurgical smoke, temperature fluctuations, or thermal pockets of steam that may be expelled or otherwise released into the surgical field causing undesirable damage to non-target tissue. As an additional example, a medical device comprising an end effector having electrodes for application of energy to weld target tissue. In a tissue welding or sealing procedure, for example, energy may be applied to target tissue to raise the temperature of the tissue above 100° C., e.g., above the boiling point of water. At these temperatures, collagen is denatured and water is boiled off to allow vessel walls to approximate tightly. Undesirably, adjacent tissue may be blanched by the steam produced when the water is boiled off. Thus the steam or smoke produced from the operation of such devices may be a byproduct of the direct or indirect application of energy to the target tissue.

According to various embodiments, a medical device may comprise or otherwise be integrated with a fluid control system. For clarity, the present disclosure generally describes a medical device as comprising an elongate member having a shaft, a proximal portion of the elongate member comprising a handle and a distal portion comprising an end effector. The shaft being positioned between the proximal and distal portions. However, those having skill in the art will appreciate that other medical devices may similarly comprise or otherwise be integrated with a fluid control system as described herein. Accordingly, the present disclosure is not so limited. In certain embodiments, the end effector comprises a working portion configured to apply energy to target tissue. As previously described, the energy may be ultrasonic vibrational energy or electrical energy and may be applied to the tissue directly or indirectly. As used herein, working portion is used to describe a portion of an end effector that performs work. As such, depending on the configuration, working portions of an end effector may include portions configured to grasp, cut, dissect, transect, tear, apply energy, etc. to target tissue. For example, an end effector comprising a first jaw and a second jaw may comprise a working portion extending along a length of the jaws. The working portion may correspond, for example, to an electrode configuration, e.g., a bipolar electrode configuration, or knife path. In one embodiment, the working portion A variety of medical devices that may comprise or otherwise be integrated with a fluid control system include medical devices having end effectors operable as ultrasonic tissue cutting elements or one or more elements that transmit RF energy to tissue (e.g., to coagulate or seal the tissue). Examples of such devices are the HARMONIC® blade and shears devices and the ENSEAL® Tissue Sealing Device by Ethicon Endo-Surgery, Inc., of Cincinnati, Ohio.

In one embodiment, the fluid control system comprises a fluid path element. The fluid path element may comprise one or more fluid paths configured to deliver fluid to or evacuate fluid from a surgical field. In certain embodiments, the fluid may comprise any fluid, including a gas, liquid, combination of the two, as well as fluids that may further include particulates, e.g., electrosurgical smoke. In various embodiments, the fluid path element may be defined in or associated with a medical device comprising an elongate member having a shaft positioned between a proximal portion of the elongate member comprising a handle and a distal portion of the elongate member comprising an end effector. The one or more fluid paths may comprise one or more distal fluid ports positioned to deliver, intake, exhaust, or evacuate fluid, which may include a fluid mixture, adjacent to the distal portion of the elongate member. For example, one or more fluid paths may be in fluid communication with one or more fluid ports, e.g., inlets, outlets, vents, etc., configured to deliver, intake, evacuate, or otherwise provide a point of ingress or egress for fluid with respect to the one or more fluid paths and surrounding environment. The one or more fluid paths may further comprise a proximal fluid port. In various embodiments, the one or more fluid paths may be defined by lumens, lines, channels, cavities, voids, tubing, or ducts defined in the elongate member, e.g., within a shaft, end effector, tube, or sleeve. The one or more fluid paths may provide a flow path for fluid to move or be transported between proximal and distal fluid ports. In one embodiment, a distal fluid port comprises an intake port adjacent to an end effector configured to intake fluid from the surgical field for movement or transport to a proximal fluid port positioned at another location, e.g., end effector, shaft, handle, fluid reservoir or exhaust environment, to evacuate the fluid. In various embodiments, the end effector comprises one or more proximal or distal fluid ports through which fluid, e.g., electrosurgical steam or smoke, may ingress or egress the one or more fluid paths directly through the end effector. In some embodiments, one or more fluid ports comprise vents formed into a side or outer portion or surface of the elongate member. It is to be appreciated that combinations of the one or more fluid paths may be independent or fluidically coupled to a common fluid path element.

In various embodiments, a fluid path element or fluid port comprises a filter. The filter may be any filter known in the art and may comprise an obstruction configured to prevent particulates or solids such as tissue and other debris from becoming lodged in and thereby clogging a fluid path element or port. For example, in one embodiment, a distal fluid port includes a membrane or filter to unwanted fluids and or debris from passing into the fluid path element and fouling the medical device, e.g., when a fluid path element may be clogged by debris or expose moisture sensitive components to moisture. In these or other embodiments, the fluid control system may be configured to provide a burst of fluid to ensure that a fluid path element or port is free of foreign obstructions or to dislodge foreign obstructions or fluids that may otherwise damage components of the medical device or its operation. For clarity and brevity, certain portions of the following description refer to a device comprising a fluid path element having a proximal fluid port and a distal fluid port, it is to be appreciated that multiple fluid paths may be used and multiple fluid ports may be associated with one or more of the multiple fluid paths.

In one embodiment, the fluid control system comprises or is fluidically coupled to a fluid supply and transport element, e.g., via a proximal fluid port. In various embodiments, the fluid supply and transport element comprises a supply component and a transport component. For example, the proximal fluid port may provide a fluidic coupling with the supply component to receive or exhaust fluid, e.g., into a reservoir or an external environment. Supply components may include fluid sources that provide fluid to the fluid path element as well as reservoirs or an external environment that receives fluid from the fluid path element. Supply components also may comprise or be coupled to fluid transport components. For example, fluid transport components may include any arrangement or manner of transport configured to transport fluid through the one or more fluid paths. For example, fluid, which may include fluid mixtures and particulates, e.g., steam or smoke, may be transported via pressure differentials, diffusion, convection, advection, gravity, etc. In some embodiments, a transport component comprises a positive or negative pressure that is applied within a fluid path to transport fluid. In one embodiment, the transport component includes a physical structure such as a pump that moves fluid through the fluid path element. For example, the pump may fluidically couple to the supply component and one or more fluid path channels of the fluid path element. The pump may be configured to supply positive or negative pressure to, for example, supply, evacuate, or transport fluid via one or more fluid paths. In one embodiment, the supply component is configured with the transport component, e.g., a compressed fluid, such as $CO_2$, wherein a pressure differential with respect to the one or more fluid paths drives decompression or evaporation to transport $CO_2$ through the one or more fluid paths.

In various embodiments, the fluid control system comprises or is operatively coupled to an activation element. The activation element may be configured to initiate or control the transport of fluid through the fluid path element. Thus, in certain embodiments, the activation element may be configured to control an operation of the fluid supply and transport element. In one embodiment, for example, the activation element comprises an actuator, switch, or other interface to provide or initiate power to a transport component comprising a pump for pumping fluid through the fluid path element. In another embodiment, the activation element comprises a switch that opens a valve fluidically coupled to the fluid path element and the fluid supply and transport element to allow fluid to be transported through the fluid path element. For example, the activation element may comprise a switch operatively coupled to a valve fluidically coupled between the fluid supply and transport element, e.g., a compressed fluid source, and the fluid path element. Actuation of the switch opens the valve, coupling a pressure differential that exists between a first and second side of the valve, causing fluid to be transported through the fluid path element.

In various embodiments, fluid delivered by the fluid control system interacts with adjacent tissue or steam generated from the application of energy to target tissue. For example, the fluid control system may reduce steam created when using a RF bipolar device to cauterize/seal and transect target tissue, thereby reducing trauma to surrounding tissue. In certain embodiments, the fluid control system is configured to deliver fluid adjacent the distal portion of the elongate member to displace or condense steam or smoke generated from the application of energy or to evacuate the same from the surrounding environment. In one embodiment, a fluid path is configured to inject or deliver a fluid to the surgical site adjacent the end effector or working portion thereof to reduce temperature induced damage to adjacent tissue, such as damage induced by thermal spread. For example, flowing fluid may disperse or absorb heat from steam or provide a protective shield. Additionally, depending on the desired application, fluid may be supplied or delivered at a temperature configured to counteract or otherwise protect adjacent tissue from an undesirable temperature fluctuation.

Further to the above, in one embodiment, fluid delivered to the tissue treatment site adjacent a distal portion of the elongate member or end effector via the one or more fluid paths may form a protective barrier between adjacent tissue and damaging temperature fluctuations, e.g., pockets of steam. In various embodiments, the fluid control system may be configured to deliver fluid via the one or more fluid paths to disperse the steam. For example, in one embodiment, fluid is supplied from one or more distal fluid ports. Distal fluid ports may be positioned adjacent to the tissue treatment site, a distal portion of the elongate member, or the end effector to deliver fluid at a volume or rate configured to disperse steam. Dispersing the steam may disperse concentrated thermal pockets of steam that may otherwise damage adjacent tissue. In various embodiments, the fluid is delivered at a rate or temperature configured to reduce the bulk temperature of the environment adjacent to the working end of the end effector while applying energy during surgery. In one embodiment, for example, the fluid delivery system is configured to deliver fluid to cool the surrounding tissue and/or cool and condense steam. In one embodiment, fluid may be delivered at a low temperature or density configured to condense steam or otherwise absorb heat adjacent to the distal portion of the elongate member, end effector, or surrounding tissue.

In various embodiments, as introduced above and described in more detail below, the fluid control system may be configured to suction, evacuate, or extract fluid from the surgical field adjacent to elongate member. For example, the fluid control system may comprise or be coupled to a transport component comprising negative pressure or vacuum to provide the same pressure at one or more distal fluid ports and extract or otherwise suction evolved steam away from adjacent tissue. In one embodiment, the fluid control system operates to extract, evacuate, or otherwise suction smoke generated from cooking tissue from the surgical field.

As introduced above, steam or mist may be created from the activation and/or application of energy. For example, activation of ultrasonic or RF bipolar energy with shear devices applied to tissues may cause the evolution of mist within the tissue or around the device. In various embodiments, a device may be configured to disperse or reduce the mist by application of the fluid adjacent to the elongate member. In one embodiment, the fluid control system delivers fluid, such as a liquid or gas, to a distal portion of the elongate member through one or more distal fluid ports. The delivery site may be located adjacent to the distal portion of the elongate member or within an internal region of the elongate member, e.g., within a cavity or channel defined within an end effector. In some embodiments, the fluid may be delivered by ejection or injection from a distal fluid port located on an internal or periphery surface and may be delivered by any manner known in the art, such as by diffusion, gravity, or pressure, e.g., a pump, collapsible bladder, injector, etc. In one embodiment, the rate of delivery may be controlled, such as by ejection or release, from one or more fluid ports. Fluid ports may be located on, around, or within the device and may be positioned to disperse or reduce mist by application of fluids to the surgical field.

As introduced above, application of energy to target tissue may produce a smoke plume when the target tissue is cauterized or coagulated, for example. Such electrosurgical smoke may be hazardous because it may impede visibility and cause delay when a surgeon must wait for the smoke to dissipate before continuing a procedure. At present, third-party portable smoke evacuators and suction systems generally provide less than optimal relief from electrosurgical smoke because in order to reduce the smoke the surgeon must compromise the available surgical field. That is, the third-party evacuator and suction systems occupy a portion of the surgical field and thereby reduce the space available for instruments or medical devices in the surgical field. In addition to reducing access to target tissue, the reduction in the surgical field also inhibits maneuverability of instruments and devices. According to various embodiments, the fluid control system is configured to manage smoke produced by the operation of a medical device, e.g., evacuate or disperse the smoke produced from the application of energy. For example, for procedures where evacuation of a smoke plume is not required, the smoke may be redirected by using the fluid control system as previously described. In one embodiment, the fluid control system comprises an insufflation pump, source of compressed gas, or other gas source that may be used to provide a flow or stream of gas through the device and out of the one or more distal fluid ports to disperse or divert smoke away from the distal portion of the elongate member and the surgical field.

In addition to generation of steam and smoke, operation of a medical device also may present risk to adjacent tissue within the surgical field due to, for example, splay electricity and hot surfaces. When access is limited, it may be difficult to maneuver the medical device while also protecting surrounding tissue from damage due to thermal spread from accidental contact during or after use of the device. In various embodiments, a medical device may comprise or be integrated with a fluid control system comprising a protective sleeve. For example, one or more components or surfaces of the elongate member may be fitted with a cover, e.g., a sleeve positioned over on a shaft or end effector. In one embodiment, a fluid path element comprises a cover or sleeve that at least partially defines one or more fluid path channels. It is to be appreciated that various embodiments may include multiple of the above general configurations of the fluid control system.

FIG. 1 illustrates a medical device 2 configurable with a fluid control system 3 according to various embodiments. The medical device 2 comprises an elongate member 4 having a proximal portion 6 comprising a handle 7 coupled to a proximal end 9 of a shaft 10. A distal portion 12 of the elongate member 4 comprises an end effector 13 coupled to a distal end 14 of the shaft 10. The proximal portion 6 comprises a handle 17 operatively coupled to the end effector 13 via the shaft 10. The end effector 13 comprises a first jaw 15a and a second jaw 15b, each having an outer portion or surface 16a, 16b. At least one of the first jaw 15a and the second jaw 15b is rotatably movable relative to the other along a path shown by arrow J to transition the jaws 15a, 15b between open and closed positions. In operation, the jaws 15a, 15b may be transitioned from the open position to a closed position to capture tissue therebetween. Captured tissue may contact one or more working portions of the jaw set, indicated generally as 17a, 17b, configured to apply energy, e.g., bipolar energy, to treat target tissue. Similarly, the working portion 17a, 17b may comprise a knife extendable along the jaws 15a, 15b through a slot defined within a central region of the end effector 13 or jaws 15a, 15b.

The handle 7 comprises a housing 18 defining a grip 19. In various embodiments, the handle includes one or more control interfaces 20a-c, e.g., a button or switch 20a, rotation knob 20b rotatable along arrow R, and a trigger 20c movable relative to the grip 19 along arrow T, configured to provide operation instructions to the end effector 13. The handle 7 is further configured to electrically couple to an energy source 21 to supply the medical device 2 with energy. While the energy source 21 is illustrated as generally coupled to the handle 7, e.g., with a cord, it is to be understood that in some embodiments the energy source 21 may be positioned within the elongate member 4. For example, in one embodiment, the energy source 21 comprises one or more direct current batteries positioned in the handle 7, shaft 10, or a portion thereof.

Figure 2:
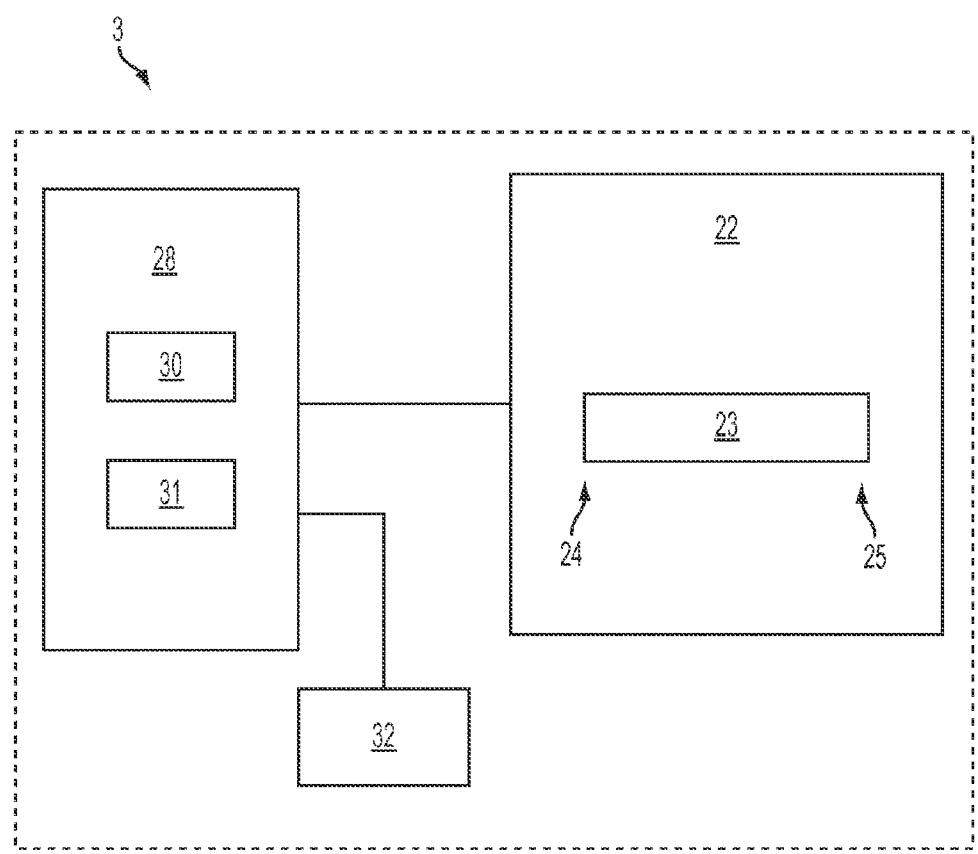
FIG. 2 illustrates one embodiment of a fluid control system shown in block diagram.

As introduced above, the medical device 2 includes or is configurable with the fluid control system 3 to control fluid, e.g., smoke, steam, or other fluid. FIG. 2 shows a schematic of one embodiment of a fluid control system 3. The fluid control system 3 includes a fluid path element 22 comprising one or more fluid paths 23. The one or more fluid paths 23 may be fluidically coupled to one or more proximal fluid ports 24 and one or more distal fluid ports 25. With further reference to FIG. 1, the one or more fluid paths 23 may extend along a portion of the shaft 10 and, in various embodiments, may further extend along the handle 7, end effector 13, or only along a portion of the end effector 13 or shaft 10. In certain embodiments, the fluid paths 23 may be defined by lumens, lines, channels, voids, ducts, cavities, or tubing which may be externally or internally positioned relative to the handle 7, shaft 10, or end effector 13 or may be integrally formed within such components of the medical device 2. For example, the fluid paths 23 may be integrated into the housing 18 of the handle 7, shaft 10, or end effector 13, or may comprise fluid paths configured as accessory features such as a cover, mold, attachment, sleeve, coating, or the like, that may be positioned on or associated with the handle 7, shaft 10, or end effector 13.

As introduced above, the fluid control system 3 may further comprise or be configured to fluidically couple to a fluid supply and transport element 28 comprising a supply component 30 and a transport component 31. The supply component 30 is configured to supply or receive fluid from the fluid path element 22 and may comprise a fluid source to supply fluid to a fluid path element 23 or a fluid reservoir, which may comprise an environment external to the fluid path element 23 to receive fluid from the fluid path element 22. The transport component 31 is configured to move fluid through the one or more fluid paths of the fluid path element 22. In various embodiments, the transport component 31 is configured to move fluid passively through the fluid path element 23 via gravity or diffusion, for example, and thus may not comprise a physical structure. In various embodiments, the transport component 31 comprises a pump or pressure differential configured to actively move or transport fluid through the fluid path element 22. For example, the transport component 31 may include a pressurized or compressed fluid supply or a pump to pressurize or compress the fluid supply. In one embodiment, the fluid supply system 3 includes a valve positioned between the supply component 30 and the fluid path element 22. Fluid path through the valve may be controlled to control transport of fluid through the one or more fluid paths. For example, the transport component 31 may comprise or generate a pressure differential between two outlets of the valve such that fluid is motivated to flow through the valve when the valve is open.

As previously described, the one or more fluid paths 23 may be fluidically coupled to one or more proximal fluid ports 24 and one or more distal fluid ports 25. The proximal fluid ports 24 may be positioned along the elongate member 4, e.g., within or adjacent to the handle 7, shaft 10, or end effector 13. The distal fluid ports 25 may be configured and positioned to deliver or intake fluid from the surgical field or tissue treatment site adjacent the distal portion 12 of the elongate member 4, e.g., the distal end 14 of the shaft 10, the end effector 13, or working portion thereof 17a, 17b.

The present description refers to the proximal fluid ports 24 and the distal fluid ports 25. The terms proximal and distal are generally used herein to spatially describe embodiments from the perspective of a user of the device 2. However, in regard to the proximal fluid ports 24 and the distal fluid ports 25 and associated fluid paths 23, proximal and distal refer to the position of the fluid port 24, 25 or fluid paths 23 with respect to a working portion of the end effector. For example, a distal fluid port 24 is most proximate to the position steam or smoke may be evacuated from the surgical field. Thus, while it may generally be the case that the distal fluid ports 25 are distal to the proximal fluid ports 24 in regard to the elongate member 4 taken from the perspective of a user, in various embodiments, a proximal fluid port 24 may be positioned distally of a distal fluid port 25, e.g., the end effector 13 may comprise a distal fluid port 25 at a proximal position of a jaw 15a, 15b and a proximal fluid port 24 at a distal portion of the jaw 15a, 15b to exhaust steam or smoke in a controlled or predictable manner. Thus, proximal and distal in this instance may refer to the extension of a fluid path element 23 relative to a region adjacent to the working portion of an end effector 13, which may be taken to be the distal most portion of the end effector 13 or fluid path element 23. For example, a fluid path element 23 may extend between a first end comprising a first fluid port and a second end comprising a second fluid port. The second fluid port may be positioned proximate to the working portion of the end effector to deliver fluid from the fluid path to a region adjacent to the working portion of the end effector 13 or thereby intake steam or smoke generated from the application of energy to the target tissue. The fluid path element 23 thus may extend proximally away from the second fluid port, or distal fluid port 25, to the first fluid port, or proximal fluid port 24, in the sense that the working portion is the distal most portion of the end effector 13 or fluid path element 23.

In various embodiments, the fluid control system 3 includes or is configured to associate with an activation element 32. The activation element 32 may be operatively coupled to the fluid supply and transport element 28 to activate the transport component 31 to, for example, provide power to a pump or to open a valve or port. In one embodiment, the activation element 32 comprises a switch electrically coupled to the energy source 21. The switch may be associated with the elongate member 4, e.g., the handle 7, or may be operatively coupled to the elongate member 4, such as a foot switch, to selectively activate the fluid control system 3. In some embodiments, the activation element 32 comprises a movable mechanical component, such as a switch or actuator, configured to open a valve to allow fluid to be transported through the one or more fluid paths 23. For example, the activation element 32 may include a switch or actuator operatively coupled to a piston or plunger that may be driven within or against a supply component 30 or fluid path element 23. Pressure resulting from movement of the piston or plunger may induce fluid transport, thus, operating as a transport component 31 to push or pull fluid through the one or more fluid paths 23. In one embodiment, the handle 7 includes a switch or actuator, which may be associated with the switch 20a or trigger 20c, that is coupled to the energy source 21 or valve to activate transport of fluid through the one or more fluid paths 23. In various embodiments, the activation element 32 may be configured to open a proximal fluid port 24 or a distal fluid port 25. The power may be manual or electrical, e.g., activation of the energy source 21 to provide energy to the end effector 13 may further activate the fluid control system 3. In one embodiment, the transport component 31 may, for example, comprise a bulb that may be squeezed to evacuate fluid from within the bulb or to expel or suction another fluid through one or more fluid paths 23. In various embodiments, the activation element 32 may be coupled to a valve fluidically coupled to the supply component 30 or the fluid path element 23. The activation element 32 may be configured to selectively operate the valve via an electrical or manual switch such that the valve may be opened or closed to control movement of fluid between the outlets of the valve. It is to be appreciated that the schematic provided in FIG. 2 is a general depiction of the scheme of the fluid control system 3 and does not represent an exhaustive representation of all the possible relationships, associations, and couplings of the components and elements of the fluid control system 3. For example, the transport component 31 or the supply component 30 may be connected or positioned at various locations within or relative to the one or more fluid paths 23 of the fluid path element 22. For example, the transport component 31 may comprise a pump that is positioned inline with a fluid path element of the one or more fluid paths 23, e.g., coupled to a proximal fluid port 24 of the one or more fluid paths 23, or between a first fluid path element and a second fluid path element of the one or more fluid paths 23. The supply component 30 may be connected or positioned inline with the same or different fluid path element 23 or may be positioned on either side of the first or second fluid path element. In various embodiments, the handle 7 may be configured to house or couple to one or more components or elements of the fluid control system 3. For example, the handle 7 may comprise a proximal fluid port 24 configured to fluidically couple to a fluid supply component 30 or fluid transport component 31, as previously described. The handle 7 also may be configured to operatively couple with an activation element 32 when present.

According to various embodiments, the activation element 32 may be configured to sequence activation of the fluid control system 3, e.g., via activation of the fluid transport component 31 to transport fluid through the one or more fluid ports 23, with an operation of the end effector 13. The sequence may be before, after, substantially simultaneous or contemporaneous to the activation of energy or another operation of the end effector 13, such as opening, clamping, or locking of jaws 15a, 15b. In some embodiments, the fluid control system 3 is activated to perform one or more fluid control functions at multiple locations relative to the end effector 13. These control functions may differ by location to provide customizable steam or smoke control. Activation of the fluid control system 3 to perform control functions may similarly be temporally controlled to occur at multiple time periods with respect to the operation of the end effector 13. For example, the fluid control system 3 may be activated just prior to activation of energy to deliver or intake a fluid. In one embodiment, the fluid control system 3 may be further activated to deliver or intake the same or different fluid at a later time, such as during or after the activation of energy. As introduced above, the activation element may be configured to couple activation of fluid control system with activation of energy. As an example, in one embodiment, operation of the switch 20a or moving the trigger 20c along arrow "T" causes activation of the transport component 31, e.g., activation of a pump or opening of a valve separating a pressure differential. Operation of the switch 20a or movement of the trigger 20c may provide a signal to a generator associated with the energy source 21 to activate energy and the fluid control system 3. As previously described, activation of energy and fluid control functions may be sequenced to occur at different times and locations with respect to the operations of the end effector 13. In certain embodiments, one or more sequences are preprogrammed in a memory module and selectable via user interface controls associated with the handle 7 or a generator. In one embodiment, the user may select or design one or more sequence programs before or during use to suit a desired use of the medical device 2.

In various embodiments, the supply component 30 is configured to supply a gas, e.g., a biologically compatible or inert gas, that is transported through one or more fluid paths 23. One or more distal fluid ports 25 may deliver the gas adjacent to the distal portion 12 of the elongate member 4, e.g., distal end 14 of the shaft 10, end effector 13, or working portion thereof 17a, 17b. In one embodiment, the fluid control system 3 is configured to produce a gas flow around the end effector 13 to disperse steam and, in some embodiments, absorb heat from the steam. For example, the gas may be delivered at a low temperature to blow cold gas at an increased rate around the end effector 13 to absorb heat from steam or cool surrounding tissue. In one form, the supply component 30 comprises a liquid that may be evaporated to provide a cold gas supply. For example, a gas source may comprise liquid $CO_2$ that is supplied from an insufflation gas source or external tank. As stated above, the gas flow may also disperse steam or smoke, which may increase visibility as well as avoid damage to adjacent tissue.

In various embodiments, the supply component 30 is configured to supply a liquid, e.g., which may be water, saline, or other biologically compatible liquid, that is transported through one or more fluid paths 23. One or more distal fluid ports 25 may deliver the liquid adjacent to the distal portion 12 of the elongate member 4, e.g., distal end 14 of the shaft 10, end effector 13, or working portion thereof 17a, 17b. In certain embodiments, the liquid irrigates the adjacent tissue by, for example, providing liquid adjacent to the end effector 13. The liquid may flush surrounding tissue to cool the tissue or condense steam. In some embodiments, irrigation of adjacent tissue may cool and protect the surrounding tissue from thermal damage. For example, the fluid control system 3 may be configured to deliver the liquid at a volume, rate, and location to form a protective liquid shield or thermal barrier between the steam generated from the application of energy and tissue. In these or other embodiments, the liquid may be delivered at a temperature configured to assist in condensing the steam to protect adjacent tissue. For example, a protective barrier provided by the liquid may thus capture steam generated by the cooking of target tissue and also cool surrounding tissues to keep the steam and plume from dispersing through and desiccating the surrounding tissue.

In various embodiments the fluid control system 22 is configured to deliver a fluid comprising a gas liquid mixture, e.g., a mist, adjacent to the distal portion 12 of the elongate member 4, e.g., distal end 14 of the shaft 10, end effector 13, or working portion thereof 17a, 17b. For example, the one or more fluid paths 23 may include a proximal fluid port 24 configured to couple to a supply component 30 and transport component 31. The supply component 30 may comprise a liquid, which in certain embodiments may further include a gas. The transport component 31 may comprise a pump to push or pull the fluid through the one or more fluid paths 23 toward one or more distal fluid ports 25 or a valve operable to allow pressurized or compressed fluid from the supply component 30 to decompress and move through the one or more fluid paths 23. In one embodiment, the one or more distal fluid ports 25 comprise a nozzle configured to produce a mist formed from a liquid and a gas. The mist may engulf the end effector 13 or portion thereof, e.g., an outer portion or surface 16a, 16b of the end effector 13. Interaction of the mist with the steam generated from the heating of the target tissue may actively cool the steam and, therefore, reduce potential damage to adjacent tissue. The mist may also disperse or condense the steam. As previously described, the fluid control system 3 may be configured to spray the mist simultaneously with the activation of the end effector 13, e.g., to coincide with application of energy, or other times associated with operations of the end effector 13.

In one embodiment, the medical device 2 comprises a laparoscopic bi-polar device comprising an elongate member 4 including handle 7, shaft 10, cord to couple to a energy source 21, and an end effector 13 for apposing tissue. The device 2 comprises or is equipped with a fluid control system 3 comprising one or more fluid paths 23 defined in a lumen of a fluid path element 22 that extends along the elongate member 4. The one or more fluid paths 23 provide a path for fluid to travel between a proximal fluid port 24 and a distal fluid port 25. The proximal fluid port 24 is configured to fluidically couple with a fluid supply and transport element 28 configured to supply and transport fluid through the one or more fluid paths 23. For example, the proximal fluid port 24 may be coupled to a supply component 30 and transport component 31, such as a fluid retention tank and a pump to affect the pressure of the supply component 30, to enable fluid to travel distally through the one or more fluid paths 23. The distal fluid port 25 may comprise a nozzle for creating a mist from the fluid, as previously described. A generator may be used to activate a power source to power the bi-polar device and subsequently simultaneously activate the pump, for example through the cord, to transport fluid through the fluid path element 23 defined by the lumen of the fluid path element 22 such that a misting is created when the fluid exits the distal fluid port 25 during the bi-polar activation.

Although generally described with respect to an end effector comprising collapsible jaws configured to apply energy, e.g., bipolar energy, to target tissue, e.g., an ultrasonic or bi-polar device configured to seal, bond, weld, separate, cut, ablate, etc. target tissue, those having skill in the art will recognize that the present disclosure may be broadly applicable to other medical devices and end effector configurations. With this in mind, for clarity and ease of understanding, the following description of the embodiments uses like identifiers for similar features and, thus, specific features may not necessarily be described in detail with respect to every embodiment. Similarly, various embodiments are described in reference to figures illustrating a distal portion of an elongate member of a medical device. It is to be understood that a corresponding proximal portion may be configured as otherwise described for other embodiments, e.g., as generally previously described. Additionally, it is to be understood that, unless stated otherwise, the embodiments depicting fluid paths and fluid ports associated with a portion of an end effector, e.g., a first jaw or side of a first jaw or a second jaw, may also include similar fluid paths and fluid ports associated with another portion of the end effector, e.g., a second jaw or other side of the first jaw or second jaw.

Figure 3A:
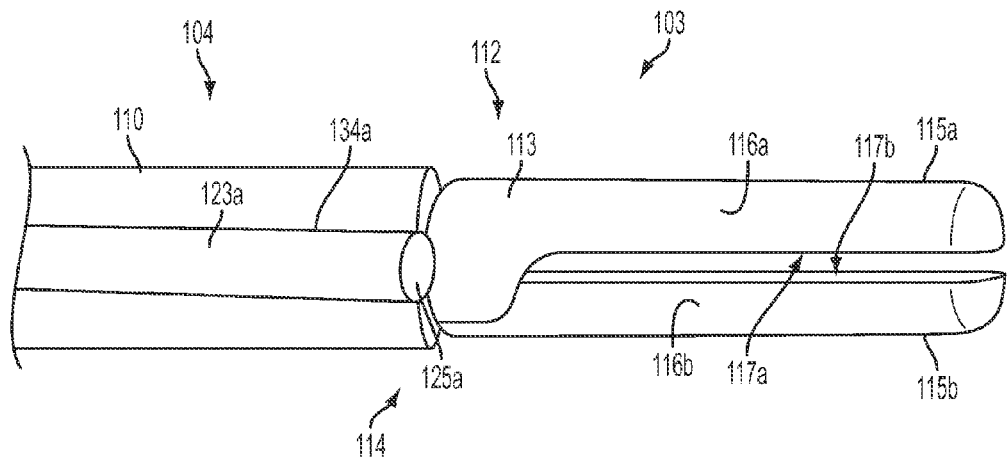
FIG. 3A illustrates a perspective view of one embodiment of a distal portion of an elongate member comprising a fluid control system.
Figure 3B:
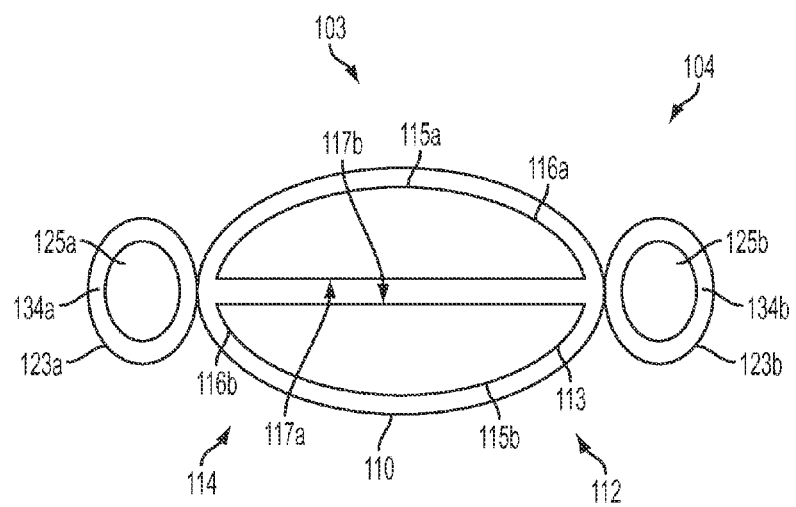
FIG. 3B illustrates a distal to proximal perspective view from the distal portion of the elongate member illustrated in FIG. 3A.
Figure 4A:
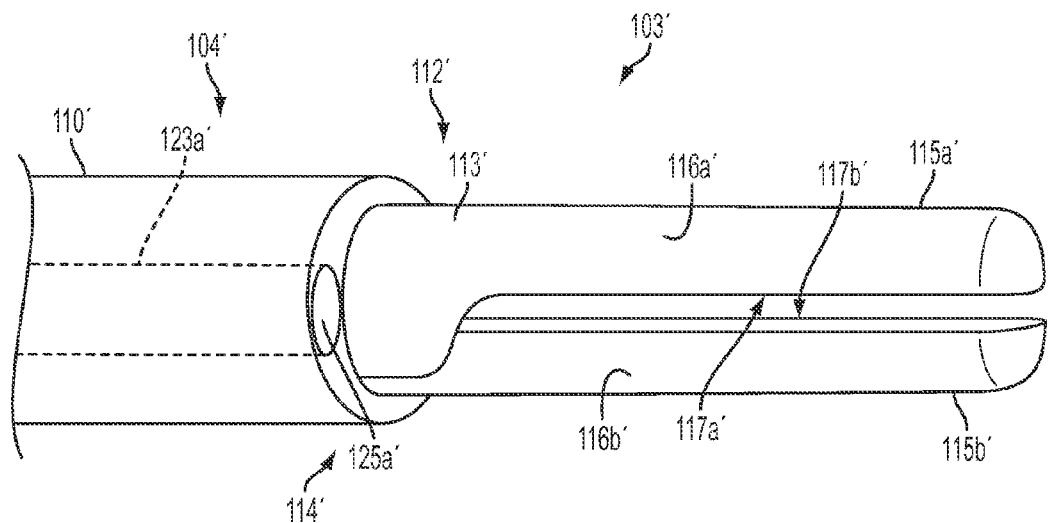
FIG. 4A illustrates a perspective view of one embodiment of a distal portion of an elongate member comprising a fluid control system.
Figure 4B:
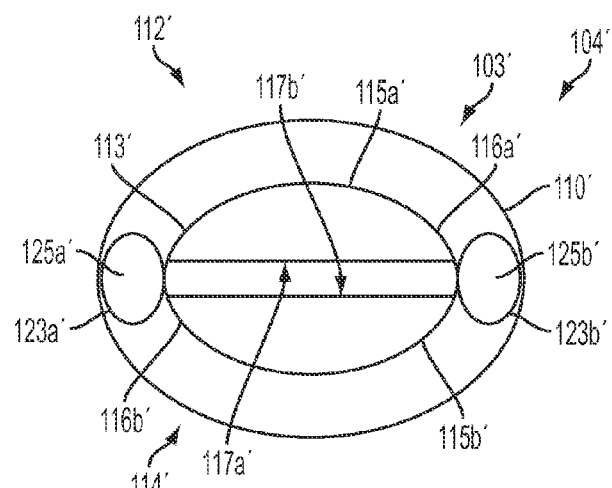
FIG. 4B illustrates a distal to proximal perspective view from the distal portion of the elongate member illustrated in FIG. 4A.
Figure 5A:
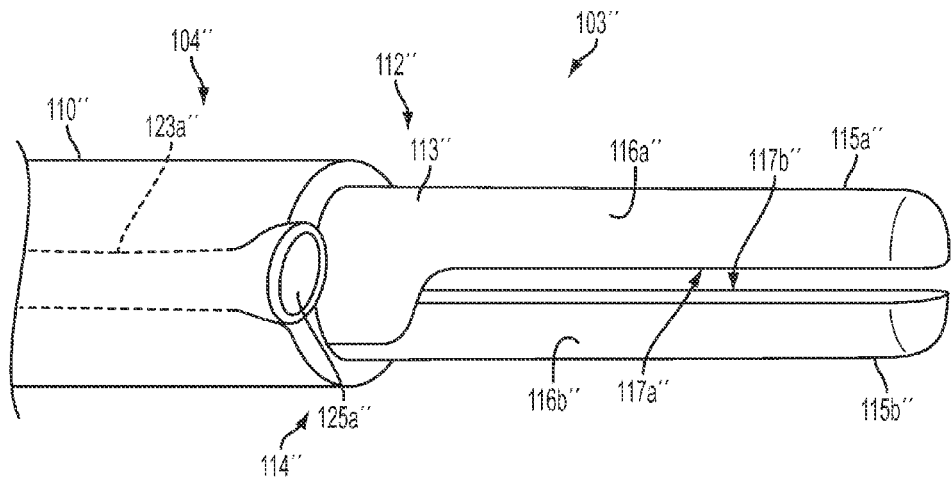
FIG. 5A illustrates a perspective view of one embodiment of a distal portion of an elongate member comprising a fluid control system.
Figure 5B:
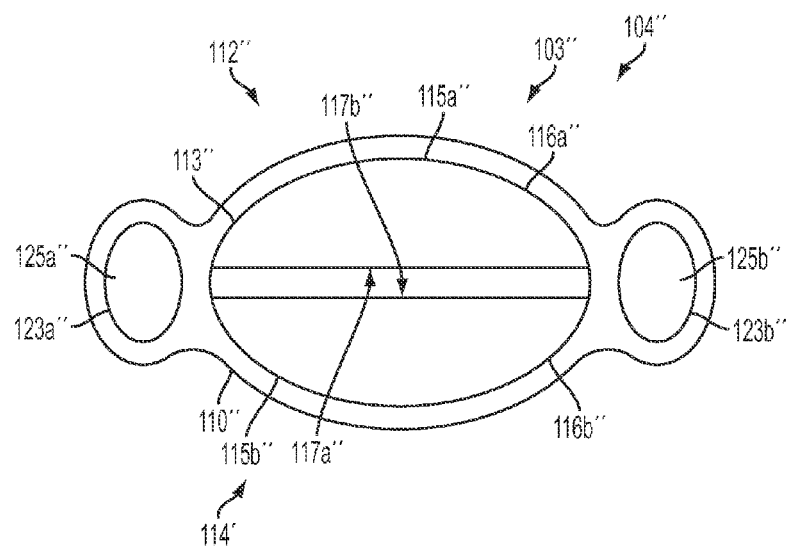
FIG. 5B illustrates a distal to proximal perspective view from the distal portion of the elongate member illustrated in FIG. 5A.

FIGS. 3A and 3B illustrate one embodiment of a distal portion 112 of an elongate member 104 of a medical device comprising a fluid control system 103. The elongate member 104 comprises a shaft 110 having a distal end 114 coupled to an end effector 113. The end effector 113 comprises first and second jaws 115a, 115b configured to apply energy, e.g., bipolar energy, to target tissue positioned along working portions 117a, 117b. Similarly, the working portion 117a, 117b may comprise a knife extendable along the jaws 115a, 115b through a slot defined within a central region of the end effector 113 or jaws 115a, 115b. One or more fluid paths 123a, 123b extend along at least a portion of the shaft 110. In various embodiments, the fluid paths 123a, 123b may extend further along a handle (not shown) of the medical device. The fluid paths 123a, 123b may be defined by lumens, lines, channels, voids, cavities, or tubing, which may include lines or tubing 134a, 134b positioned along the shaft 110 and/or may be integrally formed within the shaft 110 or other component of the medical device. As such, fluid may be transported through the fluid paths 123a, 123b via exterior lines or tubing 134a, 134b in an open environment. The lines or tubing 134a, 134b may be coupled to components of the elongate member 104 at one or more points. FIGS. 4A and 4B illustrate one embodiment of a distal portion 112' of an elongate member 104' of a medical device comprising a fluid control system 103'. This embodiment is similar to the embodiment previously described with respect to FIGS. 3A and 3B except the one or more fluid paths 123a', 123b' extend along at least a portion of the shaft 110' and are further designed to be flush with an outer circumference of the shaft 110'. Thus, the shaft 110' may comprise various cross-sections, which may be uniform along its length or irregular. FIGS. 5A and 5B illustrate another embodiment of a distal portion 112" of an elongate member 104" of a medical device comprising a fluid control system 103". This embodiment is similar to the embodiments of FIGS. 3A-4B except the one or more fluid paths 123a", 123b" extend internally through the shaft 110" proximally and protrude outward of the shaft 110" distally to form protruding distal fluid ports 125a", 125b" positioned at the distal end 114" of the shaft 110'". The fluid paths 123a', 123b', 123a", 123b" may be defined by channels, lumens, voids, lines, tubing, ducts, or cavities within the shaft 110' or may integrally formed within the various components of the medical device. For example, in one embodiment, components within the shaft 110', 110" are arranged such that a series of voids or cavities between components within the shaft may be used to provide one or more fluid paths 123a', 123b', 123a", 123b". It is to be appreciated that the angle, number, cross-section, arrangement, and position of the distal fluid ports 125a, 125b, 125a', 125b', 125a", 125b" may be varied to suit particular applications and end effectors. For example, the angle and position may be such that fluid delivered from the fluid control system 103, 103', 103" forms a fluid barrier or wall along the outer portion or surface 116a, 116b, 116a', 116b', 116a", 116b" of the end effector 113, 113', 113". The number and cross-section may similarly be increased or decreased to provide greater or more defined fluid path at one or more points.

The distal fluid ports 125a, 125b, 125a', 125b', 125a", 125b" illustrated in FIGS. 3A-5B are positioned to deliver or intake fluid from a surgical field adjacent to the distal portion 112, 112', 112" of the elongate member 104, 104', 104", e.g., the distal end of the shaft 110, 110', 110", the end effector 113, 113', 113", or working portion thereof 117a, 117b, 117a', 117b', 117a", 117b". In particular, the distal fluid ports 125a, 125b, 125a', 125b', 125a", 125b" are arranged on either side of the end effector 113, 113', 113", proximal to working portions 117a, 117b, 117a', 117b', 117a", 117b", and are positioned intermediate the first and second jaws 115a, 115b, 115a', 115b", 115a', 115b" where fluid, such as steam or smoke, for example, is most likely to be produced or released during application of energy to the target tissue. Thus, the distal fluid ports 125a, 125b, 125a', 125b', 125a", 125b" may comprise various configurations which may, for example, complement a configuration or operation of the end effector 113, 113', 113". As previously described, the one or more fluid paths 123a, 123b, 123a', 123b', 123a", 123b" may be configured to couple to fluid supply and transport system elements such as a supply component and a transport component, which may be further associated with an activation element. It is to be appreciated that fluid paths 123a, 123b, 123a', 123b', 123a", 123b" may be separate fluid paths, e.g., comprise at least partially independent paths for fluid or may comprise a primary or common fluid path with one or more branches into secondary or tertiary fluid paths that extend to one or more distal fluid ports 125a, 125b, 125a', 125b', 125a", 125b", as described in more detail below.

Figure 6:
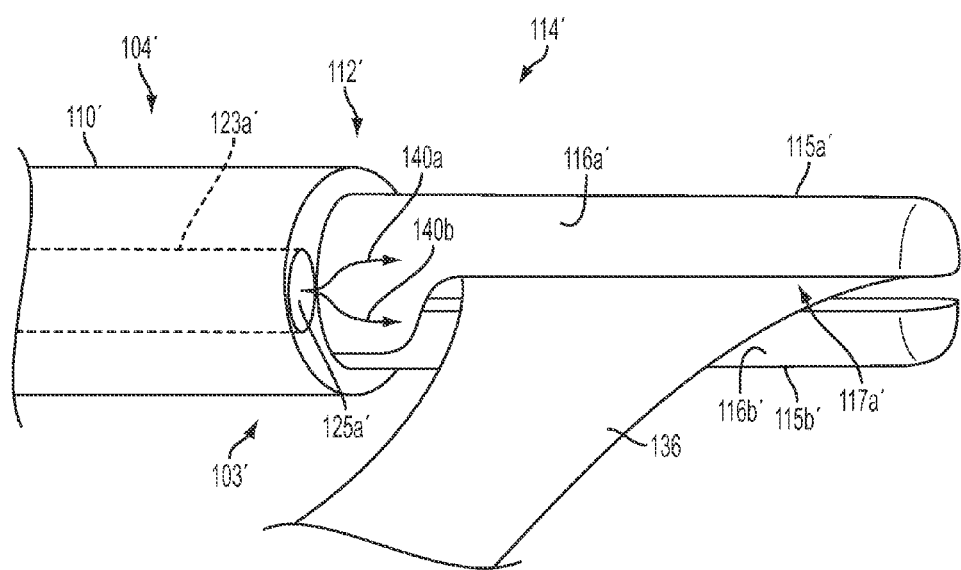
FIG. 6 illustrates a perspective view of an operation of the fluid control system illustrated in FIGS. 4A and 4B.

FIG. 6 illustrates an operation of the fluid control system 103' illustrated in figure FIGS. 4A and 4B according to one embodiment. In various embodiments, a same or similar operation may be applicable to the configurations shown in FIGS. 3A and 3B and FIGS. 5A and 5B. The first jaw 115a' and second jaw 115b' of the end effector 113' are shown in a closed position having target tissue 135 positioned intermediate working portions 117a' and 117b' (not visible). The fluid path 123a' is configured to fluidically couple with a supply component and transport component, which may be further associated with an activation element, as previously described. The distal fluid port 125a' is positioned at the distal end 114' of the shaft 110', adjacent to the end effector 113'. When the fluid control system 103' is activated, fluid is transported through the fluid path 123a and delivered to the surgical field as generally depicted by arrows 140a, 140b at the distal fluid port 125a'. As previously described, the fluid may be a gas, liquid, or mixture thereof and may be delivered adjacent to the distal portion 112' of the elongate member 104', e.g., the distal end of the shaft 114', the end effector 113', or a working portion thereof 117a', 117b'. The fluid may be delivered at a temperature, rate, and pattern configured to disperse the fluid, e.g., steam or smoke, or absorb heat from the fluid.

In some embodiments, the fluid path element may be configured to provide a protective shield. For example, fluid may wrap around the end effector 113' or create a fluid wall, e.g., a cylindrical wall, around the outer portion or surface 116a' of the end effector 113', between steam or smoke and adjacent tissue 136, as previously described. In one embodiment, the fluid control system 103' is configured to activate at times and locations corresponding to operations of the end effector 113'. For example, in one embodiment, the fluid control system 103' is configured to deliver fluid upon activation of energy or sequence delivery of fluid with multiple operations of the end effector 113'. In this way, a protective barrier may be formed with the fluid to capture the steam produced by the application of energy to target tissue, e.g., cauterization of the target tissue 135 to be apposed. For example, liquid may be delivered or begin to be delivered when the end effector 113' begins to apply energy that is transferred to target tissue 135, as previously described. In one embodiment, compression of target tissue 135 intermediate the jaws 115a', 115b' occurs before liquid and energy are delivered to the target tissue 135, therefore, the target tissue 135 may be energized without interference from the liquid. While not visible in FIG. 6, in certain embodiments, fluid may similarly be transported through the fluid path 123b' and delivered to the surgical field at the distal fluid port 125b' to control steam or smoke as previously described with respect to the fluid path element 123a' and the distal fluid port 125a'. In this or another embodiment, the fluid control system 103' may be configured to suction steam or smoke generated from the application of energy to target tissue 135 away from the adjacent tissue 136. For example, the transport component may be configured to generate negative pressure or a vacuum within the one or more fluid paths 123a', 123b' to suction steam or smoke through the distal fluid ports 125a', 125b' away from the adjacent or surrounding tissue, e.g., in the direction opposite arrows 140a, 140b. In such embodiments, the distal fluid ports 125a, 125b may be shaped and positioned to preferentially pull steam or smoke from on or more regions of the surgical field, e.g., adjacent to the working portions 117a', 117b' of the end effector 113.

Figure 7:
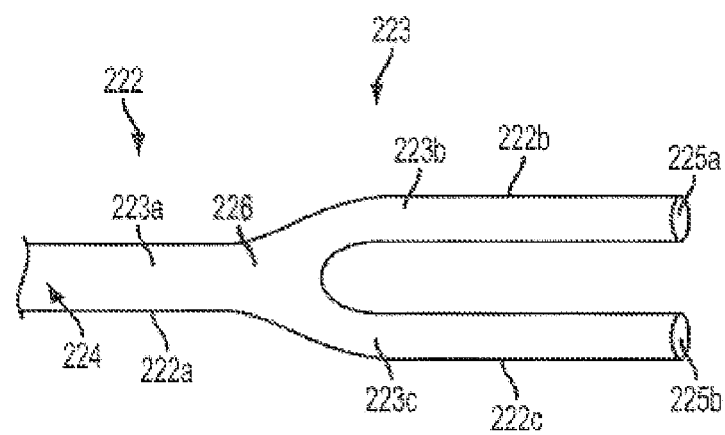
FIG. 7 illustrates one embodiment of a fluid path element of a fluid control system comprising one or more fluid paths.

FIG. 7 illustrates one embodiment of a configuration of a fluid path element 222 comprising one or more fluid paths 223 for use in a fluid control system according to various embodiments. A first fluid path element 223a is fluidically coupled to a second fluid path element 223b and a third fluid path element 223c via an intermediate fluid port 226. The first fluid path element 223a diverges or branches into the second fluid path element 223b and third fluid path element 223c. The second fluid path element 223b and the third fluid path element 223c similarly converge into the first fluid path element 223a. In various embodiments, the one or more fluid paths 223 may extend along an elongate member. For example, the configuration of the one or more fluid paths 223 illustrated in FIG. 7 may be similar to the configuration of the one or more fluid paths in the embodiments depicted in FIGS. 3A-6. The one or more fluid paths 223 may be fluidically coupled to a proximal fluid port 224 configured to fluidically couple to a fluid supply and transport element, which may be operatively coupled to an activation element, as previously described. The one or more fluid paths 223 further comprise distal delivery ports 225a, 225b configured to deliver or intake fluid.

Figure 8:
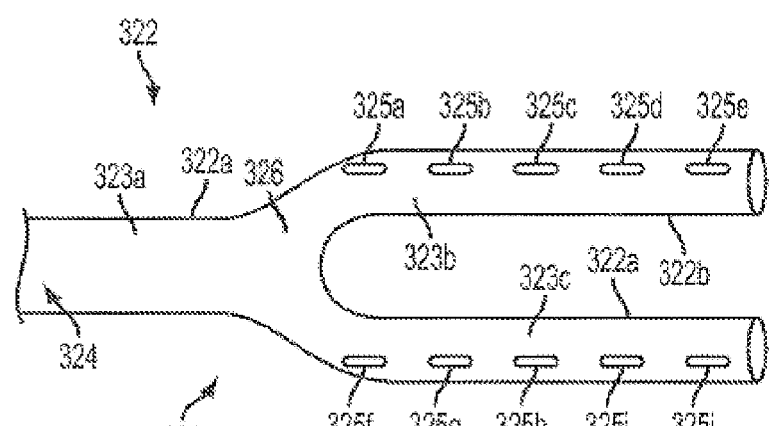
FIG. 8 illustrates one embodiment of a fluid path element of a fluid control system comprising one or more fluid paths.

In various embodiments, referring to FIG. 8, a fluid path element 322 comprises one or more fluid paths 323 fluidically coupled to multiple distal fluid ports 325a-325j. For example, a first fluid path 323a is shown diverging or branching into a second fluid path element 323b and third fluid path element 323c, which similarly converge into the first fluid path element 323a, via an intermediate fluid port 326 fluidically coupling the fluid paths 323a-323c. In various embodiments, the one or more fluid paths 323 extend along an elongate member. For example, the second fluid path element 323b may extend along a first portion of an end effector, e.g., a first jaw or first side, and the third fluid path element 323c may extend along a second portion of the end effector, e.g., a second jaw or second side. As previously described, the fluid paths 223, 323 may be defined by lumens, lines, channels, voids, ducts, cavities, or tubing located within the shaft, end effector or associated tubing, lines, molds, sleeves, or covers, for example, or may be or integrally formed therein. A proximal end of the one or more fluid paths 323 may comprise a proximal fluid port 324 configured to fluidically couple to a fluid supply and transport element, which may be operatively coupled to an activation element, as described herein.

Figure 9:
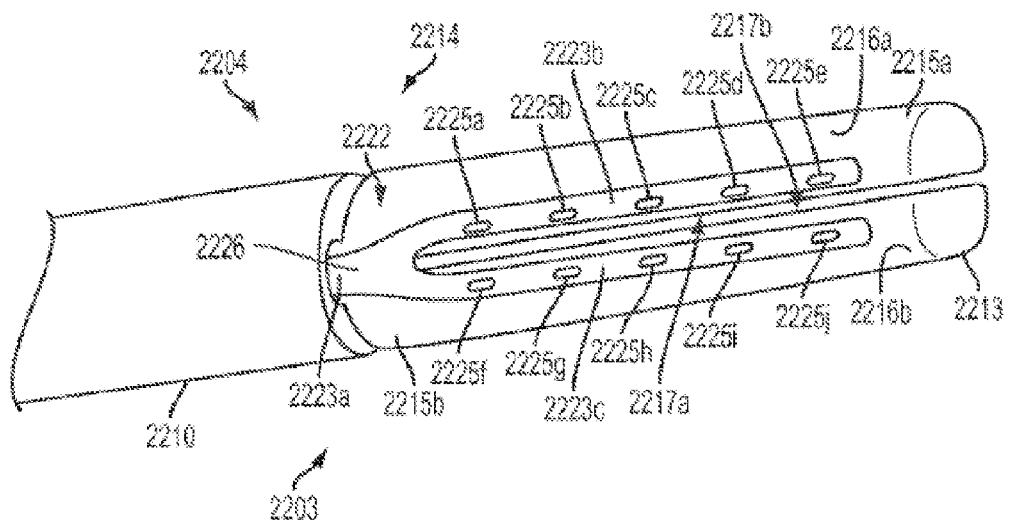
FIG. 9 illustrates a perspective view of one embodiment of a distal portion of an elongate member comprising a fluid control system.

Referring to FIG. 9, in one embodiment, a fluid path element 2222 may comprise one or more fluid paths 2223 that extend along a shaft 2210 and an end effector 2213 of an elongate member 2204. The one or more fluid paths 2223 define a y-configuration, e.g., similar to that depicted in FIG. 8, and comprise a first fluid path or element 2222a defining a first fluid path 2223a that extends along the shaft 2210. The first fluid path element 2222a diverges distally to branch into a second fluid path element 2222b defining a second fluid path 2223b and a third fluid path element 2222c defining a third fluid path 2223b, which similarly converge into the first fluid path element 2222a and first fluid path 2223a proximally, via an intermediate fluid port 2226 fluidically coupling the fluid paths 2223a-2223b. The first fluid path 2223a may extend through the shaft 2210 and the first fluid path element 2222a may comprise tubing, a channel, or a cavity, for example. The first fluid path element 2222a further may comprise a proximal fluid port (not shown) configured to fluidically couple, e.g., via a coupling to an additional fluid path element, to additional components of the fluid control system 2203, such as a fluid and transport element, which may be operatively coupled to an activation element, as described herein. For example, the shaft 2210 or an additional fluid path may comprise a fitting to couple the first fluid path element 2222a with the additional fluid path element. The second fluid path element 2222b and the third fluid path element 2222c are respectively positioned to extend along the first and second jaws 2215a, 2215b and each comprises one or more distal fluid ports 2225a-2225j positioned therealong. Specifically, the distal fluid ports 2225a-2225j are positioned adjacent the distal portion 2212 of the elongate member 2204, e.g., along an outer portion or surface 2216a, 2216b of the end effector 2213 or working portion thereof 2217a, 2217b. The distal fluid ports 2225a-2225j are positioned to provide delivery of fluid outward or away from the jaws 2215a, 2215b or to intake fluid, e.g., steam or smoke, inward or toward the jaws into the respective fluid paths 2223b, 2223c. As such, the distal fluid ports 2225a-2225j may be arranged in various configurations which may, for example, complement a configuration or operation of the end effector 2213. In this way, a fluid or vacuum may be provided proximate the regions steam or smoke is likely to be generated or escape the jaws 2215a, 2215b. While not shown in FIG. 9, the elongate member 2204 may include similarly configured fluid paths defining fluid paths and distal fluid ports on the adjoining sides of the jaws 2215a, 2215b, which may or may not be fluidically coupled to the first, second, and third fluid paths 2223a-2223b.

Figure 10:
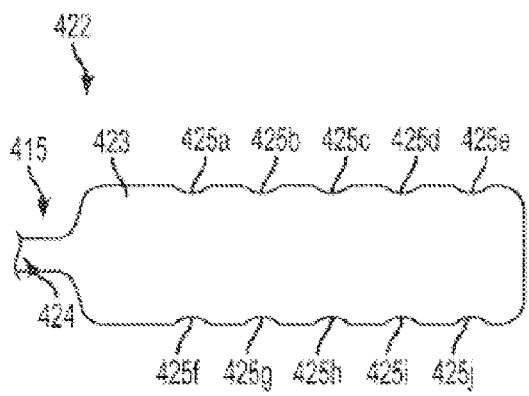
FIG. 10 illustrates a cross-section of one embodiment of a fluid path element of a fluid control system comprising one or more fluid paths integral to a jaw of an end effector.

FIG. 10 illustrates a cross-section of one embodiment of a fluid path element 422 of a fluid control system comprising one or more fluid paths integral to a jaw 415 of an end effector. One or more fluid paths 423 are defined, e.g., integrally formed, within a portion 415 of the end effector 413, such as a jaw 415 of a bi-polar device. A proximal end of the one or more fluid paths 423 comprises a proximal fluid port 424 configured to fluidically couple to fluid supply and transport system elements, which may be operatively coupled to an activation element, as described herein. The one or more fluid paths 423 further include one or more distal fluid ports 425a-425j positioned therealong to deliver or intake fluid.

Figure 11:
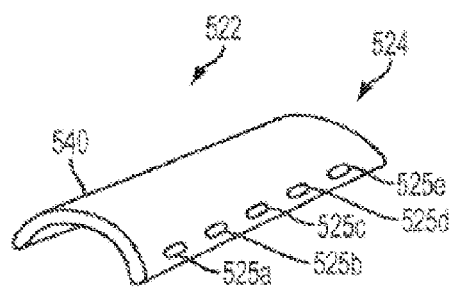
FIG. 11 illustrates one embodiment of a fluid path element of a fluid control system comprising one or more fluid paths.

FIG. 11 illustrates a configuration of a fluid path element 522 comprising a cover 540, which may be a mold or sleeve, which may comprise a rubber, polymer, or biocompatible material, e.g., thermoset or thermoplastic polymer, silica, silicone, neoprene, etc. The cover 540 is configured to be positioned on the end effector and comprises a proximal fluid port 524 configured to fluidically couple to a fluid supply and transport element, which may be operatively coupled to an activation element, as described herein. The cover 540 may define one or more fluid paths independently, e.g., define a cavity, bladder, or other hollow portion for fluid to travel, or in conjunction with a surface or portion of the end effector, e.g., a fluid path may be defined between the cover 540 and a surface of the end effector. The cover 540 further defines one or more distal fluid ports 525a-525e configured to deliver or intake fluid. While not visible, a corresponding side of the cover 540 may comprise similar features as those illustrated with respect to the visible side.

Figure 12:
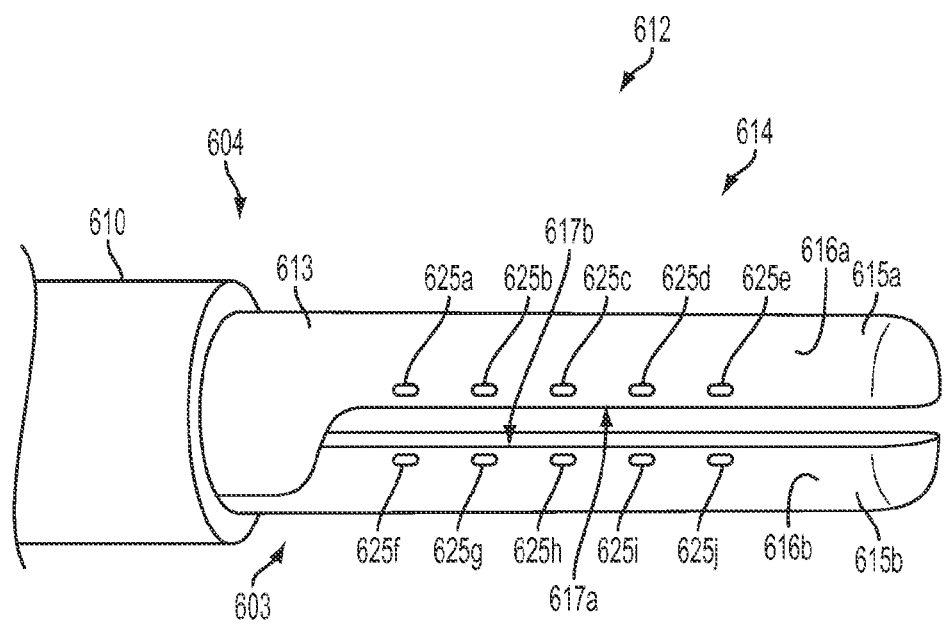
FIG. 12 illustrates a perspective view of one embodiment of a distal portion of an elongate member comprising a fluid control system.

FIG. 12 illustrates a distal portion 612 of an elongate member 604 of a medical device comprising a fluid control system 603 according to various embodiments. The elongate member 604 comprises a shaft 610 having a distal end 614 coupled to an end effector 613. The end effector comprises first and second jaws 615a, 615b configured to apply energy, e.g., bipolar energy, to tissue along working portions 617a, 617b. The fluid control system 603 comprises a fluid path element comprising one or more fluid paths, however, only corresponding distal fluid ports 625a-625j are visible in the perspective view shown. The one or more fluid paths may be configured internally to the first jaw 615a and second jaw 615b, as illustrated in FIG. 10, or may be defined by a cover, e.g., mold or sleeve, as illustrated in FIG. 11. Distal fluid ports 625a-625e may be coupled to the same or different fluid paths, which may be the same or different fluid paths 623b coupled to distal fluid ports 625f-625j. In various embodiments, combinations of the one or more fluid paths may be independent or fluidically coupled to a common fluid path element. Distal fluid ports 625a-625j are positioned adjacent to the distal portion 612 of the elongate member 604, e.g., along an outer portion or surface 616a, 616b of the end effector 613 or working portion thereof 617a, 617b. The distal fluid ports 625a-625j are positioned to deliver of fluid outwardly or away from the jaws 615a, 615b or to intake fluid, including steam or smoke, inwardly or toward the jaws 615a, 615b into the one or more fluid paths. As such, the distal fluid ports 625a-625j may be arranged in various configurations which may, for example, complement the configuration or operation of the end effector 613. In this way a fluid or vacuum may be provided proximate the regions where steam or smoke is likely to be generated or escape the jaws 615a, 615b. While not shown in FIG. 12, the fluid control system 603 may include similarly configured fluid paths and distal fluid ports on the adjoining sides of the jaws 615a, 615b.

Figure 13:
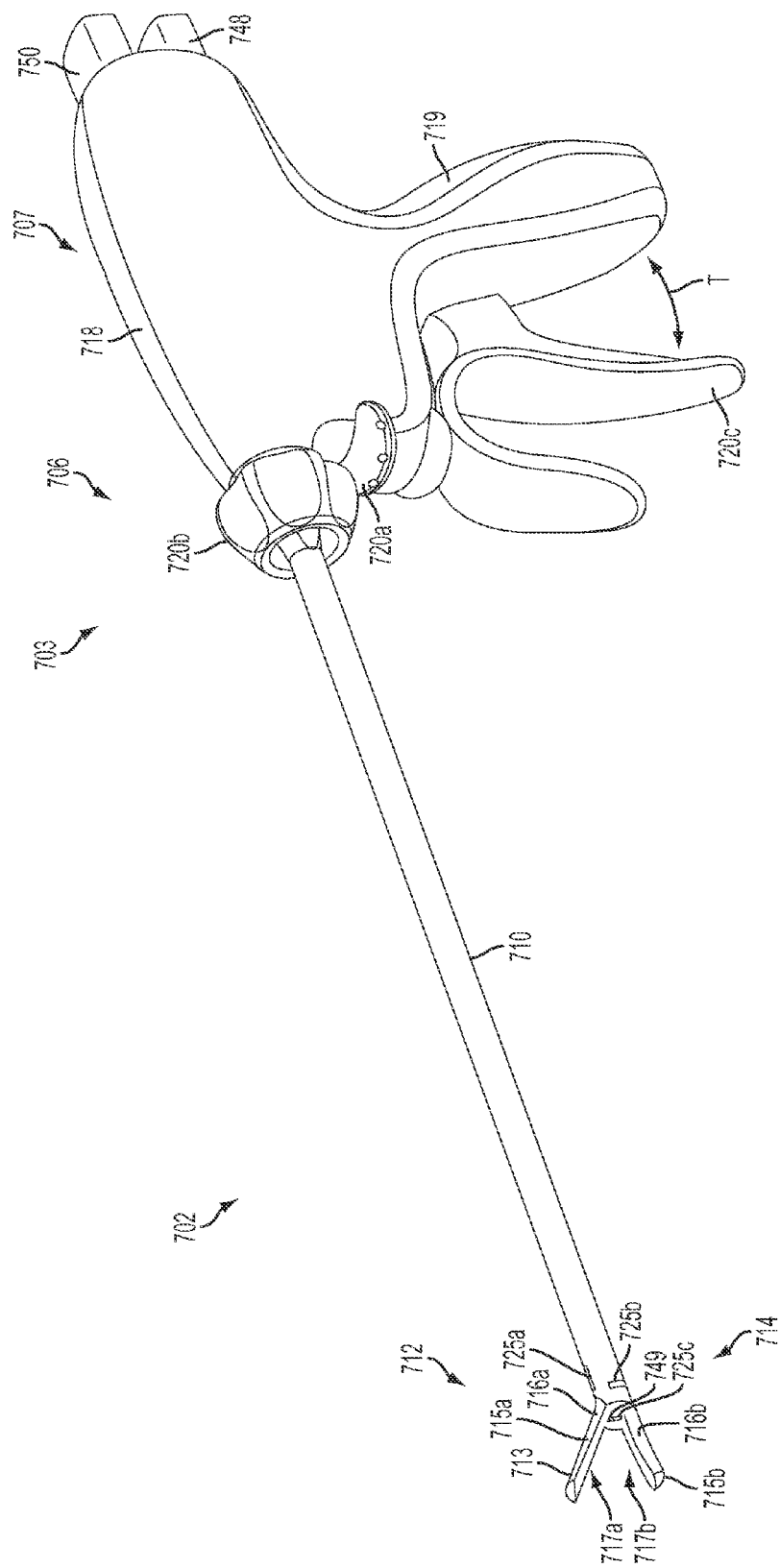
FIG. 13 illustrates a perspective view of one embodiment of a medical device including a fluid control system.

FIG. 13 illustrates a medical device 702 comprising a fluid control system 703 according to various embodiments. The medical device 702 comprises an elongate member 704 having a proximal portion 706 comprising a handle 707 that is coupled to a proximal end 709 of a shaft 710 and a distal portion 712 comprising an end effector 713 coupled to a distal end 714 of the shaft 710. The end effector 713 comprises a first jaw 715a and a second jaw 715b, each having an outer portion or surface 716a, 716b. In operation, tissue may be captured intermediate the jaws 715a, 715b and energy may be applied to the tissue along working portions 717a, 717b to treat, e.g., cook, target tissue. The handle 707 comprises a housing 718 defining a grip 719 and includes one or more control interfaces 720a-c, e.g., a switch 720a, rotation knob 720b, and a trigger 720c movable relative to the grip 719 along arrow "T", configured to provide operational instructions to the end effector 713. The handle 707 is further configured to electrically couple with a power source at fitting 748 to provide energy to the end effector 713. In other embodiments, however, handle 707 may include a power source in addition to or instead of fitting 748.

Although only the corresponding distal fluid ports 725a, 725b, 725c are visible in the perspective view shown in FIG. 13, the fluid control system 703 includes a fluid path element, which may be defined by lumens, lines, channels, voids, ducts, cavities, or tubing which may be externally or internally located within the medical device or integrally formed within the medical device. As previously described, the fluid control system 703 is fluidically coupled to the fluid path element, which is fluidically coupled to a fluid supply and transport element, which may be operatively coupled to an activation element, as described herein. For example, in this and other embodiments, a supply component comprising a fluid source or a reservoir, e.g., an environment to receive or exhaust fluid, may include or be fluidically coupled to a transport component. That is, the supply component may comprise an external environment to exhaust fluid, including steam or smoke, from the one or more fluid paths. The transport component may apply a negative pressure associated with the external environment, representing a pressure differential with the one or more fluid paths to provide a vacuum to pull the fluid. In another embodiment, the supply component may include a fluid supply comprising a transport component such as a pressurized tank containing a compressed fluid representing a pressure differential with a fluid path or external environment. The pressure differential may be exploited to move or transport the fluid, including steam or smoke, through the one or more fluid paths. As previously discussed, an activation element may be operatively coupled to initiate transport of fluid via operation of a valve or activation of the pump. In various embodiments, the pump may be positioned in the handle 707, shaft 710, or end effector 713, to push or pull fluid through the one or more fluid paths. For example, a user may provide a control or operation instruction to the transport component, e.g., via actuation of the trigger 720c or other control interface associated with the fluid control system. The control or operation instruction may send mechanical or electrical signals to activate or deactivate the fluid supply and transport element. For example, the control instruction may initiate an activation sequence that may be temporally or spatially varied with respect to the dimensions and operation of the end effector 713. As noted with other embodiments previously described, in various embodiments, the activation element may be coupled to activation of energy. The activation element may also comprise a mechanical activation mechanism such as a manual pump or a piston or plunger that is driven by the user to mechanically activate fluid path to transport fluid through the one or more fluid paths.

In the embodiment illustrated in FIG. 13, the handle 707 comprises a fitting 750 configured to fluidically couple to a fluid supply and transport element. For example, an external fluid source to provide fluid to the one or more fluid paths or a fluid reservoir into which steam or smoke may be exhausted. Similarly, the fitting 750 may be configured to couple to a pump to transport the fluid through the one or more fluid paths. The distal fluid ports 725a, 725b are positioned at a distal end 714 of the shaft 710 to deliver or intake fluid adjacent to the distal portion 712 of the elongate shaft. While the distal fluid ports 725*a*, 725*b* are shown as having outward oriented rectangular cross-sections that are flush with the shaft 710, in various embodiments the distal fluid ports 725*a*, 725*b* may be arranged and oriented in other configurations. Distal fluid port 725*c* is positioned between the first and second jaws 715*a*, 715*b* to deliver or intake fluid adjacent to the distal portion 712 of the elongate member 704.

The end effector 713 defines a channel fluidically coupled to one or more fluid paths extending along the shaft 710. In various embodiments, the channel may be a channel used exclusively as a fluid path or distal fluid port 725*a*, 725*b*, 725*c* or may be a channel used as a fluid path and distal fluid port 725*a*, 725*b*, 725*c* as well as having additional functions related to the operation of the end effector 713. For example, in FIG. 13, distal fluid port 725*c* is defined by a slot 749 configured to receive a cutting element, such as a knife or blade, for example, where the cutting element is movable within the slot 749 along the first and second jaws 715*a*, 715*b*. In various embodiments, the knife slot 749 may further extend distally along a channel extending through central portions of the end effector 713, which may comprise a fluid path comprising distal fluid ports positioned adjacent to the working portion 717*a*, 717*b* of the end effector 713. In one embodiment, the one or more fluid paths may be provided within the medical device or may be formed integrally therewith and are defined by lumens, lines, channels, voids, ducts, cavities, or tubing extending through the shaft 710 comprising a series of voids positioned between components of the shaft 710. In various embodiments where fluid paths are defined within channels, cavities, or voids of the handle, shaft, or end effector, covers, films, or coatings may be used to protect the components of the elongate member from damage caused by contact with moisture laden steam or smoke, for example, when the fluid control system 703 is configured to eject a liquid or mist or intake smoke or moisture within the one or more fluid paths at the one or more distal fluid ports 725*a*, 725*b*, 725*c*.

In one embodiment, the one or more fluid paths and corresponding fluid ports 725*a*, 725*b*, 725*c* may comprise multiple independent fluid paths that may be configured to fluidically couple to independent fluid sources. For example, a first fluid path element corresponds to a first fluid port, e.g., distal fluid port 725*a* or 725*b*, and a second fluid path element corresponds to a second fluid port, e.g., distal fluid port 725*c*. The first and second fluid paths may be independently defined and respectively coupled to first and second supply components, e.g., within handle 707 or through fitting 748. The first supply component may comprise a fluid source comprising fluid that may be transported through the first fluid path element and delivered to the surgical field adjacent the distal portion 712 of the elongate member 704. The second supply component may comprise a fluid reservoir configured to receive or exhaust fluid that is pulled from the surgical field, e.g., from between the first and second jaws 715*a*, 715*b* at the distal fluid port 725*c*, through the second fluid path element. As previously described, the fluid control system may include an activation element configured to provide selective activation for sequencing of the one or more operations of the fluid control system 703.

In various embodiments, referring to FIG. 14, a fluid control system 803 is shown that comprises a fluid path element wherein the shaft 810 comprises a cover 851 comprising a sleeve 852 defining one or more fluid paths, and corresponding distal fluid ports 825, which are visible in the perspective view shown. The illustrated embodiment shows a distal portion 812 of an elongate member 804 of a medical device. The elongate member 804 comprises a shaft 810 having a distal end 814 coupled to an end effector 813. The end effector 813 comprises first and second jaws 815*a*, 815*b* configured to apply energy, e.g., bipolar energy, along working portions 817*a*, 817*b*. The working portion 817*a*, 817*b* also includes a knife extendable along the jaws 815*a*, 815*b* through a slot 849*a*, 849*b* defined within a central region of the end effector 813 or jaws 815*a*, 815*b* The sleeve 852 defines a lumen 854 configured to receive or be positioned over a surface 856 of the shaft 810. For example, in one embodiment, the sleeve may be built into the shaft 810. In another embodiment, the sleeve 852 may be added to or optionally removed from the shaft 810 by sliding or positioning the sleeve 852 over the shaft 810. In various embodiments, the sleeve 852 may be formed of a biocompatible material. In one embodiment, the sleeve 852 comprises an elastomeric material such as a rubber, polymer, or biocompatible material, e.g., thermoset or thermoplastic polymer, silica, silicone, neoprene, etc. As an example, the sleeve 825 may be extruded or molded with fluid paths 825 defined therein. In various embodiments, the sleeve 852 may be configured to be thermally conductive, e.g., to assist in cooling the surgical field, or may be thermally insulative to prevent heat from the shaft 810 or end effector 813 from conducting to tissue.

The one or more fluid paths extend distally along the shaft 810 to one or more distal fluid ports 825 positioned adjacent the distal end 812 of the elongate member. While not shown, the one or more fluid paths may define proximal fluid ports fluidically coupled to a handle. The distal fluid ports 825 are positioned to deliver to or intake fluid from the surgical field. For example, FIG. 14 illustrates a steam or smoke control operation of the fluid control system 803. The steam or smoke control operation includes dispersing steam or smoke 45 within the surgical field. In this example, a gas is used as the fluid, however, other fluids may be used. The gas is delivered from the distal fluid ports 825 to produce a gas flow, as generally indicated by arrows G1, G2, and G3, distally toward the end effector 813. The gas flow may be delivered in a direction or at a rate or temperature configured to disperse, condense, or cool steam or smoke 45. The gas flow also may protect or cool tissue adjacent the target tissue. Notably, activation of the fluid control system 803 may be sequenced as previously described to occur at various times or locations during the operation of the end effector 813. Therefore, while the jaws 815*a*, 815*b* are illustrated in the open position, in various embodiments, the fluid control system 803 will be activated when the jaws 815*a*, 815*b* are closed and may not activate when the jaws 815*a*, 815*b* are open. Similarly, in various embodiments, the fluid control system 803 may be configured to intake steam or smoke into the one or more fluid paths 825 to clear the surgical field.

FIGS. 15A-15D illustrate cross-sectional views of fluid paths 822*a*-822*d* that include covers 851*a*-851*d* comprising sleeves 852*a*-852*d* having various configurations of fluid paths 823*a*-823*s* according to various embodiments. The sleeves 852*a*-852*d* may be similar to the sleeve 852 illustrated in FIG. 14 and FIGS. 16 and 17, described below. Each sleeve 852*a*-852*d* defines a lumen 854*a*-854*d* configured to receive or be positioned on a surface of a shaft such that the sleeve 852*a*-852*d* may be positionable along an elongate member. Each sleeve 852*a*-852*d* further defines one or more fluid paths 823*a*-823*s* that extend along a portion of its length.

Figure 15A:
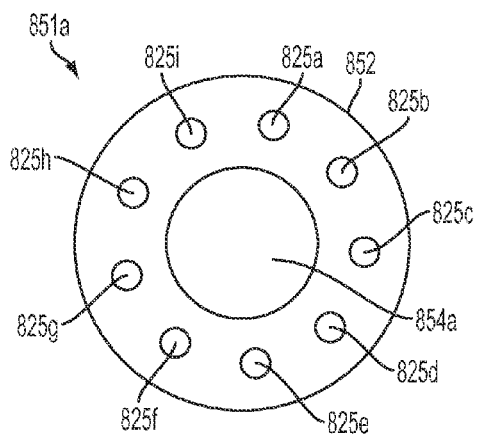
Figure 15C:
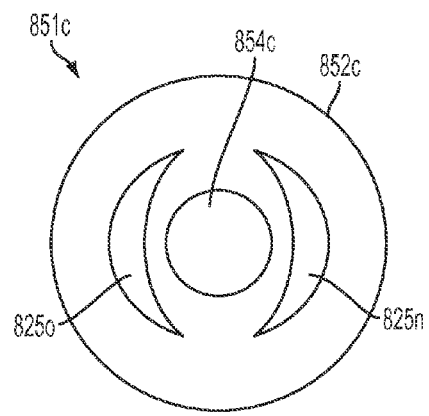
Figure 15B:
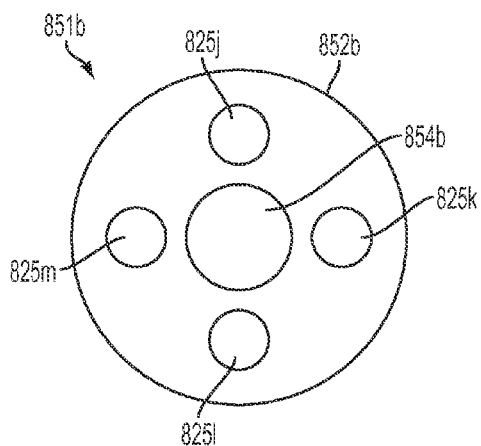
Figure 15D:
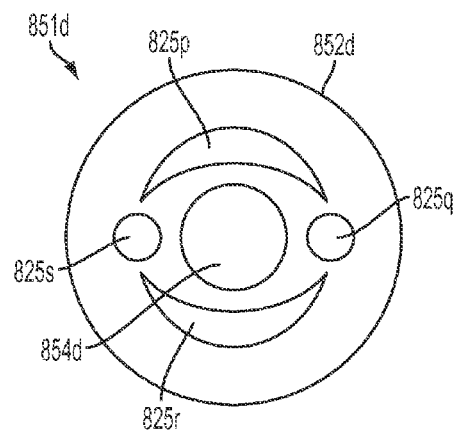

In FIG. 15A the sleeve 852*a* defines a plurality of fluid paths 823*a*-823*i* having generally circular cross-sections.

The fluid paths 823a-823i are arranged about a circumference or perimeter of the sleeve 852a and are spaced apart at similar intervals. As introduced above, the number, position, arrangement, and cross-sectional size and shape of the one or more fluid paths may vary, e.g. in consideration of the fluid transported or operation or dimensions of an end effector. The sleeve 852b illustrated in FIG. 15B defines four fluid paths 823j-823m having generally arcuate cross-sections arranged about the circumference sleeve. The cross-sectional area of each fluid path element 823j-823m is larger than the cross-sectional area of each of the fluid paths 823a-823d defined by the sleeve 852a. For example, the fluid paths 823j-823m may be configured to transport an increased volume of fluid through each of the fluid paths 823j-823m. It is to be appreciated that one or more of the fluid paths 823a-823s may similarly merge or branch out to define fewer or additional fluid paths having larger or reduced volumes along a portion of the length of the sleeve 852a-852d. The sleeve 852c illustrated in FIG. 15C defines two fluid paths 823n, 823o. The fluid paths 823n, 823o comprise arcuate or crescent cross-sections arranged about the circumference or perimeter of the sleeve 852c. The cross-sectional area of the fluid paths 823n, 823o may be larger than the cross-sectional areas of the fluid paths 823a-823m. In various embodiments, sleeves may define one or more first fluid paths defining a first cross-sectional shape and area and one or more second fluid paths defining a second cross-sectional shape and area. For example, the sleeve 852d illustrated in FIG. 15D defines two generally opposed first fluid paths 823p, 823r comprising arcuate crescent shaped cross-sections having a first cross-sectional area and two generally opposed second fluid paths 823q, 823s comprising arcuate circular cross-sections having a second cross-sectional area different than the first. As previously described, one or more fluid paths may be independent, e.g., comprise separate fluid paths extending from a proximal fluid port to a distal fluid port. While not shown, in certain embodiments, multiple fluid ports may be stacked along a radius of the sleeve. It is to be appreciated that sleeves may also comprise regular or irregular cross-sections, which may correspond to an arrangement of fluid paths, a dimension of an end effector, or an operation of an end effector.

Figure 16:
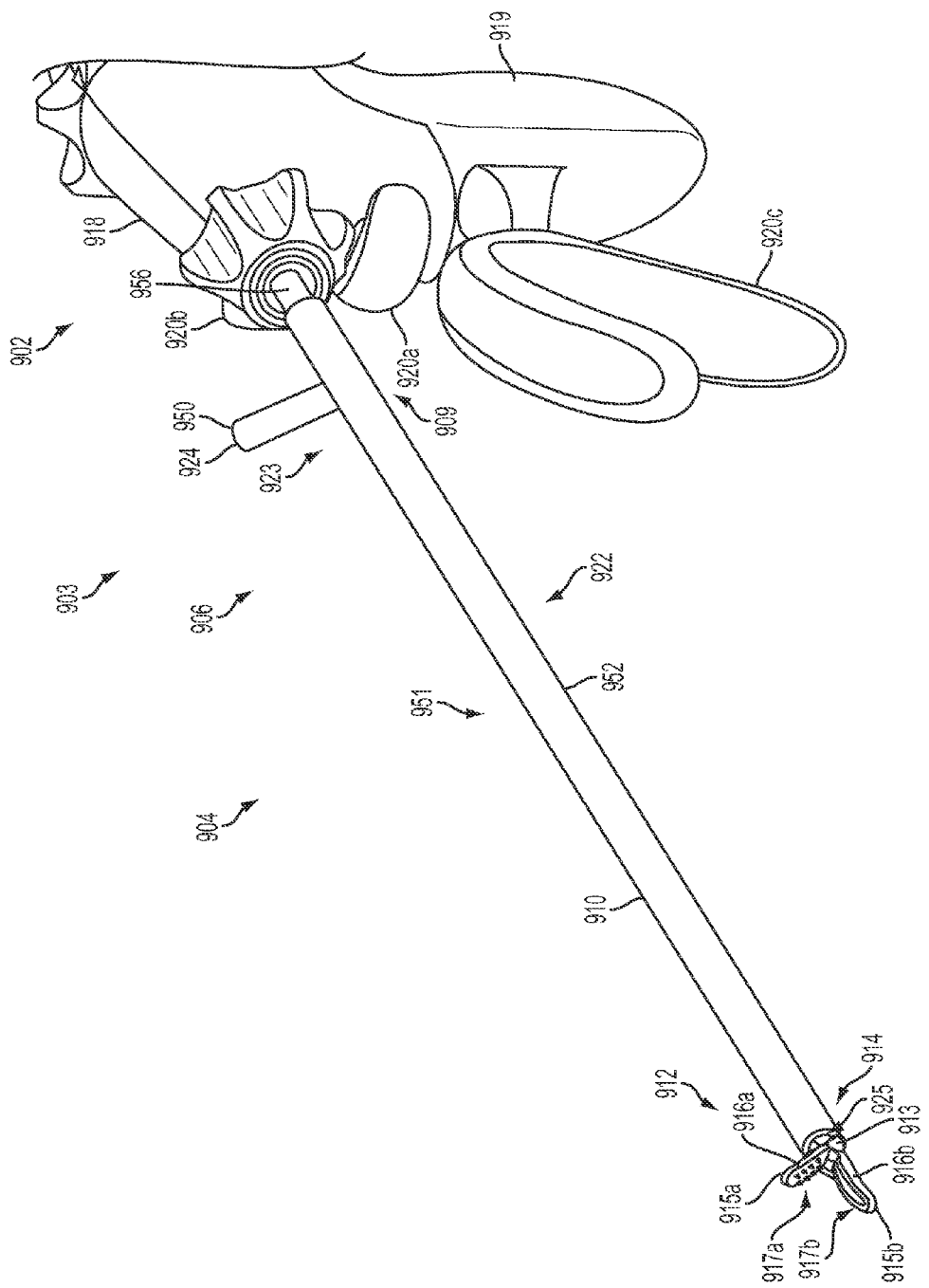
FIG. 16 illustrates one embodiment of a medical device including a fluid control system.
Figure 17:
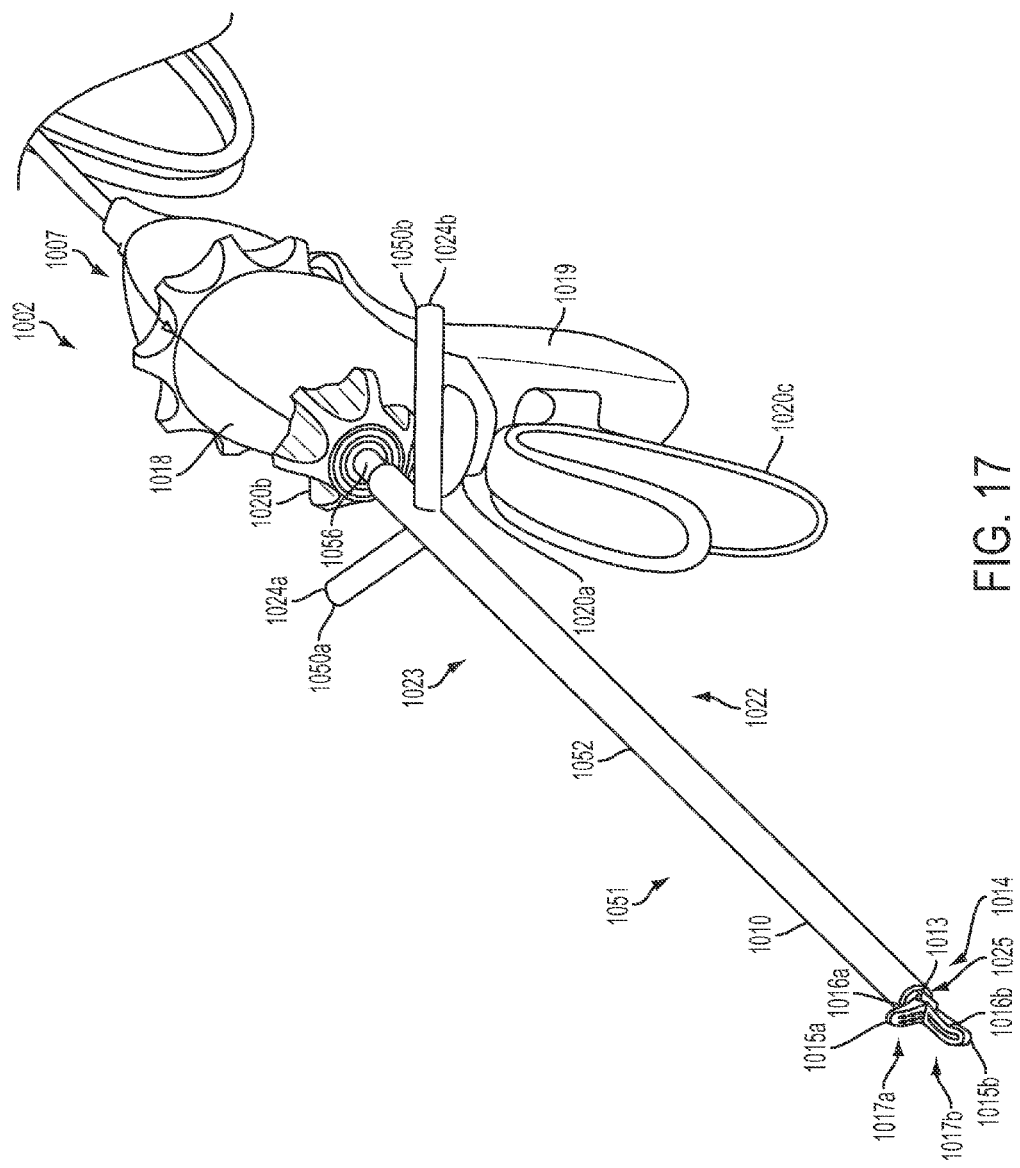
FIG. 17 illustrates one embodiment of a medical device including a fluid control system.

FIGS. 16 and 17 illustrate two embodiments of medical devices 902, 1002 comprising fluid control systems 903, 1003. The medical devices 902, 1002 comprise elongate members 904, 1004 comprising fluid control systems 903, 1003 according to various embodiments. Features of the handle 907, 1007 and end effector 913, 1013 may be similar in general structure or concept to features previously described with respect to other embodiments and, therefore, have been identified with like numbers and will not be described again. The fluid control systems 903, 1003 of the illustrated embodiments comprise fluid path elements 922, 1022 including covers 951, 1051 comprising sleeves 952, 1052. In particular, the sleeves 952, 1052 define one or more fluid paths 923, 1023 defining one or more proximal fluid ports 924, 1024a, 1024b and one or more distal fluid ports 925, 1025. The one or more distal fluid ports 925, 1025 may be similar to those previously described with respect to FIGS. 14-15. The one or more proximal fluid ports 924, 1024a, 1024b may comprise one or more fittings 950, 1050a, 1050b extending from the sleeve 952, 1052. The fittings 950, 1050a, 1050b are configured to fluidically couple to fluid supply and transport elements, which may be associated with an activation element, as described herein. For example, the sleeve 952 illustrated in FIG. 16 comprises a proximal fluid port 924 configured to fluidically couple to a supply component, e.g., an external fluid source or fluid reservoir configured to evacuate or exhaust fluid. In one such embodiment, the proximal fluid port 924 comprises fitting 950 configured to couple to an insufflation gas source. In operation, activation of the insufflation gas source by the activation element, e.g., via a control signal initiated by the user, provides gas to the one or more fluid paths 923 that is transported distally to the one or more distal fluid ports 925 to mitigate steam or smoke damage to adjacent tissue. The sleeve 1052 illustrated in FIG. 17 comprises two proximal fluid ports 1024a, 1024b, each configured to fluidically couple to a supply component, e.g., an external fluid source or fluid reservoir configured to evacuate or exhaust fluid. In one such embodiment, the first proximal fluid port 1024a comprises fitting 1050a configured to couple to an insufflation gas source and the second proximal fluid port 1024b comprises a fitting 1050b configured to couple to an additional fluid source, e.g., source for liquid saline. As previously described, the one or more fluid paths 923, 1023 may be independent or coupled. In operation, fluid such as a gas, liquid, or mist may be supplied to one or more fluid paths 923, 1023 and delivered to the surgical field at one or more distal fluid ports 925, 1025 positioned adjacent to the distal portion of the elongate member 904, 1004. The end effector 913, 1013 may be surrounded by the fluid, e.g., enveloped within a fluid layer. For example, the fluid paths 923, 1023 may be provided with a liquid that is ejected from the sleeve 952, 1052 at one or more distal fluid ports 925, 1025 to provide a liquid wall or tube around the end effector 913, 1013. In one embodiment, negative pressure or vacuum may be provided by a transport component, which may be fluidically coupled to the supply component, such that a vacuum applied around the end effector 913, 1013 to intake steam or smoke adjacent to the distal portion of the elongate member 904, 1004. In various embodiments, the shaft 910, 1010 may further comprise a seal positioned between surface 956, 1056 that underlies the sleeve 952, 1052 and a surface of the sleeve 952, 1052, e.g., the inner circumference of a lumen similar to lumens 854-854d, to prevent fluid from leaking from the sleeve 952, 1052. For example, an o-ring or sealant may be positioned between the surface 826 and the inner circumference or beneath a proximal portion of the sleeve 952, 1052.

Figure 18:
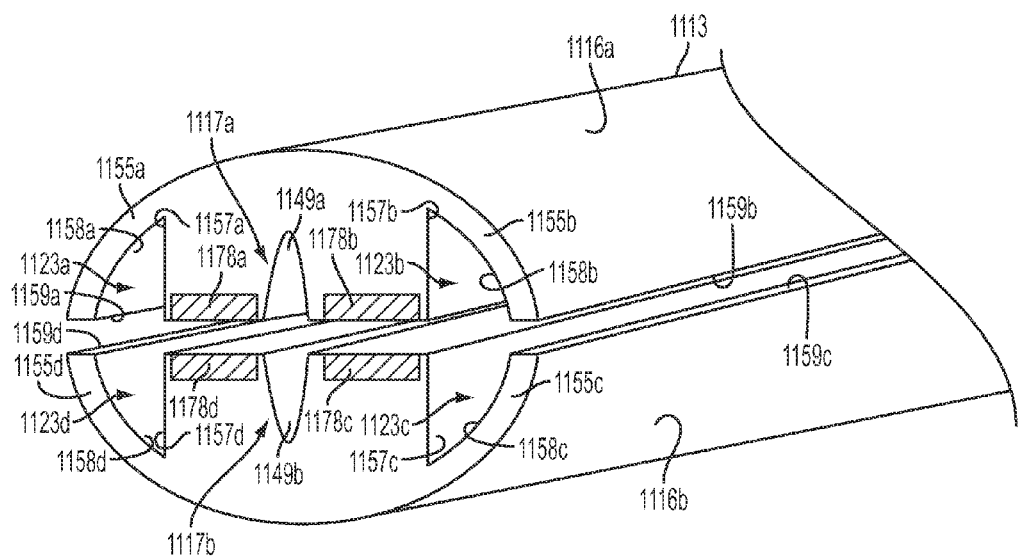
FIG. 18 illustrates a perspective view in cross-section of one embodiment of one or more fluid paths extending along an end effector.

In various embodiments, a fluid control system includes a fluid path element comprising one or more fluid paths internal to or at least partially defined by the end effector, e.g., as illustrated in FIGS. 10, 12, and 13. FIG. 18 illustrates another embodiment of a fluid path element comprising one or more fluid paths integral to or defined within an end effector. Specifically, FIG. 18 illustrates a perspective view in cross-section of an end effector 1113 defining one or more fluid paths 1123a-1123d for use as a fluid path element of a fluid control system according to various embodiments. The end effector 1113 comprises a first jaw 1115a and a second jaw 1115b having outer portions or surfaces of the 1116a, 1116b and working portions 1117a, 1117b. Working portions 1117a, 1117b are illustrated as including electrodes 1178a-1178d and knife slot 1149a, 1149b. Extensions 1155a-1155d of outer portions or surfaces 1116a, 1116b, which may comprise a cover positioned on the end effector 1113, extend outward of the end effector 1113 to form a channel or cavity defining one or more fluid paths 1123a-1123d adjacent to the working portions 1117a extending along a perimeter of the jaws 1115a, 1115b. The extensions 1155a-1155d may be visualized as an umbrella positioned around the working portions 1117a, 1117b of the end effector 1113. Notably, in one embodiment, fluid paths 1123*a*, 1123*b* or 1123*c*, 1123*d* extend along the perimeter of the jaw 1115*a* and form a single fluid path element. As shown, the one or more fluid paths 1123*a*-1123*d* are at least partially defined by respective surfaces 1157*a*-1157*d*, 1158*a*-11158*d*. In certain embodiments, the extensions 1155*a*-1155*b* may comprise tissue contact surfaces 1159*a*-1159*d* configured to compress and thereby seal the tissue. The contact surfaces 1159*a*-1159*d* may be aligned or offset toward an opposed jaw 1115*a*, 1115*b*. For example, the contact surfaces 1159*a*-1159*d* may extend beyond the accompanying surfaces of the jaw 1115*a*, 1115*b* configured to contract tissue. Still in other embodiments, the contact surfaces 1159*a*-1159*b* may be configured to allow fluid external to the jaws 1115*a*, 1115*b* to be suctioned into the fluid paths 1123*a*-1123*d* or fluid delivered through the fluid path 1123*a*-1123*d* to be directed from the fluid paths 1123*a*-1123*d* to the surgical field external to the jaws 1115*a*, 1115*b*, e.g., between tissue and contact surfaces 1159*a*-1159*d*. In operation, steam or smoke may be produced when energy is applied to target tissue positioned intermediate the first and second jaws 1115*a*, 1115*b*. As such, the steam or smoke will enter the one or more fluid paths 1123*a*-1123*d* at distal fluid ports 1125*a*-1125*d*. The steam or smoke may be retained or captured within the jaws 1115*a*, 1115*b*. In various embodiments, a vacuum may be applied to suction the steam or smoke proximally. In other embodiments, a fluid may be supplied for circulation within the fluid paths 1123*a*-1123*d* to disperse, condense steam, or otherwise suction or cool the steam or smoke. For example, liquid may be circulated through the one or more fluid paths 1123*a*-1123*b* to protect adjacent tissue. Notably, the fluid paths 1123*a*-1123*d* may be configured to fluidically couple to one more fluid paths extending down a shaft of a medical device, e.g., via an intermediate fluid port, as described herein or be directed to exhaust actively or passively from one or more proximal fluid ports, e.g., fluid ports positioned on the outer portion of surface 1116*a*, 1116*b* of the end effector 1113, cover, or shaft for controlled or predictable release, as described below. In various embodiments, a slot 1149*a*, 1149*b* configured to slidably receive a cutting element, such as a knife or blade, for example, may be configured for use as a fluid path or fluid port. For example, a channel extending along a central portion of the end effector 1113 may be configured for translation of a knife as well as a fluid path adjacent to the working portion 1117*a*, 1117*b* of the end effector 1113. It is to be appreciated that the respective outer portions or surfaces 1116*a*, 1116*b* of the first and second jaws 1115*a*, 1115*b* may include a cover, such as a sleeve or mold, e.g., overmolding, positioned on the end effector 1113 to form the channel or cavity defining the one or more fluid paths 1123*a*-1123*d*.

Figure 19:
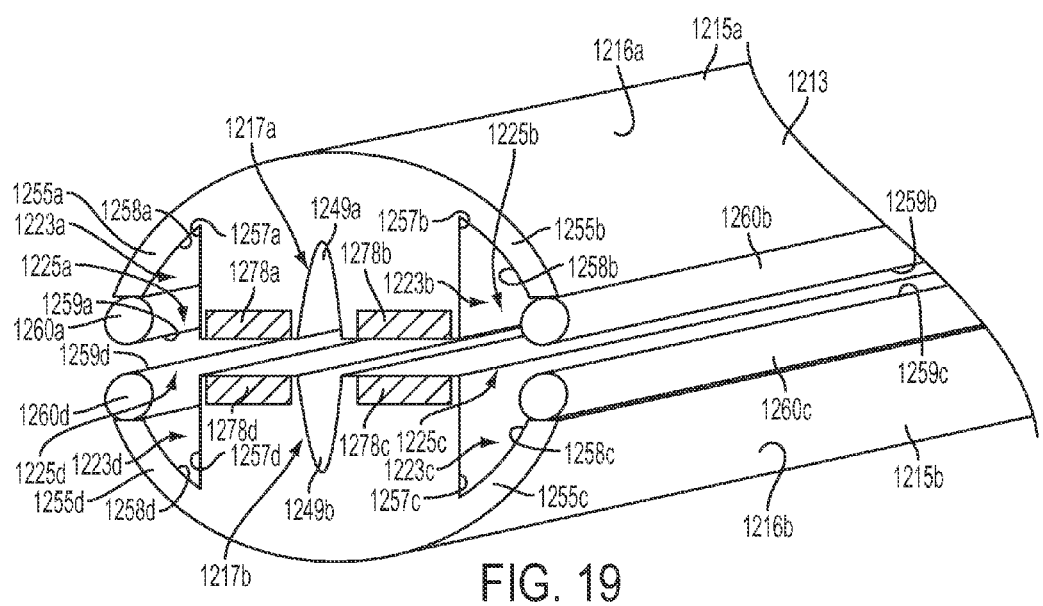
FIG. 19 illustrates a perspective view in cross-section of one embodiment of one or more fluid paths and gaskets extending along an end effector.

FIG. 19 illustrates a perspective view in cross-section of an end 1213 defining one or more fluid paths 1223*a*-1223*d* for use as a fluid path element of a fluid control system according to various embodiments. The end effector 1213 comprises a first jaw 1215*a* and a second jaw 1215*b*. Similar to FIG. 18, outer portions or surfaces 1216*a*, 1216*b* of the jaws 1215*a*, 1215*b* comprise extensions 1255*a*-1255*d* extending outwardly from working portions 1217*a*, 1217*b* of the end effector 1213 to form a channel or cavity defining one or more fluid paths 1223*a*-1223*d* that may extend around the end effector 1213. In operation, steam or smoke may be produced when energy, e.g., bipolar energy at electrodes 1278*a*-1278*d*, is applied to target tissue positioned intermediate the first and second jaws 1215*a*, 1215*b*. As such, the steam or smoke may enter the one or more fluid paths 1223*a*-1223*d* at distal fluid ports 1225*a*-1225*d* and thereby be retained or captured within the jaws 1215*a*, 1215*b*. In certain embodiments, a supply component may supply fluid that is transported by a transport component as described herein. For example, fluid may be circulated through one or more fluid paths 1223*a*-1223*d* to circulate, exhaust, cool, condense, or disperse the steam or smoke or cool adjacent tissue.

In one embodiment, the end effector 1213 may differ from the end effector 1113 illustrated in FIG. 18 in that the extensions 1255*a*-1255*d* comprise gaskets 1260*a*-1260*d* positioned around a perimeter of the jaws 1215*a*, 1215*b*. The gaskets 1260*a*-1260*b* have contact surfaces 1259*d*-1259*d* that may be aligned or offset from a jaw 1215*a*, 1215*b*. For example, the contact surfaces 1259*a*-1259*d* of the gaskets may be aligned with or offset, e.g., recessed or protruding, from adjacent surfaces of the jaws 1215*a*, 1215*b* configured to contract tissue. In various embodiments, the gaskets 1260*a*-1260*d* are configured to at least partially define the one or more fluid paths 1223*a*-1223*d* in combination with respective surfaces 1257*a*-1258*d*. As such, the gaskets 1260*a*-1260*b* may extend along a perimeter of the end effector 1213 and may be positioned at outer portions or surfaces 1216*a*, 1216*b* of the jaws 1215*a*, 1215*b* or may extend outwardly from the working portion 1217*a*, 1217*b*, e.g., along electrodes 1278*a*-1278*d* or knife slot 1249*a*, 1249*b*, to define a channel or internal region therein configured to function as a fluid path 1223*a*-1223*d* having a distal fluid port 1225*a*-1225*d*. As such, gaskets 1260*a*-1260*d* may be aligned or offset toward an opposing jaw 1215*a*, 1215*b* and define an internal region therein in conjunction with extensions 1255*a*-1255*d*. In various embodiments, the gaskets 1260*a*-1260*d* are configured to compress tissue therebetween at contract surfaces 1259*a*-1259*d* upon application of a minimum force to form a soft or gentle seal. In the illustrated embodiment, when energy is applied to target tissue between the jaws 1215*a*, 1215*b*, the gaskets 1260*a*-1260*d* prevent steam or smoke that may damage adjacent tissue from escaping the jaws 1215*a*, 1215*b*. For example, steam or smoke enters the one or more fluid paths 1223*a*-1223*d* at distal fluid ports 1225*a*-1225*d* where it may be transported or circulated, e.g., with an additional fluid, by the fluid control system. As previously described, the extensions 1255*a*-1255*d* or outer portion or surface 1216*a*, 1216*b* of the first and second jaws 1215*a*, 1215*b* may comprise a cover or overmold positioned over the end effector that may include gaskets 1260*a*-1260*d*.

In certain embodiments, the gaskets 1260*a*-1260*d* may comprise a fitting that includes a dimension for attachment to the end effector 1213. For example, a fitting may comprise a complementary dimension to snap the gasket 1260*a*-1260*d* into place or a clamping layer configured to be attached, e.g., by an adhesive, screw, rivet, or other fastener, or clamped between components of the end effector. In various embodiments, the gaskets 1260*a*-1260*b* may be pliable or otherwise configured to be fittably positioned on the end effector 1213 or shaft. For example, the gaskets 1260*a*-1260*d* may comprise an elastomeric material such as a rubber, polymer, or biocompatible material, e.g., thermoset or thermoplastic polymer, silica, silicone, neoprene, etc., that may be configured to seal and/or absorb steam. The gasket material may be an impenetrable material that acts as a true barrier. Alternatively, the gasket material may possess absorption properties that prevent steam from passing through the gaskets 1260*a*-1260*d*. The gaskets 1260*a*-1260*d* may cool or thermally filter the steam or smoke such that steam or fluid passing from the fluid path 1223*a*-1223*d* of the jaws 1215a, 1215b will not be passed to the surrounding environment external to the jaws 1215a, 1215b until the steam is sufficiently cool as to be condensed or otherwise reduce the potential for blanching of adjacent tissue.

During activation of the device, a vacuum or negative pressure may be applied to one or more fluid paths 1223a-1223d as previously described. In the illustrated embodiment, the end effector 1213 comprises fluid paths 1223a-1223d extending along respective channels formed by a slot configured to slidably receive a blade or cutting element, for example. When a vacuum or negative pressure is applied to the one or more fluid paths 1223a-1223d internal to the jaws 1215a, 1215b steam or smoke created from the application of energy may be evacuated via the fluid control system. For example, a vacuum may be applied to suction the steam or smoke proximally. In other embodiments, a fluid may be supplied for circulation within the fluid path to disperse or condense steam. For example, liquid may be circulated through the one or more fluid paths 1223a-1223d to protect adjacent tissue. In an alternate embodiment, a pressure differential is not applied to the fluid path and the steam or smoke is allowed to passively exhaust from a proximal fluid port in a controlled or predictable manner.

Figure 20:
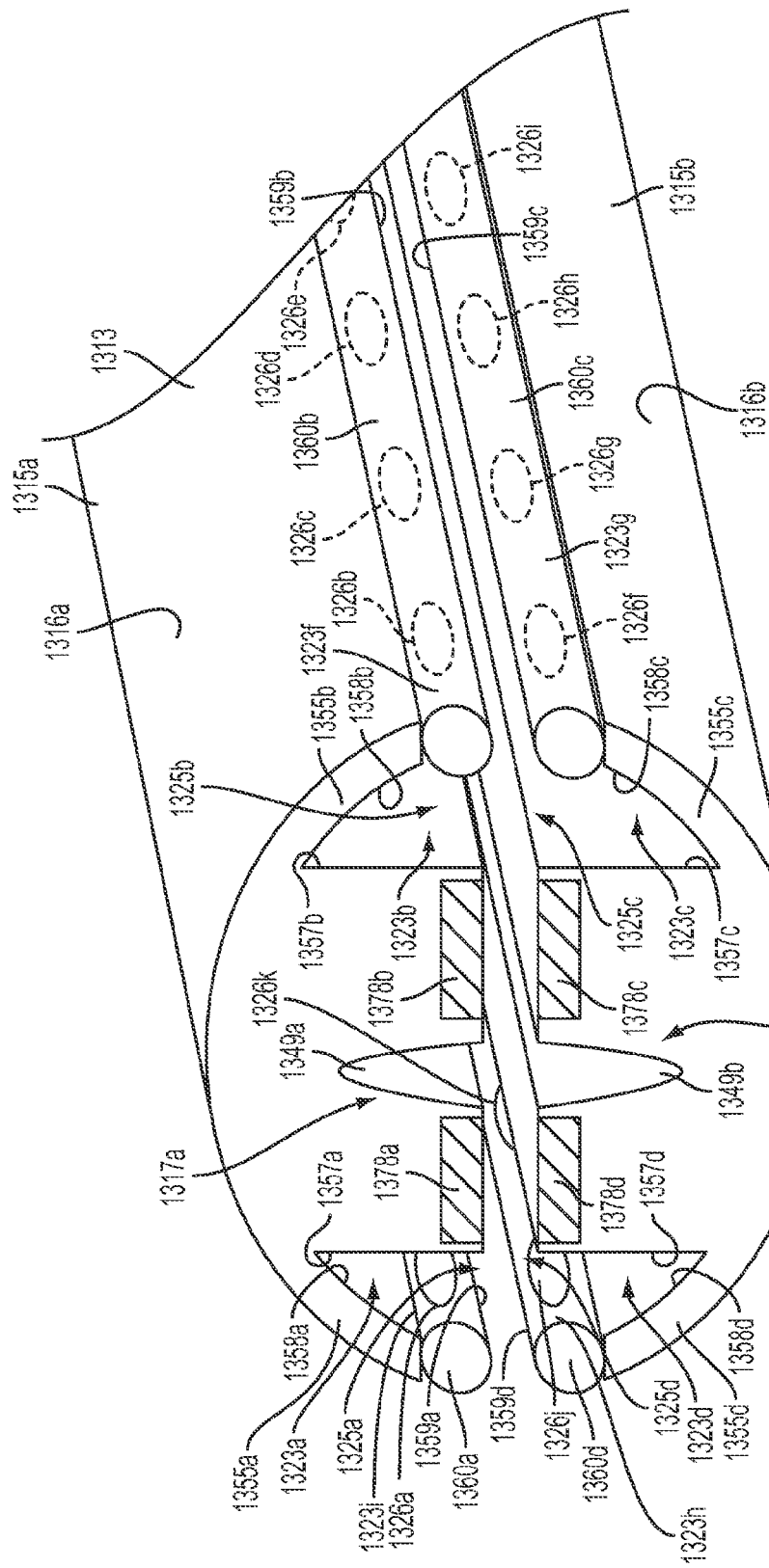
FIG. 20 illustrates a perspective view in cross-section of one embodiment of one or more fluid paths and gaskets extending along an end effector.

FIG. 20 illustrates an alternate embodiment of FIG. 19 wherein gaskets 1360a-1360d define one or more second fluid paths 1323e-1323h within a lumen extending within the gasket 1360a-1360d. For example, the one or more first fluid paths 1323a-1323d are fluidically coupled to the one or more second fluid paths 1323e-1323h via intermediate fluid ports 1326a-1326k when the gaskets 1360a-1360d compress tissue between contact surfaces 1359a-1359d. As such, the intermediate fluid ports 1327a-1327i may defined on a surface defining the first fluid path and be positioned to open to the internal region between the jaws 1315a, 1315b or into the first fluid path to deliver, intake, or circulate fluid with the one or more fluid paths 1323a-1323d to protect adjacent tissue. In one embodiment, the fluid path element depicted in the embodiment illustrated in FIG. 9 may include a gasket. Thus, in various embodiments, fluid ports may be positioned inward or outward of the end effector.

Figure 21:
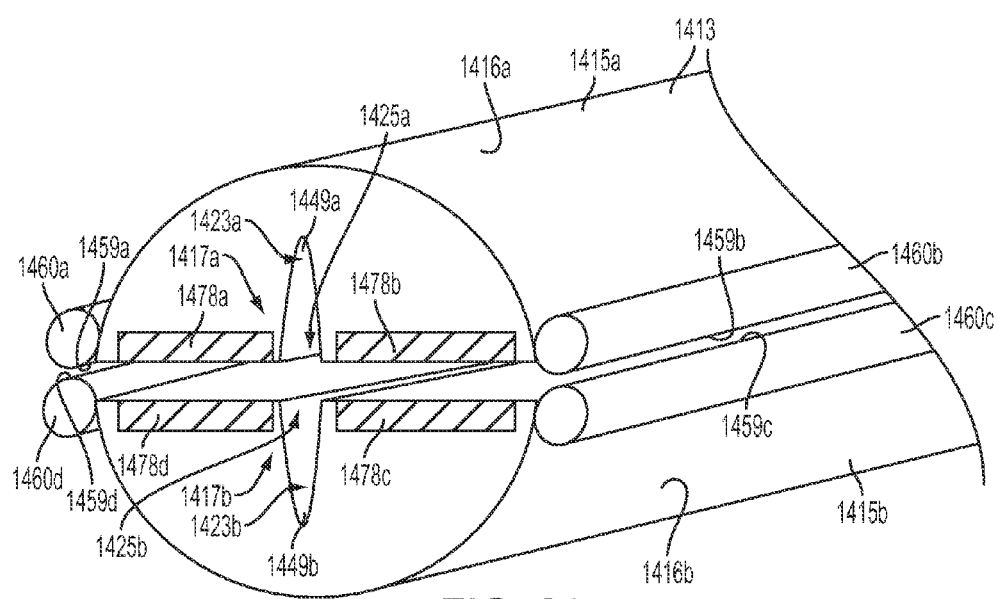
FIG. 21 illustrates a perspective view in cross-section of one embodiment of one or more fluid paths and gaskets extending along an end effector.

FIG. 21 illustrates a cross-section of an end effector 1413 defining one or more fluid paths 1423a, 1423b for use as a fluid path element of a fluid control system according to various embodiments. Similar to the embodiments illustrated in FIGS. 19 and 20, gaskets 1460a-1460d are positioned at outer portions or surfaces 1416a, 1416b along perimeters of the first and second jaw 1415a, 1415b. The end effector 1413, however, does not include the one or more channels or cavities positioned around the outer surface or perimeter portion of the jaws 1415a, 1415b to define one or more fluid paths, rather a channel or cavity is defined within a central portion of the end effector 1413. For example, first and second jaws 1415a, 1415b define channels or cavities within knife slot 1149a, 1449b defining one or more fluid paths 1423a, 1423b. The gaskets 1460a-11460d are aligned or offset toward an opposing jaw 1415a, 1415b from the components of the first and second jaw 1415a, 1415b such that the gaskets 1460a-1460d may contact and thereby provide a seal with tissue at contact surfaces 1459a-1459d adjacent to the working portions 1417a, 1417b when the first and second jaws 1415a, 1415b are in a closed position. Consequently, steam or smoke within the jaws 1415a, 1415b will be captured or retained within the one or more fluid paths 1423a, 1423b through distal fluid ports 1425a, 1425b. As previously described, the one or more fluid paths 1423a, 1423b may be fluidically coupled to fluid supply and transport elements to exhaust or circulate fluid within the one or more fluid paths 1423a, 1423b.

Figure 22A:
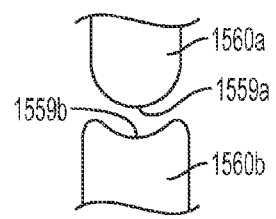
FIGS. 22A-22F illustrate cross-sections of various embodiments of gaskets.
Figure 22B:
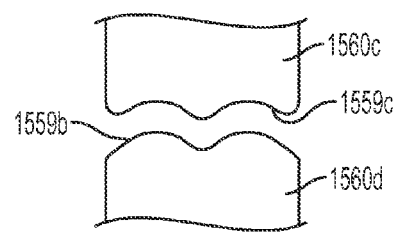
Figure 22C:
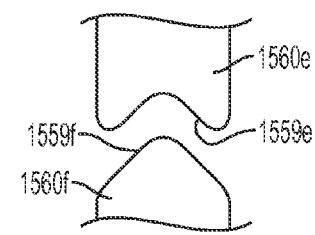
Figure 22D:
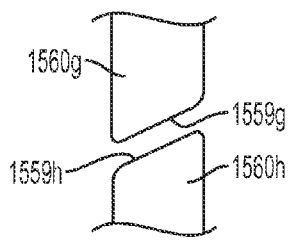
Figure 22E:
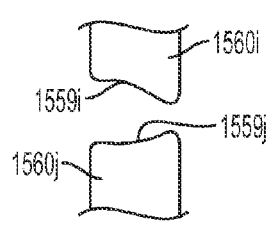
Figure 22F:
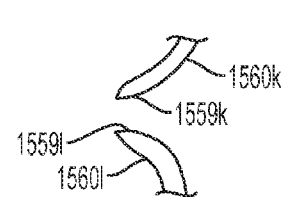

According to various embodiments, referring to FIGS. 22A-22F, gaskets 1560a-1560l may comprise one or more dimension configured to compress or form a seal with tissue positioned between contact surfaces 1559a-15591. The gaskets 1560a-1560l, for example, may be dimensioned to increase surface interaction with tissue compressed therebetween or present a tortuous path for fluid, steam, or smoke to ingress or egress between the regions internal and external to the jaws. FIGS. 22A-22C illustrate gaskets 1560a-1560h comprising contact surfaces 1559a-1559h that comprise complementary dimensions. When tissue is compressed between the contact surfaces 1559a-1159h, a tortuous path is created between tissue and the contact surface 1559a-1559h thereby improving the sealing interaction between the gaskets 1560a-1560h and the tissue with minimal compression force. FIG. 22D illustrates gaskets 1560i, 1560j with contact surfaces 1559i, 1559j presenting dimensions that increase compression at one or more points of contact. For example, greater contact or compression with tissue may be applied closer to the target tissue which may be cauterized while less contact may be applied to tissue positioned a greater distance from the target tissue which may retain fluid content. FIG. 22F illustrates gaskets 1560k, 1560l comprising contact surfaces 1559k, 15591 that increase contact area with increasing proximity. For example, gaskets 1560k, 1560l may be similar to duckbill gaskets configured to apply a soft seal with tissue.

Figure 23:
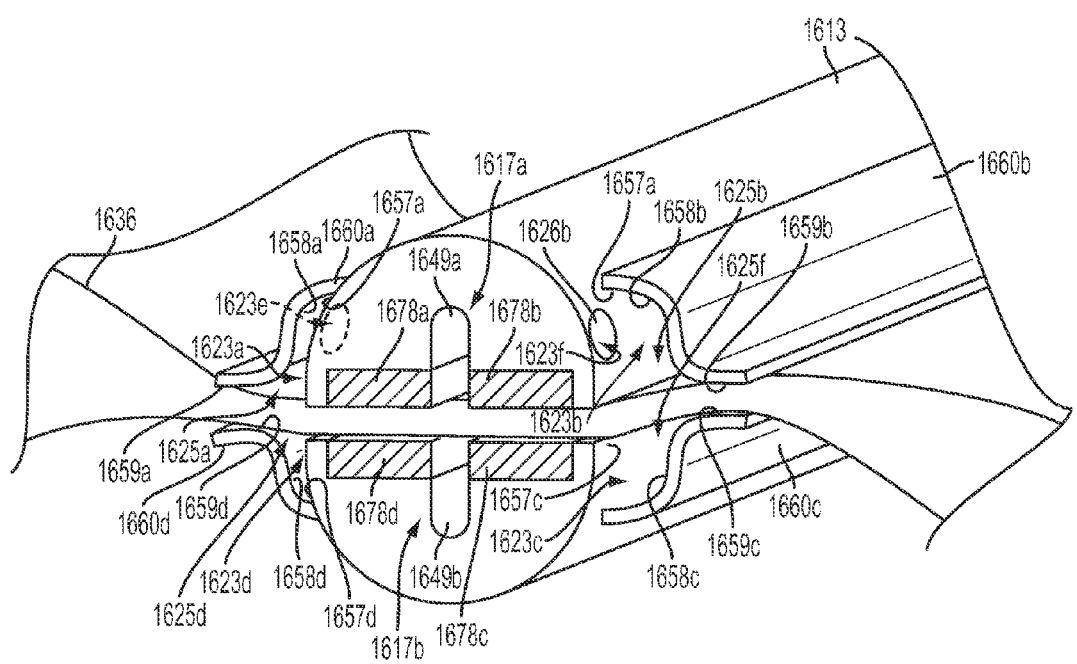
FIG. 23 illustrates a perspective view in cross-section of one embodiment of one or more fluid paths and gaskets extending along an end effector wherein tissue is positioned between the first and second jaw of an end effector.

FIG. 23 illustrates a cross-section of an end effector 1613 defining one or more fluid paths 1623a-1623f for use as a fluid path element of a fluid control system according to various embodiments. The embodiment may be similar to the embodiment illustrated in FIG. 12 that is fitted with extensions or a cover comprising gaskets 1660a-1660d having contact surfaces 1659a-1659d configured to form a seal with tissue 1636. The gaskets 1660a-1660d may be positioned around a perimeter or periphery of the jaws 1615a, 1615b to form a retention seal or barrier to prevent steam or smoke from damaging adjacent tissue. In particular, the gaskets 1660a-1660d may form a duckbill interaction with tissue 1636 and form a channel in combination with another surface. For example, first fluid paths 1623a-1623d are at least partially defined by respective surfaces 1657a-1657d of the jaws 1615a-1615d and surfaces 1658a-1658d of the gaskets 1660a-1660d to define one or more fluid paths 1623a-1623d configured to capture or retain steam or smoke through distal fluid ports 1625a-1625d produced from the action of the working portions 1617a, 1617b, e.g., application of energy at electrodes 1678a-1678d. The first jaw 1615a defines one or more second fluid paths 1623e, 1623f having one or more intermediate fluid ports 1626a, 1626b positioned to deliver fluid or intake smoke, steam, or other fluid. It is to be appreciated that in various embodiments, the second jaw 1615b may similarly define one or more second fluid paths and intermediate fluid ports similar to the first jaw 1615b. In certain embodiments, one or more of the fluid paths 1623a-1623e may be independent or may fluidically couple to additional fluid paths or one or more fluid supply or transport components as previously described.

Figure 24:
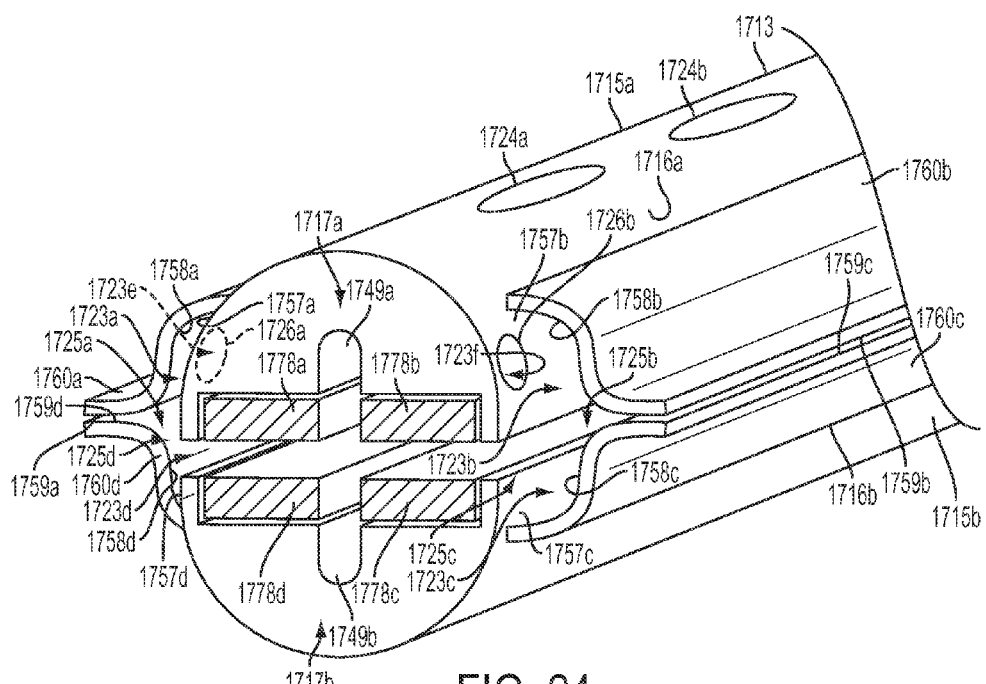
FIG. 24 illustrates a perspective view in cross-section of one embodiment of one or more fluid paths and gaskets extending along an end effector.

FIG. 24 illustrates a cross-section of an end effector 1713 defining one or more fluid paths 1723a-1723f for use as a fluid path element of a fluid control system according to various embodiments. The embodiment may be similar to the embodiment illustrated in FIG. 23 and includes extensions or covers comprising gaskets 1760a-1760d having contact surfaces 1759a-1759d configured to form a seal with tissue. End effector 1713 however also includes proximal fluid ports 1724a, 1724b positioned at an outer portion or surface 1716a of the first jaw to exhaust steam or smoke from the one or more fluid paths 1723e, 1723f in a controlled or predictable manner. In some embodiments, the fluid control system operates passively as previously described. In other embodiments, a pump or fan may be provided that is fluidically coupled to one or more fluid paths 1723a-1723f to assist in the exhaust of steam or smoke from the proximal fluid ports 1724a, 1724b. In one embodiment, the second jaw 1715b comprises one or more second fluid paths and proximal fluid ports similar to those described with respect to the first jaw 1715a. It is to be appreciated that the angle, position, and number of fluid ports may vary depending on desired operation and configuration of the end effector. As above, the outer portion or surface 1716a, 1716b of the end effector 1713 may comprise a cover.

Figure 25A:
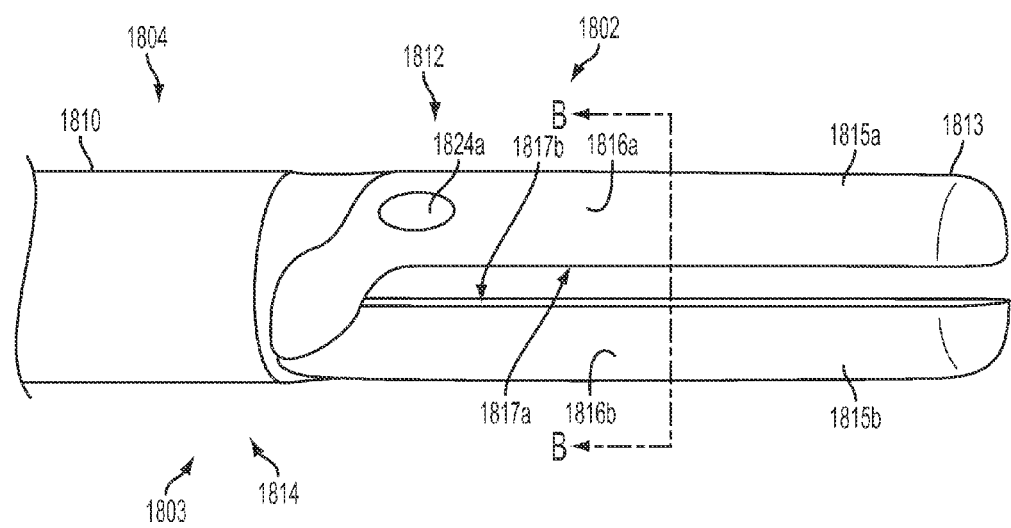
FIG. 25A illustrates a perspective view of one embodiment of a distal portion of an elongate member comprising a fluid control system.
Figure 25B:
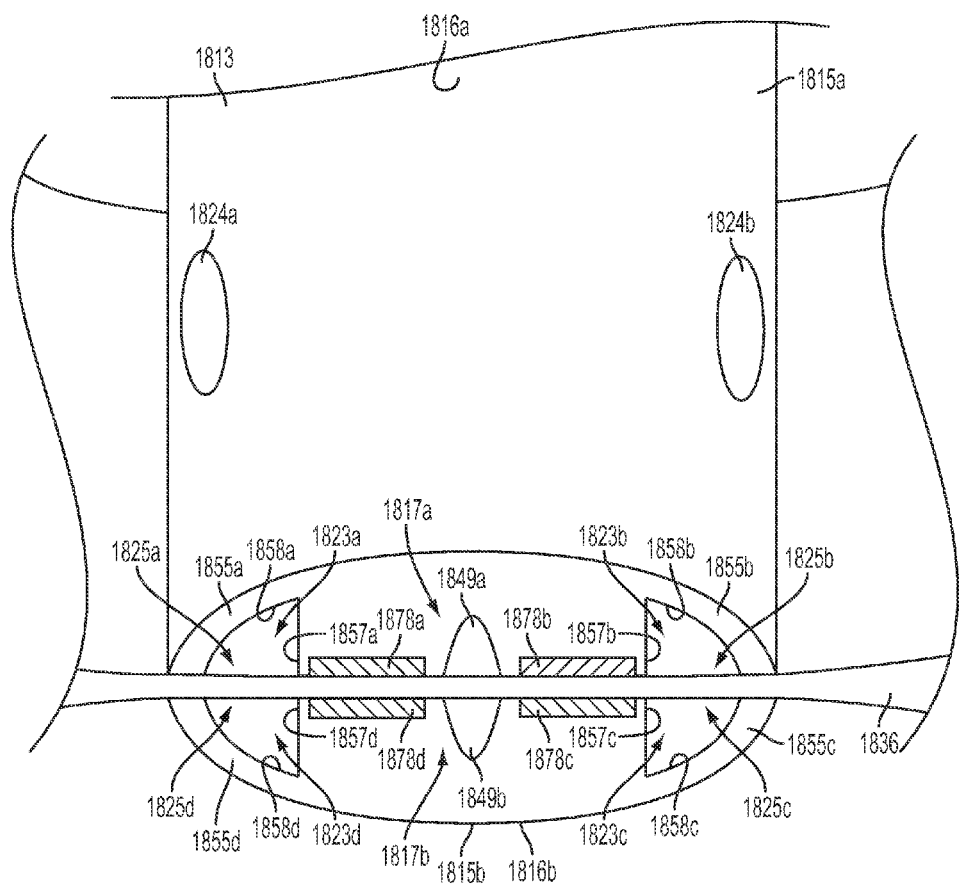
FIG. 25B illustrates a perspective view in cross-section along A-A of FIG. 25A wherein tissue is positioned between the first and second jaw of the end effector.

FIGS. 25A and 25B illustrate a distal portion 1812 of an elongate member 1804 of a medical device 1802 according to various embodiments. The medical device 1802 comprises a fluid control system 1803 including a fluid path element defining one or more fluid paths 1823a-1823d similar to the embodiment illustrated in FIG. 18. FIG. 25A illustrates the distal portion 1812 of the elongate member 1804 in perspective. FIG. 25B illustrates a cross-section along B-B and further depicts the jaws 1815a, 1815b in a closed position having target tissue 1835 positioned between working portions 1817a, 1817b of the jaws 1815a, 1815b, e.g., along electrodes 1878a-1878d or knife slot 1849a, 1849b. Outer portions or surfaces 1816a, 1816b of the jaws 1815a, 1815b include extensions 1855a-1855d, which may comprises a cover or gasket as previously described, extend away from working portions 1817a, 1817b of the end effector 1813 to form a channel or cavity defining one or more fluid paths 1823a-1823d that may extend around a perimeter or periphery of the end effector 1813. As shown, the one or more fluid paths 1823a-1823d are defined by respective surfaces 1857a-1857d and 1858a-1858d. In certain embodiments, contact surfaces 1859a-1859d of the jaws 1815a, 1815b may be configured to compress tissue to form a seal thereon. In operation, steam or smoke may be produced when energy is applied to the target tissue 1835. As such, the steam or smoke may enter the one or more fluid paths 1823a-1823d at the distal fluid ports 1825a-1825d and may thereby be captured or retained within the one or more fluid paths 1823a-1823d. In various embodiments, covers, gaskets, extensions 1855a-1855d, or outer portions or surfaces 1816a, 1816b of one or both jaws 1815a, 1815b may define one or more proximal fluid ports to fluidically communicate steam or smoke between an internal environment, e.g., a fluid path element, and an external environment, e.g., surgical field surrounding the end effector. As shown, one or more proximal fluid ports 1824a, 1824b are positioned on the extensions 1855a-1855d to exhaust the captured or retained steam or smoke in a controlled or predictable manner. In some embodiments, the fluid control system 1803 operates passively as previously described. In other embodiments, a pump or fan may be provided to assist the exhaustion of steam or smoke from the proximal fluid ports 1824a, 1824b. In one embodiment, the second jaw 1815b comprises a cover or gasket having proximal fluid ports similar to those described with respect to the first jaw 1815a. As with all of the non-limiting embodiments described herein, it is to be appreciated that angle, position, and number of fluid paths and ports may vary, e.g., in consideration of operation, dimension, or configuration of the end effector. Similarly, multiple fluid applications may be used. For example, slot 1849, generally configured to slidably receive a cutting element or blade therein, may be used as a fluid path coupled to a supply or transport component, e.g., comprising a positive or negative pressure. In this embodiment, the supply component may comprise the external environment into which steam or smoke is exhausted from the fluid path element and the transport component may comprise gravity or a form of diffusion, convection, advection, for example.

As previously described, in certain embodiments, the outer portion or surface 1816a, 1816b of the first and second jaws 1815a, 1815b may comprise or be formed on a cover, e.g., an overmolded cover, housing, or sleeve, comprising a biologically compatible materials such as a rubber, polymer, or biocompatible material, e.g., thermoset or thermoplastic polymer, silica, silicone, neoprene, etc., positioned over the end effector 1813. For example, in one embodiment, the cover may be similar to an umbrella, e.g., a rubber umbrella, positioned over the end effector 1813 that forms a soft or gentle seal with tissue to retain and redirect steam or smoke to a proximal fluid port 1824a, 1824b. In various embodiments, the cover may define a complementary dimension with that of the end effector 1813. In one embodiment, the cover snaps onto the end effector 1813 or is attached to the end effector 1813 using an adhesive. In one embodiment, a cover is applied to the surface 1816a, 1816b of the end effector 1813 and includes a chemical pre-bond treatment to enhance the chemical bond, e.g., in an overmold process.

As previously described, various embodiments of fluid control systems are configured to selectively activate the fluid control system, which may include an activation sequence of one or more steam control operation, e.g., fluid delivery, suction, or temporal or spatial sequencing of steam control operations with an operation of the end effector. For example, an activation element may be provided to manually or electronically activate the fluid control system via a switch or actuator that opens a valve or activates a pump as herein described. Notably, when a medical device comprising a two jaw system having an RF function, for example, is used for dissection, the needs of the user may change compared to those when the RF device is used for transaction and sealing. For example, opening and closing the jaws and application of suction to clear the visible surgical field in an effort to see the tissue being dissected are some of the most repetitive operations. Current methods to provide suction to clear the visible surgical field however require separate suction devices. Furthermore, current methods to provide suction also do not couple the motions of the jaws with that of the suction. According to various embodiments, a medical device, such as an RF device comprising a energy delivery function, comprises a multi-functional device comprising a suction function and a dissection function. In various embodiments, the medical device comprises intuitive one handed operation. For example the medical device may be equipped with seamless suction use while dissecting tissue and allow improved dissection techniques.

Figure 26A:
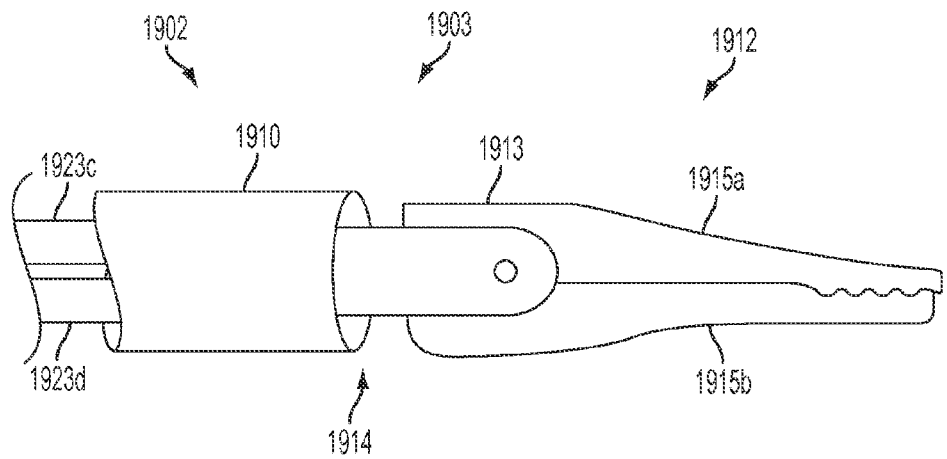
FIG. 26A illustrates a perspective view of one embodiment of a distal portion of an elongate member comprising a fluid control system.
Figure 26B:
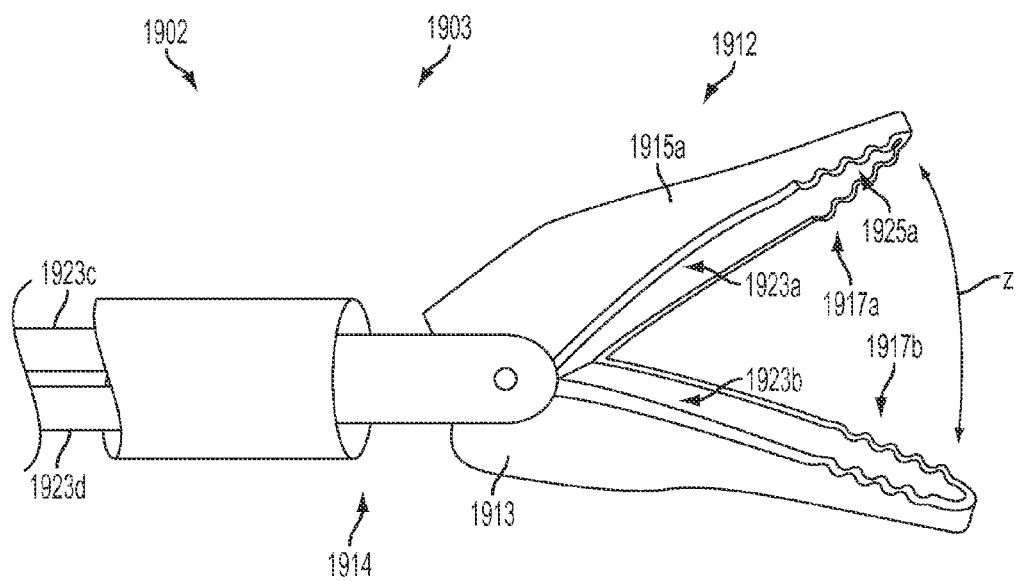
FIG. 26B illustrates a perspective view of the embodiment illustrated in FIG. 26A wherein the first and second jaws are in an open position.

Referring to FIGS. 26A and 26B, one embodiment of a distal portion 1912 of an elongate member 1904 of a medical device 1902 comprising a fluid control system is illustrated. A proximal portion of the elongate member 1904 may be similar to that previously described with respect to other embodiments. In this embodiment, the fluid control system 1903 may be configured to intake fluid, such as blood or irrigation fluid, present in the surgical field. Of course, in various embodiments, the fluid control system 1903 may be configured to intake or otherwise control fluid such as steam or smoke. The distal portion 1912 of the elongate member 1904 comprises a multi-functional end effector 1913 comprising a first jaw 1915a and a second jaw 1915b configured to open and close to dissect tissue. The first jaw 1915a and second jaw 1915b are operatively coupled to a handle through a shaft 1910. One or more fluid paths 1923a-1923d extend along the shaft 1910 and comprises one or more distal fluid ports 1925a, 1925b positioned adjacent to or between the two jaws 1915a, 1915b or working portions 1917a, 1917b thereof. The fluid paths 1923a-1923d comprise a proximal end configured to couple to a supply and transport element as herein described. In one embodiment, at least one of the fluid paths 1923a-1923d is configured to couple to a negative pressure or vacuum. In one such embodiment, an activation element is configured to couple activation of the vacuum to one of opening or closing the jaws 1915a, 1915b. For example, suction may be activated when the jaws 1915a, 1915b are opened. In some embodiments, the vacuum may be activated when the jaws 1915a, 1915b are in an open and closed position. For example, the jaws 1915a, 1915b may create a seal when closed such that the vacuum may be on when the jaws 1915a, 1915b are closed without significant suction of fluid taking place. For example, in one embodiment, each jaw 1915a, 1915b may comprise a channel defining one or more fluid paths 1923a, 1923b along a central portion of its length. In operation, the one or more fluid paths 1923a, 1923b may "wick up" fluid when the first and second jaws 1915a, 1915b are in the closed position. When the first and second jaws 1915a, 1915b are in the open position, fluid is suctioned proximally through one or more fluid paths 1923a-1923d. In various embodiments, both of the fluid paths 1923a, 1923b are configured to fluidically couple to both of the fluid paths 1923c, 1923d. For example, fluid path 1923c may comprise a proximal fluid port configured to couple to a vacuum and fluid path 1923d may comprise a proximal fluid port configured to couple to a fluid source configured to supply a fluid such as an irrigation fluid along the fluid paths 1923a and 1923b. In one embodiment, a valve is positioned between the fluid paths 1923c, 1923d to control one or more of the fluid connections between fluid paths 1923c, 1923d and fluid paths 1923a, 1923b. Depending on the desired configuration, the valve may be selectively operable by the user or may comprise multiple valves to allow unidirectional fluid flow through the valve, which may allow fluid paths 1923c, 1923d to transport fluid in the same or different directions.

Figure 27A:
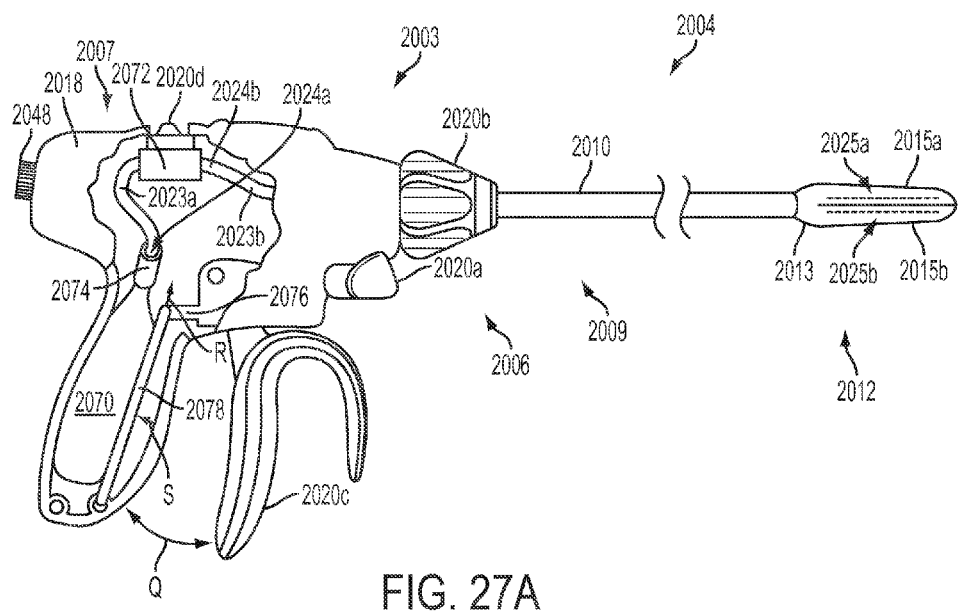
FIGS. 27A and 27B illustrate a perspective view in partial cutaway of a medical device comprising one embodiment of a fluid control system.
Figure 27B:
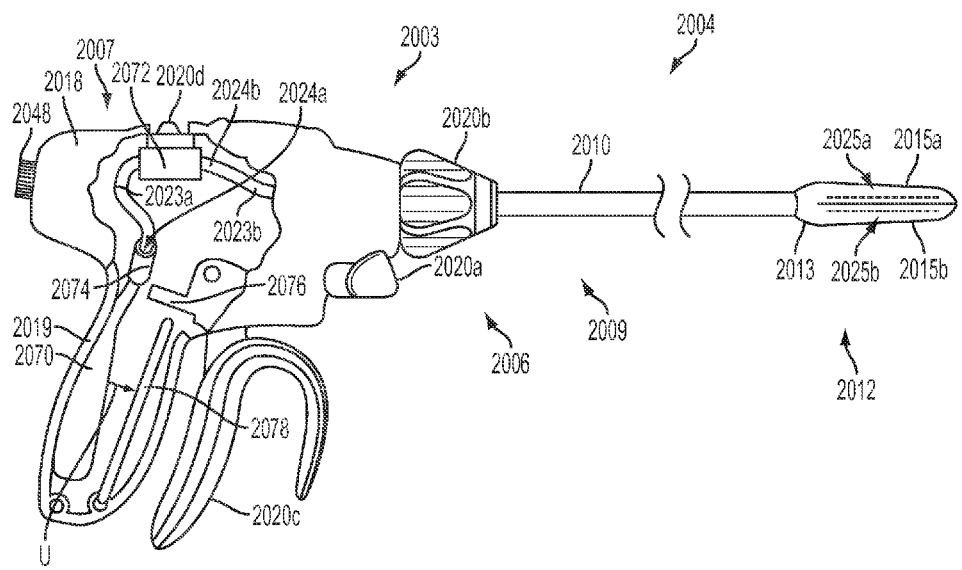

Referring to FIGS. 27A and 27B, in various embodiments, a medical device 2002 comprises a fluid control system 2003 configured to employ a steam control operation comprising a staged pressure and vacuum configured to mitigate potential blanching of adjacent tissue. For example, positive pressure may be introduced through one or more fluid paths 2023a, 2023b to clear one or more fluid ports 2025a, 2025b, e.g., vents, outlets, inlets, holes, perforations, etc., that may further be used to evacuate steam when a vacuum is applied to the one or more fluid paths 2023a, 2023b. The embodiment may be understood according to the general medical device 2002 layout previously described with respect to other embodiments. Briefly, the medical device 2002 comprises an elongate member 2004 having a proximal portion 2006 comprising a handle 2007 and a distal portion 2012 comprising an end effector 2013. A shaft 2010 is operatively coupled to the handle 2007 at a proximal end 2009 and the end effector 2013 at a distal end 2014. The handle comprises housing 2018 defining a grip 2019 and having one or more user interface controls including a trigger 2020c movable as indicated by arrow Q and a switch or button 2020d. The trigger 2020c is configured to activate ultrasonic or RF energy to seal target tissue positioned between first and second jaws 2015a, 2015b of the end effector 2013.

The fluid control system 2003 comprises a fluid path element including one or more fluid paths 2023a, 2023b that extend proximally along the handle 2007 and distally along the end effector 2013. The fluid paths 2023a, 2023b comprise distal fluid ports 2025a, 2025b positioned at outer portions or surfaces 2016a, 2016b of the first and second jaws 2015a, 2015b. The distal fluid ports 2025a, 2025b are positioned as previously described with respect to FIG. 12, however, other configurations could be used. A proximal end of the one or more fluid paths 2023a, 2023b comprises one or more proximal fluid ports 2024a, 2024b configured to fluidically couple to supply and transport elements. The fluid supply and transport elements include a fluid source and reservoir comprising a compressible bulb 2070. The compressible bulb contains a fluid that may be supplied to the one or more fluid paths 2023a, 2023b. The bulb 2070 also comprises a fluid reservoir configured to receive fluid from the one or more fluid paths 2023a, 2023b. The fluid supply and transport elements are operatively coupled to an activation element comprising a trigger mechanism. For example, actuation of the trigger 2020c along arrow Q rotates a cam arm 2076 in direction R, which may further activate energy when the trigger 2020c obtains a predetermined position during rotation.

The actuation of the trigger 2020a compresses the cam arm 2076 against a piston 2078, moving the piston 2078 in direction R to compress the bulb 2070. FIG. 27A illustrates partial actuation of the trigger 2020c to cause the bulb to be squeezed or compressed between the piston 2078 and the housing 2018. In the illustrated embodiment, the piston moves about a pivot 2079, however, in other embodiments the piston may be movable using other methods such as tracks of fixation to the trigger 2020c or cam arm 2076. When the bulb 2070 is compressed, fluid is evacuated from the bulb 2070 into the one or more fluid paths 2023a, 2023b and delivered distally at distal fluid ports 2025a, 2025b outward of the end effector 2013, as indicated by arrow P. In one embodiment, simultaneous with or just prior to activation of the energy, a positive pressure is applied to the one or more fluid paths 2023a, 2023b as previously described and a volume of fluid is ejected from the distal fluid ports 2025a, 2025b. The volume of fluid may clear the distal fluid ports 2025a, 2025b. Subsequent to the ejection of fluid, a negative pressure may be applied to the one or more fluid paths 2023a, 2023b to evacuate fluid, e.g., steam or smoke, via distal fluid ports 2025a, 2025b and through the one or more fluid paths 2023a, 2023b to the bulb 2070, which may include an exhaust. When the trigger 2020c is actuated in the direction of Q to activate the device, the actuation causes cam arm 2076 to drive piston 2078 against the bulb in direction S to rapidly squeeze the bulb 2078 and expel the fluid, e.g., air/$CO_2$, and clear the distal fluid ports 2025a, 2025b.

As the trigger 2020c is actuated further, as illustrated in FIG. 27B, the piston 2078 is allowed to move in the direction indicated by arrow U to allow the bulb 2070 to create a vacuum and draw fluid inward toward the end effector 2013 and one or more fluid paths 2023a, 2023b at the distal fluid ports 2025a, 2025b, as indicated by arrow G. The negative pressure causes fluid to be suctioned inward toward the one or more fluid paths 2023a, 2023b at the distal fluid ports 2025a, 2025b as indicated by arrow G and transported proximally to the bulb 2070. Operation of the transport component further includes a valve system comprising valves 2072, 2074 operatively coupled to the operation of the trigger 2020*c* and button 2020*d* associated with the activation element as described below. Notably, as also described below, in various embodiments, button or switch 2020*a* may similarly be operatively coupled to the transport component.

In one embodiment, activation of energy is coupled to activate the fluid control system. Similarly, in other embodiments, fluid delivery may be synchronized to energy pulses delivered to target tissue or position of the jaws. In various embodiments, the trigger 2020*c* may be coupled to the activation element to initiate the positive and negative pressure sequence as previously described. The activation element may be automated or may include one or more manual aspects. In the embodiment shown in FIGS. 27A and 27B, the bulb 2070 is positioned within the handle 2007, although in other embodiments supply components may be positioned external to the handle 2007. In the embodiment illustrated in FIGS. 27A and 27B one or more valves 2072, 2074 are connected between the bulb 2070 and the one or more fluid paths 2023*a*, 2023*b*. The valves 2072, 2074 may be wide open for application of positive pressure and then nearly closed during application of negative pressure, e.g., a metering valve, to evacuate steam over the duration of the application of energy to the target tissue. For example, valve 2074 may be a leaky duck bill valve that is wide open under pressure but steam may be evacuated through the leaky or tortuous path when the duck bill is closed. Notably, in various embodiments only one valve 2072, 2074 is provided. Additional mechanisms to stage or extend fluid control operations also are contemplated. For example, in one embodiment, the movement of the piston 2078 in direction U is dampened by a dampener (not shown) to extend the application of negative pressure to the fluid path 2023*a*, 2023*b* over the course of the application of energy to the target tissue.

Also illustrated in FIGS. 27A and 27B is an activation button 2020*d*, which may be coupled to a valve 2072. The valve 2072 may be a trumpet valve to allow the user to begin application of negative pressure within a desired sequence or may be a pump or coupled thereto to a pump to initiate negative pressure or positive pressure. The activation button 2020*d* may be provided instead of or in addition to the mechanical operation previously described to provide an additional control option.

In one embodiment, switch 2020*a* is configured to activate ultrasonic or RF energy. In one such embodiment, switch 2020*a* is operatively coupled to open a valve, initiate a pump, or release the cam 2076 from engagement with the piston 2078 to allow negative pressure from the bulb to be applied to the one or more fluid paths 2023*a*, 2023*b* to evacuate steam or smoke from the surgical field. Thus, in one such embodiment, rotating the trigger 2020*c* may cause the jaws 2015*a*, 2015*b* to rotate toward a closed position. Rotation of the trigger 2020*c* may further coincide with compression of the bulb 2070, which my clear the fluid paths 2023*a*, 2023*b* and the distal fluid ports 2025*a*, 2025*b*. Operation of switch 2020*a* may provide ultrasonic or RF energy to target tissue and further cause a valve to open or the cam 2076 to release from engagement with the piston 2078 to allow negative pressure from the bulb to be applied to the one or more fluid paths 2023*a*, 2023*b* to evacuate steam or smoke from the surgical field.

In various embodiments, when steam is evacuated, the evacuated steam may be converted to water, captured in the bulb 2070, and condensed to water. In some embodiments, a trumpet valve is provided to remove the condensed water from the bulb 2070. In one embodiment, the combined operation of positive and negative pressure is implemented with two trumpet valves staged appropriately with the activation of the trigger 2020*c*. For example, suction and irrigation lines may be connected to the device (not shown). In such an embodiment, the bulb 2070 may be eliminated and thereby the accumulation of water in the bulb 2070 also may be eliminated.

As previously described, during operation of a medical device, fluid such as steam, body fluids, irrigation fluid, or smoke, which for present purposes may be considered a fluid, may occupy the surgical field. The presence of such fluids may interfere with field of view or contaminate or damage surrounding tissues. Operation of medical devices also may present risk to tissue adjacent to the target tissue and surrounding the surgical field due to, for example, splay electricity and hot surfaces of the medical device. For example, when access is limited, it may be difficult to maneuver the medical device to protect surrounding tissue from damage due to thermal spread from accidental contact during or after operation of the device.

Figure 28A:
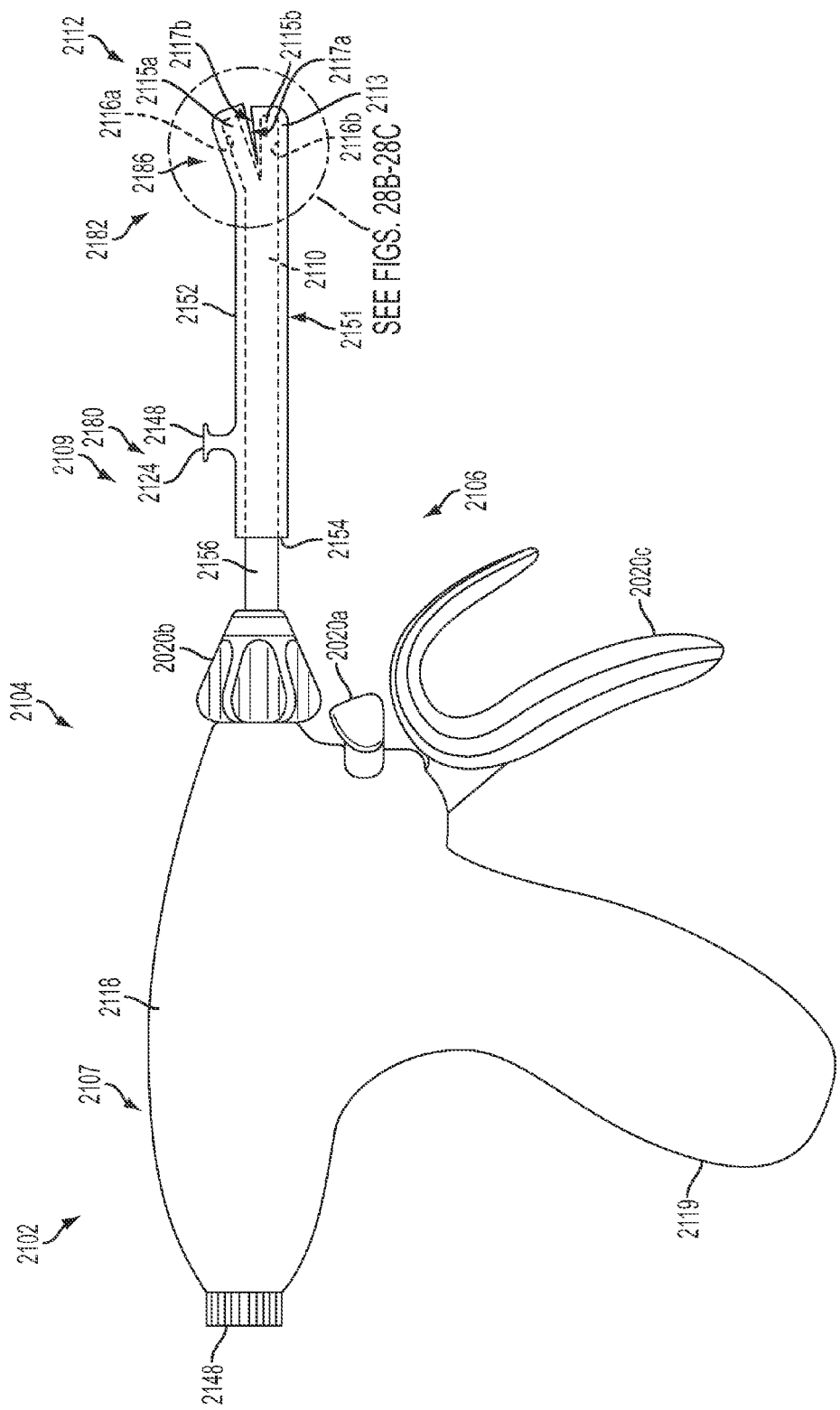
FIG. 28A illustrates a perspective view a medical device comprising of one embodiment of a fluid control system including a sleeve.
Figure 28B:
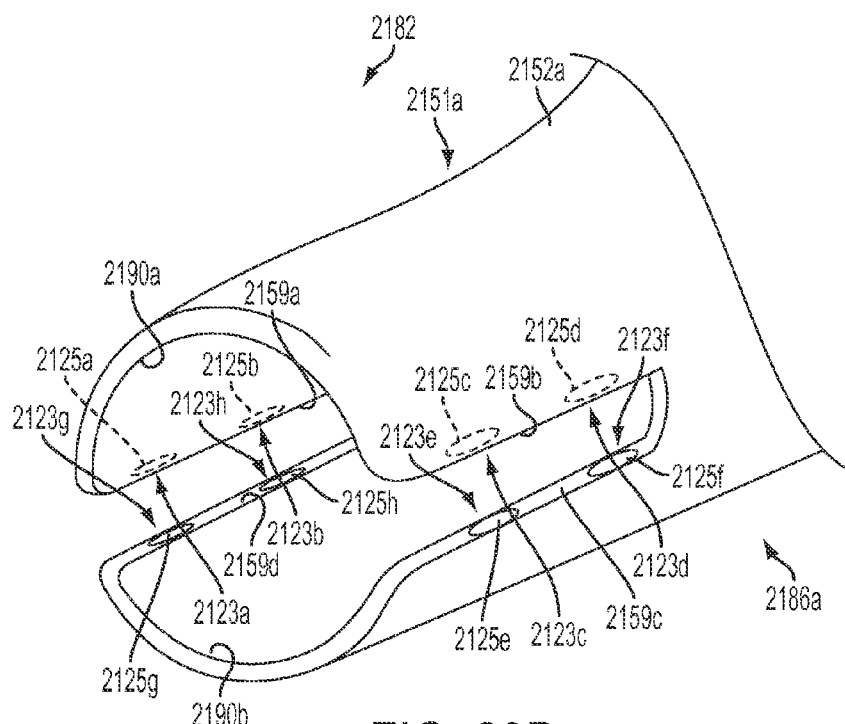
FIGS. 28B and 28C illustrate perspective views in cross-section of various embodiments of sleeves according to the embodiment illustrated in FIG. 28A.
Figure 28C:
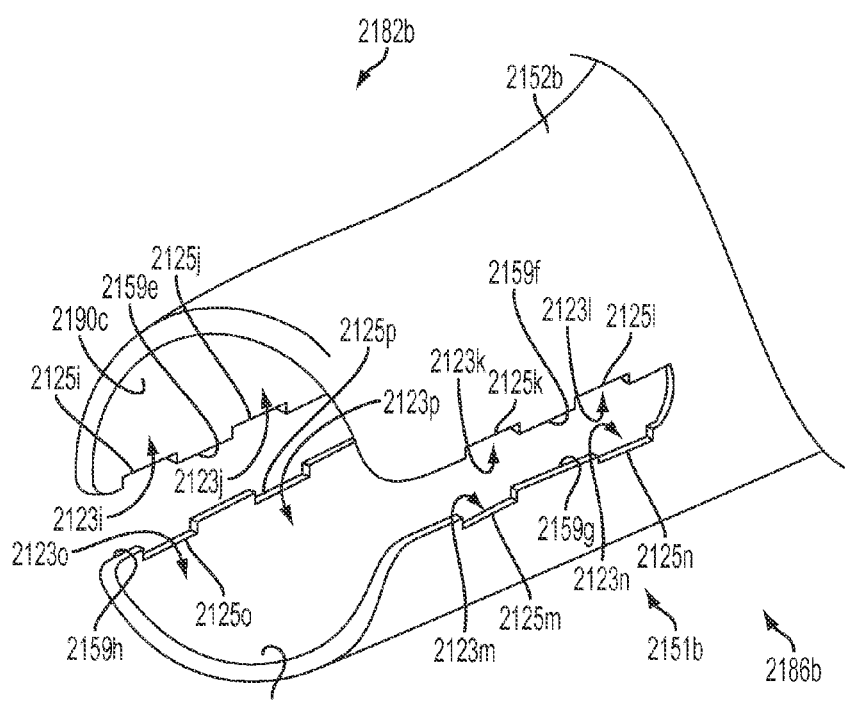

In one embodiment, referring to FIGS. 28A-28C a medical device 2102 may include or be integrated with a fluid control system 2103 comprising a fluid path element 2122 that includes a cover 2151 comprising a sleeve 2152. The layout of the medical device 2102 may be similar to those previously described with respect to other embodiments and the details are unnecessary for understanding the embodiment. Briefly, the medical device 2102 comprises an elongate member 2104 having a proximal portion 2106 comprising a handle 2107 and a distal portion 2112 comprising an end effector 2113. A shaft 2110 extends between the handle 2107 and the end effector 2113 and operatively couples the handle 2107 at a proximal end 2109 and the end effector 2113 at a distal end 2114. The handle comprises housing 2118 defining a grip 2119 and having one or more user interface controls 2120*a*-2120*d* as previously described. For example, a trigger 2120*c* and switch or button 2120*a* may be configured to operate the end effector 2113, e.g., rotate jaws or activate ultrasonic or RF energy, e.g., bipolar energy, to seal target tissue positioned between first and second jaws 2115*a*, 2115*b* of the end effector 2113.

The shaft 2110 may comprise the sleeve 2152 or the sleeve 2152 may be fitted on or around a surface 2156 of the shaft 2110. The sleeve 2152 preferably comprises an insulator material to prevent transfer of excessive heat or electrical current to tissue adjacent the target tissue or surrounding the surgical field. In one embodiment, the sleeve 2152 comprises a molded material that may snap into place of the end effector 2113 or shaft 2110 or components thereof. For example, a portion of the sleeve 2152 may snap onto a dimension of a component of the shaft 2110 or end effector 2113, e.g., using a slot or other feature associated with the end effector 2113 that is configured to slidably receive therein a cutting element or blade. In one embodiment, the sleeve 2152 comprises a proximal portion 2180 and a distal portion 2182. The proximal portion 2180 may comprise a proximal fluid port 2124 comprising a fitting configured to couple with a fluid supply and transport element. In the illustrated embodiment, the proximal fluid port 2124 comprises a luer fitting. The proximal portion 2180 may also comprise a seal positioned along surface 2154 to seal with the surface 2156 of the shaft 2110. The distal portion 2182 comprises an end effector portion 2186, also referred to as an end effector guard 2186, configured to be positioned over the end effector 2113. In various embodiments, the end effector guard 2186 may be configured to deliver fluid to a surgical field or intake steam or smoke from the surgical field. In one embodiment, the end effector guard 2186 also provides a thermal barrier between the end effector 2113 and the surgical field.

FIGS. 28B and 28C illustrate cross-sections of exemplary configurations of a portion of the guard 2184 positioned along the distal portion 2182 of the sleeve 2152, as indicated with broken lines in FIG. 28A. The end effector 2113 is not shown for clarity but may be positioned along surface 2190a-2190d. In one embodiment, the end effector guard 2186 comprises a pliable material. At least a portion of the sleeve 2152 at least partially defines one or more fluid paths 2123a-2123p extending from distal fluid ports 2125a-2125p to the proximal fluid port 2124. The one or more fluid paths 2123a-2123p may comprise one or more first fluid paths extending along the end effector 2113 fluidically coupled to one or more second fluid paths extending along the shaft 2110. In one embodiment, the one or more fluid paths 2123a-2123p are defined between one or more surfaces of the sleeve 2152 and one or more surfaces 2116a, 2116b, 2156 of the end effector 2113 or shaft 2110. For example, a portion of the sleeve 2152 may loosely fit over the shaft 2110 or end effector 2113 or may comprise a ridge or channel defined thereon for fluid to transport therethrough. In one embodiment, the proximal fluid port 2124 may be flush with the sleeve 2152 or may extend outward or branch off of the sleeve 2152. In various embodiments, the proximal fluid port 2124 may be fluidically coupled to a vacuum to pull steam generated via the cooking of tissue within the one or more fluid paths 2123a-2123p at the distal fluid ports 2125a-2125p adjacent to the end effector 2113, e.g., drawn under the end effector guard 2186, where it can be removed with a vacuum luer port 2184. In certain embodiments, the sleeve 2152 comprises a proximal seal positional along surface 2154 configured to fluidically seal with a surface 2156 of shaft. For example, when the sleeve 2152 defines one or more fluid paths 2123a-2123p in conjunction with the shaft 2110 or end effector 2113, e.g., comprises a loose fit or defines channels, the proximal seal allows a vacuum to be applied through the one or more fluid paths 2123a-2123p. In the embodiment illustrated in FIG. 28B, the end effector guard 2186a includes a surface 2190a, 2190b configured to be positioned over the surfaces 2116a, 2116b of the end effector 2113 and defines distal fluid ports 2125a-2125h. When the guard 2186a is positioned on the end effector 2113, the distal fluid ports 2125a-2125h are positioned adjacent to the first and second jaws 2115a, 2115b, e.g., along a working portion 2117a, 2117b thereof, to communicate fluid between the one or more fluid paths 2123a-2123p and the surgical field. The end effector guard 2186a further defines fluid paths 2123a-2123h that fluidically couple with the proximal fluid port 2124. As previously described, fluid paths 2123a-2123h may be further coupled to second fluid paths proximally, which may be defined within the proximal portion 2180 of the sleeve 2152a or in conjunction with the shaft 2110 or surface 2156 thereof. In the embodiment illustrated in FIG. 28C, the end effector guard 2186b defines distal fluid ports 2125i-2125p configured to be positioned adjacent to the first and second jaws 2115a, 2115b, e.g., along a working portion 2117a, 2117b thereof, to allow fluid to flow between the surgical field and the one or more fluid paths 2123i-2123p. The one or more fluid paths 2123i-2123p are defined between an adjacent surface 2116a, 2116b of the end effector 2113 and a surface 2190c, 2190d of the guard 2186b which may be loosely fit over the end effector 2113 or defined by channels formed in the surface 2190c, 2190d thereby forming fluid paths 2123i-2123p. As previously described, fluid paths 2123i-2123p may be further fluidically coupled to second fluid paths extending along a proximal portion 2180 of the sleeve 2152b or in conjunction with the shaft 2110 or surface 2156 thereof.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to,"

"related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

Various aspects of the subject matter described herein are set out in the following numbered clauses:

1. A medical device comprising: a fluid control system to control the flow of a fluid produced when the medical device applies energy to heat a target tissue, the fluid control system comprising: a fluid path element defining a fluid path to transport a fluid therethrough; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path; and an effector fluidically coupled to the fluid control system, the end effector comprising a working portion configured to apply energy to the target tissue, wherein the distal fluid port is positioned adjacent to the working portion of the end effector.

2. The medical device of clause 1, wherein the proximal fluid port is fluidically coupled to a transport component to actively transport fluid through the one or more fluid paths.

3. The medical device of clause 2, wherein the transport component comprises a pressure differential.

4. The medical device of clause 3, wherein the transport component is fluidically coupled to a pump that provides the pressure differential.

5. The medical device of clause 2, wherein the proximal fluid port is fluidically coupled to a supply component, wherein the supply component comprises one of a fluid source to supply fluid for transport through the fluid path and an environment to exhaust fluid transported through the fluid path element.

6. A medical device comprising: a fluid control system to control the flow of a fluid produced when the medical device applies energy to heat a target tissue, the fluid control system comprising: a fluid path element defining a fluid path to transport a fluid therethrough, wherein the fluid path comprises a first fluid path at least partially defined by a first surface; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path; and an effector fluidically coupled to the fluid control system, the end effector comprising a working portion configured to apply energy to the target tissue, wherein the distal fluid port is positioned adjacent to the working portion of the end effector.

7. The medical device of clause 6, wherein the first surface defines a channel extending along a central portion of the end effector.

8. The medical device of clause 7, wherein the end effector comprises a first jaw and a second jaw, wherein the first jaw and the second jaw are operatively coupled and movable between an open position and a closed position, and wherein the proximal fluid port is fluidically coupled to the first fluid path and to a transport component comprising a vacuum to intake the fluid from the first fluid path when the first and second jaws are in the open position.

9. The medical device of clause 7, wherein the end effector comprises a first jaw, a second jaw, and a cutting element positioned between the first and second jaw, wherein the cutting element is slidably movable through the channel.

10. The medical device of clause 9, further comprising a gasket positioned along a perimeter of the first jaw, wherein the gasket comprises a tissue contact surface configured to form a seal with tissue when compressed against the tissue.

11. A medical device comprising: a fluid control system to control the flow of a fluid produced when the medical device applies energy to heat a target tissue, the fluid control system comprising: a fluid path element defining a fluid path to transport a fluid therethrough, wherein the fluid path comprises a first fluid path at least partially defined by a first surface, wherein the first surface extends along a perimeter of the end effector; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path; and an effector fluidically coupled to the fluid control system, the end effector comprising a working portion configured to apply energy to the target tissue, wherein the distal fluid port is positioned adjacent to the working portion of the end effector.

12. The medical device of clause 11, wherein the fluid path element comprises one of an extension and a cover comprising a second surface extendable around the perimeter of the end effector, adjacent to the first surface, to at least partially define the first fluid path together with the first surface.

13. The medical device of clause 12, wherein the fluid path element comprises the cover, wherein the cover comprises a gasket positionable along the perimeter of the end effector and comprising the second surface, and wherein the gasket further comprises a tissue contract surface configured to form a seal with tissue when compressed against the tissue.

14. The medical device of clause 12, further comprising a gasket positioned on the one of the extension and the cover, wherein the gasket is configured to form a seal with tissue.

15. The medical device of clause 14, wherein the gasket defines at least a portion of the second surface, wherein the gasket further defines a second fluid path fluidically coupled to the first fluid path via an intermediate fluid port formed on the second surface of the gasket.

16. The medical device of clause 12, wherein the fluid path element comprises the cover, wherein the cover comprises a mold positionable on the end effector and comprising the second surface.

17. The medical device of clause 12, wherein the proximal fluid port is positioned along the one of the extension and the cover to allow one of steam and smoke to passively exhaust from the first fluid path element.

18. The medical device of clause 12, wherein the fluid path element comprises the cover, wherein the cover comprises a sleeve configured to extend along a shaft coupled to the end effector, and wherein the proximal fluid port is positioned along the sleeve.

19. The medical device of clause 12, wherein the end effector defines a second fluid path fluidically coupled to the first fluid path via an intermediate fluid port formed on the first surface.

20. The medical device of clause 19, wherein the proximal fluid port is positioned at an outer surface of the end effector to allow one of steam and smoke to passively exhaust from the second fluid path element.

21. A medical device comprising: a fluid control system to control the flow of a fluid produced when the medical device applies energy to heat a target tissue, the fluid control system comprising: a fluid path element defining a fluid path to transport a fluid therethrough; a distal fluid port fluidically coupled to the fluid path element, the distal fluid port configured to intake the fluid for transport through the fluid path and to transport the fluid through the fluid path; and a proximal fluid port fluidically coupled to the fluid path element, the proximal fluid port configured to intake the fluid transported through the fluid path and to exhaust the fluid transported through the fluid path; an effector fluidically coupled to the fluid control system, the end effector comprising a working portion extending along a first jaw and a second jaw, the working portion configured to apply bipolar energy to the target tissue, wherein the distal fluid port is positioned adjacent to the working portion of the end effector; and an activation element configured to activate a supply and transport element to transport one the fluid through the fluid path.

22. The medical device of clause 21, wherein the activation element is configured to activate the supply and transport element to transport fluid or smoke through the fluid path to correspond with an operation of the end effector.

23. The medical device of clause 21, wherein the activation element is coupled to a valve fluidically coupled to the fluid path element, wherein the valve is positioned between a pressure differential, and wherein the activation element is configured to open the valve to allow fluid to be transported through the fluid path element.

24. The medical device of clause 22, wherein the activation element is coupled to an actuator, wherein actuation of the actuator communicates engagement of a piston with a fluid element, wherein the piston is configured to drive fluid from the fluid element to cause the fluid to be transported through the fluid path and exhausted from the distal fluid port.

25. The medical device of clause 24, wherein at least one of the supply and transport element comprises a compressible bulb.

26. The medical device of clause 25, wherein the piston is configured to disengage the compressible bulb after the bulb has been compressed to allow negative pressure within the compressible bulb to transport one of fluid or smoke through the fluid path toward the compressible bulb.

27. The medical device of clause 26, further comprising a valve fluidically coupled to the fluid path element, wherein the valve allows fluid to be transported through the fluid path toward the distal fluid port at a greater rate than fluid is transported through the fluid path toward the proximal fluid port.

28. The medical device of clause 26, wherein the activation element comprises a switch to activate the supply and transport element, wherein the supply and transport element comprises a pump fluidically coupled to the fluid path element.

29. A medical device comprising: an elongate member having a proximal portion comprising a handle coupled to a proximal end of a shaft and a distal portion comprising an end effector coupled to a distal end of a shaft, the end effector comprising a first jaw, a second jaw, and a working portion, wherein the end effector is configured to apply energy to heat target tissue; a fluid control system configured to control one of steam and smoke generated when the end effector applies energy to heat target tissue, the fluid control system comprising a fluid path element comprising a fluid path; a distal fluid port positioned adjacent to the working portion of the end effector and fluidically coupled to the fluid path element; and a proximal fluid port fluidically coupled to the supply and transport element; wherein the fluid path is defined along a perimeter of the end effector between a first surface and a second surface, wherein the second surface comprises a gasket configured to form a seal with tissue.

30. A medical device comprising: an elongate member comprising an end effector positioned along a distal portion thereof; a fluid control system fluidically coupled to the elongate member, the fluid control system configured to control fluid generated when the end effector applies energy to target tissue, the fluid control system comprising: a fluid path element comprising one or more fluid paths; a distal fluid port fluidically coupled to at least one of the one or more fluid paths and positioned adjacent to a working portion of the end effector; and a proximal fluid port fluidically coupled to at least one of the one or more fluid paths fluidically coupled to a supply and transport element; wherein the supply and transport element is configured to one of evacuate the fluid adjacent to the working portion of the end effector through at least one of the one or more fluid paths and supply a fluid for transport through at least one of the one or more fluid paths for delivery from the distal fluid port; and wherein the supply and transport element is configured to be operatively coupled to an activation element configured to activate the supply and transport element when end effector applies energy to the target tissue.

31. A medical device comprising: an elongate member having a proximal portion and a distal portion; a fluid control system configured to control a fluid generated when the medical device applies energy to target tissue, the fluid control system comprising: a fluid path element comprising a fluid path extending along the elongate member, the fluid path comprising: a proximal fluid port configured to couple to a fluid supply and transport element to transport fluid through the fluid path; and a distal fluid port positioned along the distal portion of the elongate member configured to deliver the fluid transported through the fluid path and intake the fluid into the fluid path element.

32. The medical device of clause 31, wherein the elongate member comprises a shaft having a proximal end and a distal end, wherein the proximal end is configured to couple to a handle along the proximal portion of the elongate member, wherein the distal end is configured to couple to an end effector along the distal portion of the elongate member, and wherein the end effector comprises a working portion configured to apply energy to the target tissue.

33. The medical device of clause 32, wherein the fluid path element comprises one or more channels defined within the shaft.

34. The medical device of clause 32, wherein the fluid path element comprises a sleeve extending along the shaft, wherein the sleeve defines at least a portion of the fluid path element.

35. The medical device of clause 34, wherein the sleeve comprises one or more proximal fluid ports positioned there along.

36. The medical device of clause 32, wherein the fluid path comprises one or more fluid paths defined by one or more tubes extending along the shaft.

37. The medical device of clause 32, wherein the distal fluid port comprises one or more distal fluid ports positioned at the distal end of the shaft, proximal to the working portion of the end effector.

38. The medical device of clause 32, wherein the distal fluid port comprises one or more first distal fluid ports positioned along the shaft and one or more second distal fluid ports positioned along the end effector.

39. The medical device of clause 32, wherein the supply and transport element is configured to supply a fluid comprising a liquid adjacent to the end effector to flush tissue adjacent to the target tissue with the liquid, and wherein the liquid is supplied at a temperature configured to cool the adjacent tissue and condense steam produced when the end effector applies energy to heat the target tissue.

40. The medical device of clause 32, wherein the fluid control system is configured to deliver fluid adjacent to the end effector to form a protective barrier of fluid between the end effector and tissue adjacent to the end effector.

41. The medical device of clause 32, wherein the supply and transport element is configured to transport a fluid comprising a gas through the fluid path to disperse one of steam and smoke adjacent to the distal portion of the elongate member.

42. The medical device of clause 32, wherein the supply and transport element is configured to transport a fluid comprising a liquid through the fluid path to the distal fluid port, wherein the distal fluid port comprises a nozzle configured to produce a mist.

43. The medical device of clause 32, wherein the supply and transport element is configured to provide a fluid at a temperature configured to condense steam adjacent to the distal portion of the elongate member.

44. A medical device comprising: an elongate member having a proximal portion and a distal portion, wherein the distal portion of the elongate member comprises an end effector coupled to a distal end of a shaft; a fluid control system configured to control a fluid generated when the medical device applies energy to target tissue, the fluid control system comprising: a fluid path element comprising a fluid path extending along the end effector, the fluid path comprising: a proximal fluid port configured to couple to a fluid supply and transport element to transport fluid through the fluid path; and a distal fluid port positioned along the distal portion of the elongate member configured to deliver the fluid transported through the fluid path and intake the fluid into the fluid path element.

45. The medical device of clause 44, wherein the distal fluid port comprises one or more distal fluid ports positioned along the end effector.

46. The medical device of clause 44, wherein the one or more distal fluid ports are positioned adjacent to a working portion of the end effector.

47. The medical device of clause 46, wherein the end effector defines at least a portion of the fluid path element.

48. The medical device of clause 47, wherein the fluid path element comprises a cover positionable on the end effector.

49. The medical device of clause 47, wherein the fluid path element comprises one or more tubes extending along a perimeter of the end effector and defining a plurality of the one or more distal fluid ports, wherein the plurality of distal fluid ports are positioned adjacent to the working portion and are configured to deliver fluid outward of the end effector 50. A medical device comprising: an elongate member having a proximal portion and a distal portion; a fluid control system configured to control a fluid generated when the medical device applies energy to target tissue, the fluid control system comprising: a fluid path element comprising a fluid path extending along the elongate member, the fluid path comprising: a proximal fluid port configured to couple to a fluid supply and transport element to transport fluid through the fluid path; a distal fluid port positioned along the distal portion of the elongate member configured to deliver the fluid transported through the fluid path and intake the fluid into the fluid path element; and an activation element configured to activate the supply and transport element to transport fluid or smoke through the fluid path element.

51. The medical device of clause 50, wherein the activation element is configured to sequence activation of the supply and transport element to transport fluid or smoke through the fluid path with an operation of the end effector.

What is claimed is:

1. A medical device, comprising:
   an end effector, comprising:
      a first jaw comprising an inner surface and an outer surface;
      a second jaw comprising an inner surface and an outer surface, wherein at least one of the first jaw or the second jaw is rotatably movable to capture target tissue between the inner surface of the first jaw and the inner surface of the second jaw; and
      a working portion that extends from a proximal end to a distal end of at least one of the inner surface of the first jaw or the inner surface of the second jaw, wherein the working portion comprises an electrode to apply energy to the target tissue in contact with the working portion at a target tissue site;
   a fluid control system, comprising:
      a fluid path element defining one or more than one fluid path to transport a fluid, wherein at least one of the one or more than one fluid path is defined by a lumen that defines a plurality of distal fluid ports to at least one of deliver the fluid to or intake the fluid from the target tissue site, wherein the at least one fluid path is situated on and extends along the outer surface of the first jaw or the outer surface of the second jaw adjacent to the working portion, and wherein the plurality of distal fluid ports are positioned along and external to the working portion between the proximal end and the distal end of the working portion; and
      a proximal fluid port fluidically coupled to the one or more than one fluid path;
   a transport component coupled to the proximal fluid port, wherein the transport component is configured to cause the fluid to move through the one or more than one fluid path; and
   an activation element to control activation of the transport component based on at least one operation of the end effector, wherein the activation element is configured to activate the transport component to cause the fluid to move through the plurality of distal fluid ports of the at least one fluid path sequential to the application of energy to the target tissue by the electrode.

2. The medical device of claim 1, wherein the transport component comprises a pressure differential.

3. The medical device of claim 2, wherein the transport component is fluidically coupled to a pump that provides the pressure differential.

4. The medical device of claim 1, further comprising a supply component coupled to the proximal fluid port, wherein the supply component comprises one of a fluid source to supply the fluid to the plurality of distal fluid ports or a fluid reservoir to receive the fluid from the plurality of distal fluid ports.

5. The medical device of claim 1, wherein the sequential activation comprises activating the transport component before or after the application of the energy by the electrode.

6. The medical device of claim 1, wherein the sequential activation comprises activating the transport component before and either during or after the application of the energy by the electrode.

7. The medical device of claim 1, wherein the activation element is configured to activate the transport component to cause the fluid to move through the plurality of distal fluid ports of the at least one fluid path at a time defined with respect to an operation of the end effector.

8. The medical device of claim 1, wherein the sequential activation is controlled via one or more than one sequence preprogrammed in a memory module.

9. The medical device of claim 1, wherein the activation element is configured to activate the transport component to deliver a first fluid through the plurality of distal fluid ports of the at least one fluid path to at least one of disperse steam or absorb heat from the steam after the application of the energy to the target tissue by the electrode.

10. The medical device of claim 9, wherein the first fluid comprises a biologically compatible gas.

11. The medical device of claim 9, wherein the transport component is further configured to deliver the first fluid at one or more than one of a temperature, a rate, and a pattern to disperse the steam or absorb the heat from the steam.

12. The medical device of claim 1, wherein the activation element is configured to activate the transport component to deliver a first fluid through the plurality of distal fluid ports of the at least one fluid path to at least one of cool the target tissue or condense steam after the application of the energy to the target tissue by the electrode.

13. The medical device of claim 12, wherein the first fluid comprises a biologically compatible liquid.

14. The medical device of claim 12, wherein the first fluid is delivered at one or more than one of a volume, a rate, and a location to form a thermal barrier between the steam and surrounding tissue at the target tissue site.

15. The medical device of claim 1, wherein the plurality of distal fluid ports of the at least one fluid path are positioned where the fluid is produced or released during the application of the energy to the target tissue by the electrode.

16. A medical device, comprising:
an end effector, comprising:
a proximal end;
a distal end;
a first jaw comprising an interior surface and an exterior surface that extend between the proximal end and the distal end;
a second jaw comprising an interior surface and an exterior surface that extend between the proximal end and the distal end, wherein the end effector is configured to capture target tissue between the interior surface of the first jaw and the interior surface of the second jaw; and
a working portion defined by at least one of the interior surface of the first jaw or the interior surface of the second jaw, wherein the working portion comprising an electrode to apply energy to the target tissue captured between the interior surface of the first jaw and the interior surface of the second jaw at a target tissue site;
a fluid control system, comprising:
at least one fluid path element, wherein each fluid path element defines one or more than one fluid path to transport a fluid, wherein at least one of the one or more than one fluid path of each fluid path element is defined by a tube which defines a plurality of distal fluid ports to at least one of deliver the fluid to or intake the fluid from the target tissue site, wherein the at least one fluid path of each fluid path element is coupled to and extends along the exterior surface of the first jaw or the exterior surface of the second jaw proximate to the working portion, and wherein the plurality of distal fluid ports are positioned along and peripheral to the working portion between the proximal end and the distal end of the end effector;
a transport component configured to cause the fluid to move through the one or more than one fluid path of each fluid path element; and
an activation element to control activation of the transport component based on at least one operation of the end effector, wherein the activation element is configured to activate the transport component to cause the fluid to move through the plurality of distal fluid ports of the at least one fluid path of each fluid path element sequential to the application of energy to the target tissue by the electrode.

17. The medical device of claim 16, wherein the sequential activation comprises activating the transport component before or after the application of the energy by the electrode.

18. The medical device of claim 16, wherein the sequential activation is controlled via one or more than one sequence preprogrammed in a memory module.

19. A medical device, comprising:
an end effector, comprising:
a first jaw comprising an inner surface and an outer surface, wherein the inner surface of the first jaw defines a first plane;
a second jaw comprising an inner surface and an outer surface, wherein the inner surface of the second jaw defines a second plane, and wherein the end effector is configured to capture target tissue between the inner surface of the first jaw and the inner surface of the second jaw; and
a working portion defined by the inner surface of the first jaw and the inner surface of the second jaw, wherein the working portion comprises an electrode to apply energy to the target tissue at a target tissue site;
a fluid control system to transport a fluid, the fluid control system comprising:
a first fluid path defined by tubing attached to and extending along the outer surface of the first jaw adjacent to a longitudinal edge of the inner surface of the first jaw, wherein the tubing of the first fluid path defines a first plurality of laterally-facing fluid ports arranged in a plane parallel to the first plane to at least one of deliver the fluid to or intake the fluid from the target tissue site, and wherein the first plurality of laterally-facing fluid ports are positioned external to the working portion along the first jaw;

a second fluid path defined by tubing attached to and extending along the outer surface of the second jaw adjacent to a longitudinal edge of the inner surface of the second jaw, wherein the tubing of the second fluid path defines a second plurality of laterally-facing fluid ports arranged in a plane parallel to the second plane to at least one of deliver the fluid to or intake the fluid from the target tissue site, and wherein the second plurality of laterally-facing fluid ports are positioned external to the working portion along the second jaw; and a proximal fluid port fluidically coupled to the first fluid path and the second fluid path;

a transport component coupled to the proximal fluid port, wherein the transport component is configured to cause the fluid to move through the first fluid path and the second fluid path; and an activation element to control activation of the transport component based on at least one operation of the end effector, wherein the activation element is configured to activate the transport component to cause the fluid to move through the first plurality of laterally-facing fluid ports of the first fluid path and the second plurality of laterally-facing fluid ports of the second fluid path at sequential to the application of energy to the target tissue by the electrode.

20. The medical device of claim 19, wherein the fluid control system further comprises a third fluid path defined by tubing positioned external to the end effector, wherein the third fluid path branches into the first fluid path and the second fluid path.

* * * * *